(12) United States Patent
Morse et al.

(10) Patent No.: US 10,406,248 B2
(45) Date of Patent: Sep. 10, 2019

(54) MOLECULAR IMAGING OF CANCER CELLS IN VIVO

(75) Inventors: David L. Morse, Tampa, FL (US); Robert J. Gillies, Tampa, FL (US); Amanda Huynh, Land O Lakes, FL (US); Josef Vagner, Tucson, AZ (US)

(73) Assignees: H. Lee Moffitt Cancer Center and Research Institute, Inc., Tampa, FL (US); Arizona Board Of Regents on Behalf of the University of Arizona, Tucson, AZ (US)

( * ) Notice: Subject to any disclaimer, the term of this patent is extended or adjusted under 35 U.S.C. 154(b) by 141 days.

(21) Appl. No.: 14/240,305

(22) PCT Filed: Sep. 5, 2012

(86) PCT No.: PCT/US2012/053813
§ 371 (c)(1),
(2), (4) Date: Feb. 21, 2014

(87) PCT Pub. No.: WO2013/036543
PCT Pub. Date: Mar. 14, 2013

(65) Prior Publication Data
US 2014/0161725 A1 Jun. 12, 2014

Related U.S. Application Data

(60) Provisional application No. 61/533,198, filed on Sep. 10, 2011.

(51) Int. Cl.
| | | |
|---|---|---|
| *A61K 51/00* | (2006.01) | |
| *A61M 36/14* | (2006.01) | |
| *A61K 49/00* | (2006.01) | |
| *C07K 7/06* | (2006.01) | |
| *C07K 7/08* | (2006.01) | |

(52) U.S. Cl.
CPC ...... *A61K 49/0056* (2013.01); *A61K 49/0021* (2013.01); *C07K 7/06* (2013.01); *C07K 7/08* (2013.01)

(58) Field of Classification Search
CPC .... A61K 49/00; A61K 49/0021; A61K 38/00; A61K 49/056; A61K 49/0056; C07K 7/06; C07K 7/08
USPC ... 424/1.11, 1.65, 1.9, 9.1, 9.2, 9.3, 9.4, 9.5, 424/9.6; 534/7, 10–16; 530/300; 514/1, 514/1.11, 19.2
See application file for complete search history.

(56) References Cited

U.S. PATENT DOCUMENTS

| | | | | |
|---|---|---|---|---|
| 5,573,909 A * | 11/1996 | Singer | ............... | C09K 11/06 435/5 |
| 7,388,080 B2 * | 6/2008 | Kurt-Jones et al. | ....... | 530/388.1 |
| 2007/0128586 A1 * | 6/2007 | Visvanathan | ........ | C12Q 1/6883 435/5 |
| 2009/0081157 A1 * | 3/2009 | Kornbluth | .............. | A61K 39/21 424/85.2 |
| 2010/0143336 A1 * | 6/2010 | Heffernan | ............ | C07K 14/715 424/130.1 |
| 2011/0104210 A1 | 5/2011 | Black | | |
| 2011/0110852 A1 | 5/2011 | Miller | | |

FOREIGN PATENT DOCUMENTS

WO 2010124226 10/2010

OTHER PUBLICATIONS

Escobedo et al, Curr. Opin. Chem. Biol., Feb. 2010, vol. 14, No. 1, pp. 1-11.*
Guan et al, Journal of Biological Chemistry, vol. 285, No. 31, pp. 23755-23762. (Year: 2010).*
Alexander et al, Journal of Pharmacological and Toxicological Methods, vol. 41, pp. 55-58. (Year: 1999).*
Adams, "Toll-like receptor agonists in cancer therapy", Immunotherapy, 1 (6):949-64 (2009).
Agnihotri, et al., "Structure-activity relationships in toll-like receptor 2-agonists leading to simplified monoacyl lipopeptides", J Med Che., 54(23):8148-60 (2011).
Akira and Takeda, "Toll-like receptor signaling", Nat Rev Immunol, 4 (7):499-511 (2004).
Akira, et al., "Toll-like receptors: critical proteins linking innate and acquired immunity", Nat Immunol, 2(8):675-80 (2011).
Albertini, et al., "Lymphatic mapping and sentinel node biopsy in the patient with breast cancer", JAMA, 276:1818-22 (1996).
Alexopoulou, et al., "Hyporesponsiveness to vaccination with Borrelia burgdorferi OspA in humans and in TLR1- and TLR2-deficient mice", Nat Med., 8 (8):878-84 (2002).
Aliprantis, et al., "Cell activation and apoptosis by bacterial lipoproteins through toll-like receptor-2", Science, 285(5428):736-9 (1999).
Angst, et al., "How to counter the problem of R1 resection in duodenopancreatectomy for pancreatic cancer", J Gastrointest Surg, 16 (3):673 (2012).
Baggett, et al., "Thermostability of firefly luciferases affects efficiency of detection by in vivo bioluminescence", Mol Imaging, 3:324-32 (2004).
Barkey et al., "Development of melanoma-targeted polymer micelles by conjugation of a melanocortin 1 receptor (MC1R) specific ligand", J Med Chem., 54 (23), 8078-84 (2011).
Belisle, et al., "Fatty acids of Treponema pallidum and Borrelia burgdorferi lipoproteins", J Bacteriol, 176(8)2151-7 (1994).
Berg, et al., "Synthetic lipopeptide Pam3CysSer(Lys)4 is an effective activator of human platelets", Am J Physiol, 266(6 Pt 1):C1684-91(1994).

(Continued)

*Primary Examiner* — D. L. Jones
(74) *Attorney, Agent, or Firm* — Pabst Patent Group LLP

(57) ABSTRACT

Cellular targets on cancer cells have been identified that can be used with targeted molecular imaging to detect the cancer cells in vivo. Non-invasive methods for detecting cancer cells, such as metastasized cancer cells, are therefore provided. Also provided are compositions and kits for use in the disclosed methods.

22 Claims, 32 Drawing Sheets

Specification includes a Sequence Listing.

(56) References Cited

OTHER PUBLICATIONS

Bessler, et al., "Synthetic lipopeptide analogs of bacterial lipoprotein are potent polyclonal activators for murine B lymphocytes", J Immunol, 135(3):1900-5 (1985).
Braun, et al., "Covalent lipoprotein from the outer membrane of *Escherichia coli*", Biochim Biophys Acta, 415(3):335-77 (1975).
Brennan, et al., "CA IX is an independent prognostic marker in premenopausal breast cancer patients with one to three positive lymph nodes and a putative marker of radiation resistance", Clin Cancer Res 12:6421-6431 (2006).
Buwitt-Beckmann, et al., "Toll-like receptor 6-independent signaling by diacylated lipopeptides", Eur J Immunol, . 35(1):282-9 (2005a).
Buwitt-Beckmann, et al., "Lipopeptide structure determines TLR2 dependent cell activation level", FEBS J, 272(24):6354-64 (2005b).
Campbell, et al., "Classification of R1 resections for pancreatic cancer: the prognostic relevance of tumour involvement within 1 mm of a resection margin", Histopathology, 55 (3), 277-83 (2009).
Celis, et al., "Toll-like receptor ligands energize peptide vaccines through multiple paths", Cancer Res, . 67(17):7945-7 (2007).
Cheng, et al., "Cutting edge: TLR2 is a functional receptor for acute-phase serum amyloid A", J Immunol, 181 (1), 2216 (2008).
Chia, et al., "Prognostic significance of a novel hypoxia-regulated marker, carbonic anhydrase IX, in invasive breast carcinoma", J Clin Oncol 19:3660-8 (2001).
Cho and Celis, "Optimized peptide vaccines eliciting extensive CD8 T-cell responses with therapeutic antitumor effects", Cancer Res, 69 (23):9012-9 (2009).
Colpaert, et al., "The presence of a fibrotic focus in invasive breast carcinoma correlates with the expression of carbonic anhydrase IX and is a marker of hypoxia and poor prognosis", Breast Cancer Res Treat, 81:137-47 (2003).
Czarniecki, "Small molecule modulators of toll-like receptors", J Med Chem, 51 (21): 6621-6 (2008).
D'Agostini, et al., Antitumour effect of OM-174 and cyclophosphamide on murine B16 melanoma in different experimental conditions, Int Immunopharmacol, 5 (7-8), 1205-12 (2005).
De Ridder, et al., "The radiosensitizing effect of immunoadjuvant OM-174 requires cooperation between immune and tumor cells through interferon-gamma and inducible nitric oxide synthase", Int J Radiat Oncol Biol Phys, 66 (5):1473-80 (2006).
Douglas-Jones, et al., "Molecular assessment of sentinel lymph node in breast cancer management", Histopathology 55:107-113 (2009).
Esposito, et al., "Most pancreatic cancer resections are R1 resections", Ann Surg Oncol, 15 (6), 1651-60 (2008).
Ferrone, et al., "Pancreatic adenocarcinoma: the actual 5-year survivors", J Gastrointest Surg, 12 (4), 701-6 (2008).
Fujimoto, et al., "Lipopeptides from *Staphylococcus aureus* as Tlr2 Ligands: prediction with mrna expression, chemical synthesis, and immunostimulatory activities" Chembiochem, 10 (14), 2311-5 (2009).
Galanzha, et al., "In vivo fiber-based multicolor, photoacoustic detection and photothermal purging of metastasis in sentinel lymph nodes targeted by nanoparticles", J Biophotonics 2:528-39 (2009).
Garay, et al., "Cancer relapse under chemotherapy: why TLR2/4 receptor agonists can help", Eur J Pharmacol, 563 (1-3):1-17 (2007).
Giuliano, et al., "Lymphatic mapping and sentinel lymphadenectomy for breast cancer", Annals of Surgery 220:391-401 (1994).
Goonewardene, et al., "Hypoxia-induced pathways in breast cancer", Microsc Res Tech., 59:41-8 (2002).
Guevara-Patino, et al., "Optimization of a self antigen for presentation of multiple epitopes in cancer immunity", J Clin Invest, . 116(5):1382-90 (2006).
Hadjipanayis, et al., "Current and future clinical applications for optical imaging of cancer: from intraoperative surgical guidance to cancer screening", Semin Oncol, 38 (1), 109-18 (2011).

Handl, et al., "Lanthanide-based time-resolved fluorescence of in cyto ligand-receptor interactions", Anal Biochem, 330 (2):242-50 (2004).
Handl, et al., "Development of a lanthanide-based assay for detection of receptor-ligand interactions at the delta-opioid receptor", Anal Biochem, 343 (2):299-307 (2005).
Hennessy, et al., "Targeting Toll-like receptors: emerging therapeutics", Nat Rev Drug Discov 9 (4):293-307 (2010).
Howard, et al., "A margin-negative R0 resection accomplished with minimal postoperative complications is the surgeon's contribution to long-term survival in pancreatic cancer", J Gastrointest Surg, 10 (10), 1338-45; discussion 1345-6 (2006).
Hussain, et al., "Hypoxia-regulated carbonic anhydrase IX expression is associated with poor survival in patients with invasive breast cancer", Br J Cancer, 96:104-9 (2007).
Ivanov, et al., "Expression of hypoxia-inducible cell-surface transmembrane carbonic anhydrases in human cancer", Am J Pathol., 158:905-19 (2001).
Janeway and Medzhitov, "Innate immune recognition", Annu Rev Immunol, 20:197-216 (2002).
Jarnicki, et al., "Attenuating regulatory T cell Induction by TLR agonists through inhibition of p38 MAPK signaling in dendritic cells enhances their efficacy as vaccine adjuvants and cancer immunotherapeutics", Journal of immunology, 180 (6), 3797-806 (2008).
Jin, et al, "Crystal structure of the TLR1-TLR2 heterodimer induced by binding of a tri-acylated lipopeptide", Cell, 130 (6), 1071-82 (2007).
Jin and Lee, "Structures of the toll-like receptor family and its ligand complexes", Immunity, 29(2):182-91(2008).
Josan, et al., "Solid-phase synthetic strategy and bioevaluation of a labeled delta-opioid receptor ligand Dmt-Tic-Lys for in vivo imaging", Org Lett, 11 (12):2479-82 (2009).
Kang,et al., "Recognition of lipopeptide patterns by Toll-like receptor 2-Toll-like receptor 6 heterodimer", Immunity, 31 (6), 873-84 (2009).
Kanzler, et al., "Therapeutic targeting of innate immunity with Toll-like receptor agonists and antagonists", Nat Med, 13(5):552-9 (2007).
Kawai and Akira, "The role of pattern-recognition receptors in innate immunity: update on Toll-like receptors", Nat Immunol., 11 (5):373-84 (2010).
Keereweer, et al., "Translational optical imaging in diagnosis and treatment of cancer", Curr Pharm Biotechnol.,13(4):498-503 (2012).
Kimbrell, et al., "Comparison of the immunostimulatory and proinflammatory activities of candidate Gram-positive endotoxins, lipoteichoic acid, peptidoglycan, and lipopeptides, in murine and human cells", Immunol Lett, 118(2):132-41 (2008).
Krag, et al., "The sentinel node in breast cancer—a multicenter validation study", N Engl J Med., 339:941-6 (1998).
Krag, et al., "Technical outcomes of sentinel-lymph-node resection and conventional axillary-lymph-node dissection in patients with clinically node-negative breast cancer: results from the NSABP B-32 randomised phase III trial", Lancet Oncol 8:881-8 (2007).
Krag, et al., "Surgical resection and radiolocalization of the sentinel lymph node in breast cancer using a gamma probe", Surg Oncol 2:335-340 (1993).
Krchnak and Vagner, "Color-monitored solid-phase multiple peptide synthesis under low-pressure continuous-flow conditions", Pept Res., 3 (4):182-93 (1990).
Krchnak, et al., "Noninvasive continuous monitoring of solid-phase peptide synthesis by acid-base indicator", Int J Pept Protein Res., 32 (5):415-6 (1988).
Lancashire, et al., "A validated gene expression profile for detecting clinical outcome in breast cancer using artificial neural networks", Breast Cancer Res Treat., 120:83-93 (2010).
Li, et al., "Expression and activity of carbonic anhydrase IX is associated with metabolic dysfunction in MDA-MB-231 breast cancer cells", Cancer Invest 27:613-23 (2009).
Manavalan, et al., "Similar Structures but Different Roles—An Updated Perspective on TLR Structures", Front Physiol, 2:41(2011).

(56) References Cited

OTHER PUBLICATIONS

Manukyan, et al., "Binding of lipopeptide to CD14 induces physical proximity of CD14, TLR2 and TLR1", Eur J Immunol., 35 (3):911-21 (2005).
Marshall, et al., "Immunotherapy with PI3K inhibitor and Toll-like receptor agonist induces IFN-$^3$+IL-17+ polyfunctional T cells that mediate rejection of murine tumors.", Cancer Res., 72 (3): 581-91(2012).
McElroy, et al., "Fluorescent LYVE-1 antibody to image dynamically lymphatic trafficking of cancer cells in vivo", J Surg Res., 151:68-73 (2009).
McMasters, et al., "Sentinel lymph node biopsy for breast cancer: a suitable alternative to routine axillary dissection in multi-institutional practice when optimal technique is used", J Clin Oncol., 18:2560-6 (2000).
Metzger, et al., "Synthesis of N alpha-Fmoc protected derivatives of S-(2,3-dihydroxypropyl)-cysteine and their application in peptide synthesis", Int J Pept Protein Res, 38 (6), 545-54 (1991).
Mizuno, et al., "A novel peptidoglycan-associated lipoprotein found in the cell envelope of Pseudomonas aeruginosa and *Escherichia coli*", J Biochem, 86 (4):991-1000 (1979).
Morr, et al., "Differential recognition of structural details of bacterial lipopeptides by toll-like receptors", Eur J Immunol., 32 (12):3337-47 (2002).
Morse, et al., "Identification of novel pancreatic adenocarcinoma cell-surface targets by gene expression profiling and tissue microarray", Biochem Pharmacol, 80 (5):748-54 (2010).
Morse, et al., "Determining suitable internal standards for mRNA quantification of increasing cancer progression in human breast cells by real-time reverse,tanscriptase polymerase chain reaction", Anal Biochem., 342:69-77 (2005).
Muhlradt, et al., "Structure and specific activity of macrophage-stimulating lipopeptides from Mycoplasma hyorhinis", Infect Immun., 66 (10):4804-10 (1998).
Muhlradt, et al., "Isolation, structure elucidation, and synthesis of a macrophage timulatory lipopeptide from Mycoplasma fermentans acting at picomolar concentration", J Exp Med., 185 (11):1951-8 (1997).
Murata, "Activation of Toll-like receptor 2 by a novel preparation of cell wall skeleton from *Mycobacterium bovis* BCG Tokyo (SMP-105) sufficiently enhances Immune responses against tumors", Cancer Sci, 99 (7):1435-40 (2008).
Nguyen, et al., "Surgery with molecular fluorescence imaging using activatable cell-penetrating peptides decreases residual cancer and improves survival", PNAS, 107 (9):4317-22 (2010).
Ntziachristos, et al., "Current concepts and future perspectives on surgical optical imaging in cancer", J biomed Optic, 15 (6):066024 (2010).
Ozinsky, et al., "The repertoire for pattern recognition of pathogens by the innate immune system is defined by cooperation between toll-like receptors", PNAS, 97 (25):13766-71 (2000).
Prass, et al., "Lipopeptides of the N-terminus of *Escherichia coli* lipoprotein: synthesis, mitogenicity and properties in monolayer experiments", Biochim Biophys Acta, 900(1):116-28 (1987).
Purushotham, et al., "Morbidity after sentinel, lymph node biopsy in primary breast cancer: results from a randomized controlled trial", J Clin Oncol., 23:4312-21 (2005).
Reichel, et al., "Stereochemical Dependence of the Self-Assembly of the Imunoadjuvants Pam3Cys-Ser and Pam3Cys-Ser", J Am Chem Soc, 121 (35):7989-97 (1999).
Robey, et al., "Hypoxia-inducible factor-1alpha and the glycolytic phenotype in tumors", Neoplasia., 7:324-30 (2005).
Salunke, et al., "Structure-activity relationships in human Toll-like receptor 8-active 2,3-diamino-furo[2,3-c]pyridines", J Med.Chem., 55(18):8137-51 (2012a).
Salunke, et al., "Structure-activity relationships in human Toll-like receptor 2-specific monoacyl lipopeptides", J Med.Chem., 55(7):3353-63 (2012b).

Schindler and Baichwal, "Three NF-kappa B binding sites in the human E-selectin gene required for maximal tumor necrosis factor alpha-induced expression", Mol Cell Biol, 14 (9):5820-31 (1994).
Schlauder, et al., "Assessment of muscarinic and nicotinic acetylcholine receptor expression in primitive neuroectodermal tumor/ewing family of tumor and desmoplastic small round cell tumor: an immunohistochemical and Western blot study of tissue microarray and cell lines", Fetal Pediatr Pathol., 27:83-97 (2008).
Seifert, et al., "Activation of superoxide formation and lysozyme release in human neutrophils by the synthetic ilpopeptlde Pam3Cys-Ser-(Lys)4. Involvement of guanine-nuoleotide-binding proteins and synergism with chemotactic peptides", Biochem J, 267(3):795-802 (1990).
Sevick-Muraca, et al., "Imaging of lymph flow in breast cancer patients after microdose administration of a near-infrared fluorophore: feasibility study", Radiology, 246 (3):734-41(2008).
Sharma, et al., "Gold-Speckled Multimodal Nanoparticles for Non-invasive Bioimaging", Chem Mater., 20:6087-94 (2008).
Simons, et al., "Role of neutrophils in BCG immunotherapy for bladder cancer", Urol Oncol, 26 (4):341-5(2008).
Span, et al., "Carbonic anhydrase-9 expression levels and prognosis in human breast cancer: association with treatment outcome", Br J Cancer, 89:271-276 (2003).
Stacker, et al., Lymphangiogenesis and cancer metastasis\, Nat Rev Cancer, 2:573-83 (2002).
Stummer, et al., "Fluorescence-guided surgery with 5-aminolevulinic acid for resection of malignant glioma: a randomised controlled multicentre phase III trial", Lancet Oncol, 7(5), 392-401(2006).
Supuran, et al., "Carbonic anhydrases as targets for medicinal chemistry", Bioorg Med Chem., 15:4336-4350 (2007).
Tafreshi, et al., "Molecular and functionalimaging of breast cancer", Cancer Control, 17:143-55 (2010).
Tagaya, et al., "Intraoperative identification of sentinel lymph nodes by near-infrared fluorescence imaging in patients with breast cancer", Am J Surg, 195 (6):850-3 (2008).
Takeda, et al., "Toll-like receptors", Annul Rev Immunol, 21:335-76 (2003).
Takeuchi, et al., "Discrimination of bacterial lipoproteins by Toll-like receptor 6", Int Immunol, 13 (7), 933-40 (2001).
Takeuchi, et al., "Cutting edge: role of Toll-like receptor 1 in mediating immune response to microbial lipoproteins", J Immunol, 169(1):10-4 (2002).
Trastour, et al., "HIF-1alpha and CA IX staining in invasive breast carcinomas: prognosis and treatment outcome", Int J Cancer, 120:1451-8 (2007).
Uhlar and Whitehead, "Serum amyloid A, the major vertebrate acute-phase reactant", Eur J Biochem, 265(2):501-23 (1999).
Ung, et al., "Australasian experience and trials in sentinel lymph node biopsy: the RACS SNAC trial", Asian J Surg., 27:284-90 (2004).
Vagner, et al., "Heterobivalent ligands crosslink multiple cell-surface receptors: the human melanocortin-4 and delta-opioid receptors", Angew Chem Int Ed Engl, 47 (9):1685-8 (2008).
Van Dam, et al., "Intraoperative tumor-specific fluorescence imaging in ovarian cancer by folate receptor-a targeting: first in-human results", Nature medicine, 17 (10):1315-9 (2011).
West, et al., "Recognition and signaling by toll-like receptors", Annu Rev Cell Dev Biol., 22:409-37 (2006).
Wu, et al., "Structure-activity relationships in toll-like receptor-2 agonistic diacylthioglycerol lipopeptides", J Med Chem. 53(8):3198-213 (2010).
Xu, et al., "Enhanced targeting with heterobivalent ligands", Mol Cancer Ther., (8):2356-65 (2009).
Yamamoto, et al., "Current views of toll-like receptor signaling pathways", Gastroenterol Res Pract., 2010(24365):1-8 (2010).
Zhang, et al., "TLR1/TLR2 agonist induces tumor regression by reciprocal modulation of effector and regulatory T cells", J Immunology, 186(4):1963-9 (2011).
Zlotnick, et al., "Purification and characterization of a peptidoglycan-associated lipoprotein from Haemophilus influenza", J Biol Chem, 263(20):9790-4 (1988).

(56) References Cited

OTHER PUBLICATIONS

Zuany-Amorim, et al., "Toll-like receptors as potential therapeutic targets for multiple diseases", Nat Rev Drug Discov, 1(10):797-807 (2002).

* cited by examiner

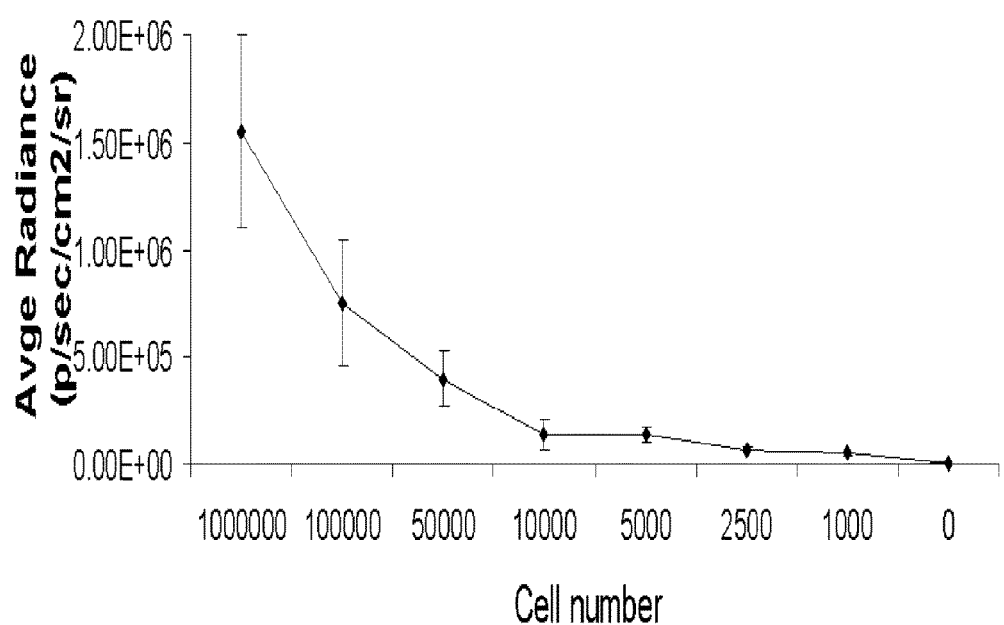

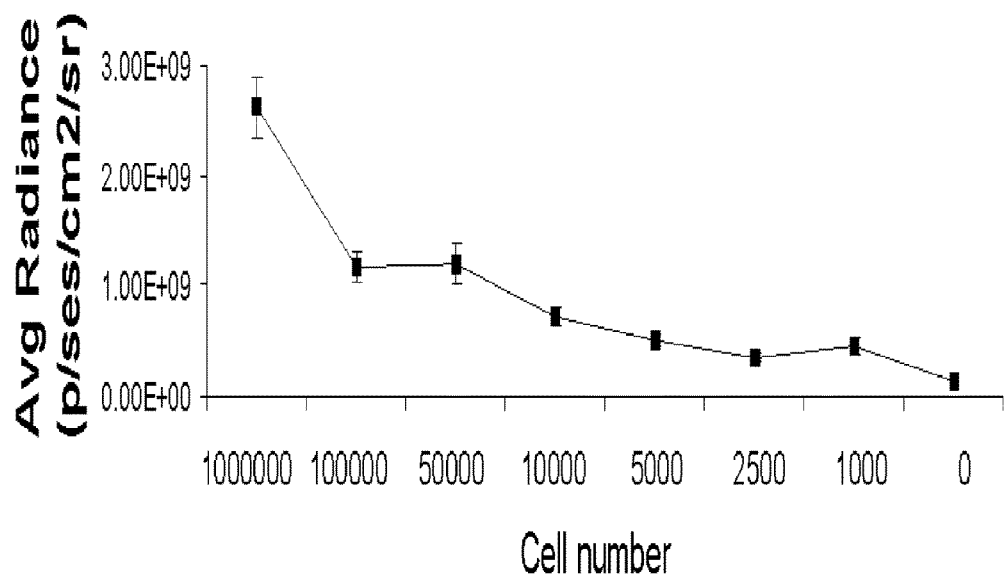

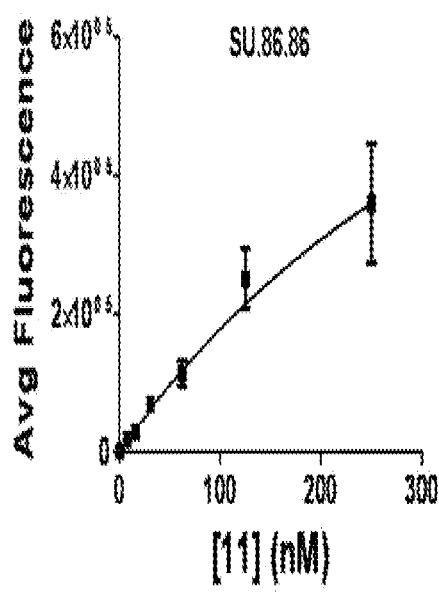 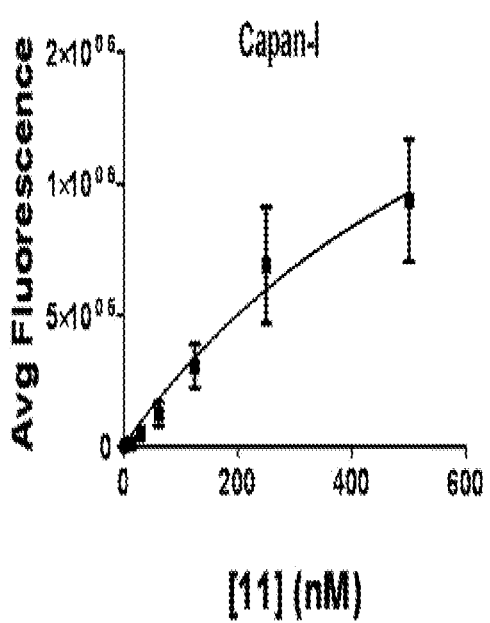
Figure 21A
Figure 21B

MOLECULAR IMAGING OF CANCER CELLS IN VIVO

CROSS REFERENCE TO RELATED APPLICATIONS

This application is a 371 application of International Application No. PCT/US2012/053813, filed Sep. 5, 2012, which claims the benefit of and priority to U.S. Provisional Application No. 61/533,198, filed Sep. 10, 2011. International Application No. PCT/US2012/053813, filed Sep. 5, 2012, and U.S. Provisional Application No. 61/533,198, filed Sep. 10, 2011, are hereby incorporated herein by reference in their entirety.

STATEMENT REGARDING FEDERALLY SPONSORED RESEARCH

This invention was made with government support under Agreements R01 CA97360, R01 CA123547, R01 CA103921, and R01 CA136828 awarded by the National Institutes of Health (NIH). The government has certain rights in the invention.

REFERENCE TO SEQUENCE LISTING

The Sequence Listing submitted Feb. 21, 2014, as a text file named "MOF_11MB064_PCT_AMD_AFD_Sequence_Listing.txt," created on Feb. 21, 2014, and having a size of 3,273 bytes is hereby incorporated by reference pursuant to 37 C.F.R. § 1.52(e)(5).

FIELD OF THE INVENTION

This invention is generally related to cancer screening. More specifically, this invention relates to the use of targeted molecular imaging to detect cancer in vivo.

BACKGROUND OF THE INVENTION

Around most small cancers there is an area where microscopic sized cancers cells have spread out or migrated. Normally a surgeon tries to remove the tumor with a rim of normal tissue so that he is sure of removing these small cells as well. If cancer cells are found right up to the edge of the resected tissue, this is referred to as having cancer at the margin (or positive margins). Cancer patients have a reduced chance of cancer recurrence if resection margins are negative. Current techniques to assess surgical margins involve post-operative evaluation of pathology specimens collected during surgery. If the pathology specimen is positive, additional surgery may be required. Therefore, a method to intraoperative assess the resection margin prior to actual resection will minimize the chance of a positive microscopic margin and minimize the need for additional surgery.

In addition, determining the presence or absence of axillary lymph nodal metastasis is critical to the pathologic staging, prognostication and guidance of treatment in patients with certain cancers, such as breast cancer (Stacker, S. A., et al. *Nat Rev Cancer* 2:573-583 (2002); Tafreshi, N. K., et al. *Cancer Control* 17:143-155 (2010)). The sentinel lymph node (SLN) is the axillary node that first receives drainage from the breast parenchyma in the area of the primary tumor and, therefore has the highest probability of containing metastatic cells. SLNs can be identified by a surgical application referred to as intraoperative lymphatic mapping (ILM or SLN mapping). ILM helps trace the lymphatic drainage patterns in a cancer patient to evaluate potential tumor drainage and cancer spread in lymphatic tissue. The ILM technique does not detect cancer; rather it helps surgeons identify the lymph node(s) to which a tumor is likely to drain and spread. ILM involves peritumoral injection of a radioactive tracing agent to identify SLNs, which are then biopsied for pathological examination (Albertini, J. J., et al. *JAMA* 276:1818-1822 (1996); Giuliano, A. E. et al. *Annals of Surgery* 220:391-401 (1994); Krag, D. N. et al. *Surg Oncol* 2:335-340 (1993)). The sulfer colloid of technetium 99m ($^{99m}$Tc) is a radioactive tracing agent particularly suited for ILM. Moreover, the radioactive tracing agent Lymphoseek® (Tilmanocept) described in U.S. Pat. No. 6,409,990 is designed to accumulate in lymphatic tissue by specifically binding to mannose binding receptor (MBR; CD206) proteins that reside on the surface of resident dendritic cells and macrophages. If biopsied SLNs are negative for cancer, then complete axillary lymph node dissection can be avoided (Douglas-Jones, A. G. et al. *Histopathology* 55:107-113 (2009)).

However, a limitation of ILM techniques is the lack of biomarkers for targeting these agents to cancer cells. Instead, such agents distribute non-specifically across SLNs providing only an anatomic and non-functional map (Galanzha, E. I. et al. *J Biophotonics* 2:528-539 (2009); McElroy, M. et al. *J Surg Res* 151:68-73 (2009)). As a result, SLN biopsy is required to identify potential cancer cells. SLN biopsy is an invasive surgical procedure, requiring a multidisciplinary team with specialized imaging and surgical equipment (Douglas-Jones, A. G. et al. *Histopathology* 55:107-113 (2009); Krag, D. et al. *N Engl J Med* 339:941-946 (1998); McMasters, K. M. et al. *J Clin Oncol* 18:2560-2566 (2000); Ung, O. A. et al. *Asian J Surg* 27:284-290 (2004)), and may have postoperative complications, such as lymphedema, seroma formation, sensory nerve injury, and limitation in range of motion (Purushotham, A. D. et al. *J Clin Oncol* 23:4312-4321 (2005)). The majority of breast cancer patients (74%) who undergo SLN biopsy are pathologically negative (Krag, D. N. et al. *Lancet Oncol* 8:881-888 (2007)). Moreover, biopsies fail to identify axillary disease in 5-10% of patients (McMasters, K. M. et al. *J Clin Oncol* 18:2560-2566 (2000); Ung, O. A. et al. *Asian J Surg* 27:284-290 (2004)). Therefore, a non-invasive method for detecting cancer with improved sensitivity and specificity and eliminating unnecessary surgeries is warranted.

It is an object of the invention to provide compositions and methods for non-invasive detection of cancer in a subject.

It is a particular object of the invention to provide compositions and methods for in vivo molecular imaging of cancer cells, such as metastatic cancer cells and pancreatic cancer cells, in a subject.

It is a further object of the invention to provide compositions and methods for label-guided surgery for cancer.

It is a particular object of the invention to provide compositions and methods for label-guided surgery for pancreatic cancer.

It is a further object of the invention to provide cell-surface markers that can be used to detect cancer cells in vivo.

It is a particular object of the invention to provide cell-surface markers that can be used to detect pancreatic cancer cells in vivo.

SUMMARY OF THE INVENTION

A non-invasive method for detecting cancer cells in a subject in vivo has been developed. The method generally involves administering to the subject one or more targeted imaging probes that each specifically binds a cellular target selected from the group consisting of carbonic anhydrase 9 (CAIX), carbonic anhydrase 12 (CAXII), mammaglobin-A, carcinoembryonic antigen-related cell adhesion molecule 6 (CEACAM6), C—X—C motif chemokine 10 (CXCL10), and matrix metallopeptidase 9 (MMP-9). The subject can then be imaged with a molecular imaging device to detect the targeted imaging probe(s) in the subject. With this method, detection of the targeted imaging probe(s) in an organ or tissue of a subject can be an indication of cancer cells in the organ.

The cancer cells can be primary tumors or metastasized cancer cells. Therefore, in some embodiments, the method involves administering targeted imaging probes to a subject diagnosed with a primary tumor to identify metastasized cancer cells. In other embodiments, the method involves administering targeted imaging probes to a subject at risk of cancer to detect primary or occult tumors. Non-limiting examples of cancer cells that can be detected by the disclosed methods include breast cancer cells and non small-cell carcinoma cells.

In preferred embodiments, the cellular target can be CAIX and CAXII. The combination of these cellular targets has been shown to identify 100% of lymph node metastasis from patients with breast cancer. In these embodiments, the method can involve administering to the subject a first targeted imaging probe that specifically binds CAIX and a second targeted imaging probe that specifically binds CAXII, wherein detection of either the first targeted imaging probe or the second targeted imaging probe in an organ of a subject is an indication of cancer cells in the organ.

Mammaglobin-A has also been shown to identify malignant breast cancer cells in breast and lymph nodes. Therefore, in some embodiments, the cellular target is mammaglobin-A. In these embodiments, the method can involve administering to the subject a targeted imaging probe that specifically binds mammaglobin-A, wherein detection of the targeted imaging probe that specifically binds mammaglobin-A in an organ of a subject is an indication of breast cancer cells in the organ.

Devices for use in molecular imaging are known in the art and include, for example, devices for magnetic resonance imaging (MRI), optical imaging, computed tomography (CT), and nuclear medicine imaging. Such devices can be used in the disclosed methods. In preferred embodiments, the molecular imaging device is an optical imaging device that can detect near-infrared light.

In preferred embodiments, the antibodies can be monoclonal antibodies, or fragments thereof that bind the cellular targets. Monoclonal antibodies that specifically bind CAIX, CAXII, mammaglobin-A, CEACAM6, CXCL10, and MMP-9 in vivo are known and commercially available. Moreover, additional antibodies suitable for in vivo detection can be produced using routine methods. In some embodiments, the antibodies or antibody fragments can be chimeric, humanized, human, recombinant, etc.

The targeted imaging probe that specifically binds CAIX preferably contains an antibody having the idiotype of monoclonal antibody clone 303123 linked to a detectable label. The targeted imaging probe that specifically binds CAXII preferably contains an antibody having the idiotype of monoclonal antibody clone 315602 linked to a detectable label. The targeted imaging probe that specifically binds mammaglobin-A preferably contains an antibody having the idiotype of monoclonal antibody clone 304-1A5 or clone 31A5 linked to a detectable label. Therefore, in some embodiments, the targeted imaging probe contains monoclonal antibody clone 303123, clone 315602, clone 304-1A5, or clone 31A5.

The targeted imaging probe is preferably an antibody linked to a detectable label. Suitable detectable labels can be selected based upon the devices used in molecular imaging. In preferred embodiments, the detectable label is a near-infrared (NIR) fluorophore for use with optical imaging. Therefore, the method preferably involves, for example, a first antibody having the idiotype of monoclonal antibody clone 303123 linked to a first NIR fluorophore and a second antibody having the idiotype of monoclonal antibody clone 315602 linked to a second NIR fluorophore.

Also provided is a composition containing a first antibody having the idiotype of monoclonal antibody clone 303123 linked to a first NIR fluorophore and a second antibody having the idiotype of monoclonal antibody clone 315602 linked to a second NIR fluorophore. The composition can further contain a third antibody having the idiotype of monoclonal antibody clone 304-1A5 or clone 31A5 linked to a third NIR fluorophore. Therefore, the composition can contain monoclonal antibody clone 303123, clone 315602, clone 304-1A5, clone 31A5, or any combination thereof. The detectable labels on different targeted imaging probes, for example, can be, the same or different, can have the same, similar, or different excitation and/or emission frequencies, or a combination. For example, different targeted imaging probes that specifically bind different cellular targets can have detectable labels that allow the different targeted imaging probes to be distinguished when imaged, not distinguished when imaged, or a combination (when, for example, three of more targeted imaging probes are used).

A kit is also provided that contains two or more antibodies that specifically bind a cellular target selected from the group consisting of CAIX, CAXII, mammaglobin-A, CEACAM6, CXCL10, and MMP-9 in two or more containers, wherein at least a first antibody is linked to a first NIR fluorophore and at least a second antibody is linked to a second NIR fluorophore. In preferred embodiments, light in either the absorption or emission spectrum of the first NIR fluorophore does not excite the second NIR fluorophore. At least one of the two or more antibodies is preferably monoclonal antibody clone 303123, 315602, or a combination thereof. The kit can also contain monoclonal antibody clone 304-1A5 or clone 31A5.

BRIEF DESCRIPTION OF THE DRAWINGS

FIG. 8A is a graphs showing bioluminescence (average radiance (photons/sec/cm²/steradian)) of ZR-75.1/luc cells injection into MFP of ALN estrogen-pelleted mice as a function of the number of cells injected (1,000,000, 100,000, 10,000, 5,000, 1,000, or 0). FIG. 8B is a graph showing fluorescence (average radiance photons/sec/cm²/steradian) 24 hours after injection of MamAb-680 into MFP of the mice of FIG. 8A as a function of the number (1,000,000, 100,000, 10,000, 5,000, 1,000, or 0) of ZR-75.1/luc cells injected into ALN. All data represent mean±s.d. of pixel values within the ROIs.

FIGS. 21A and 21B show saturation binding analysis of Eu-DTPA-labeled compound 11 to TLR2. The saturation binding curves show TLR2 specific binding (total—nonspecific) curves of 11 to TLR2 using the following TLR2-expressing cancer cell lines: A) SU.86.86 with a K$_d$ of 74 nM and B$_{max}$ of 269,878 AFU (n=3 assays, R$^2$ values>0.99) and B) Capan-I with a K$_d$ of 78 nM and B$_{max}$ of 951,170 AFU (n=3 assays, R2 values>0.96).

DETAILED DESCRIPTION OF THE INVENTION

I. Definitions

Figure 1A:
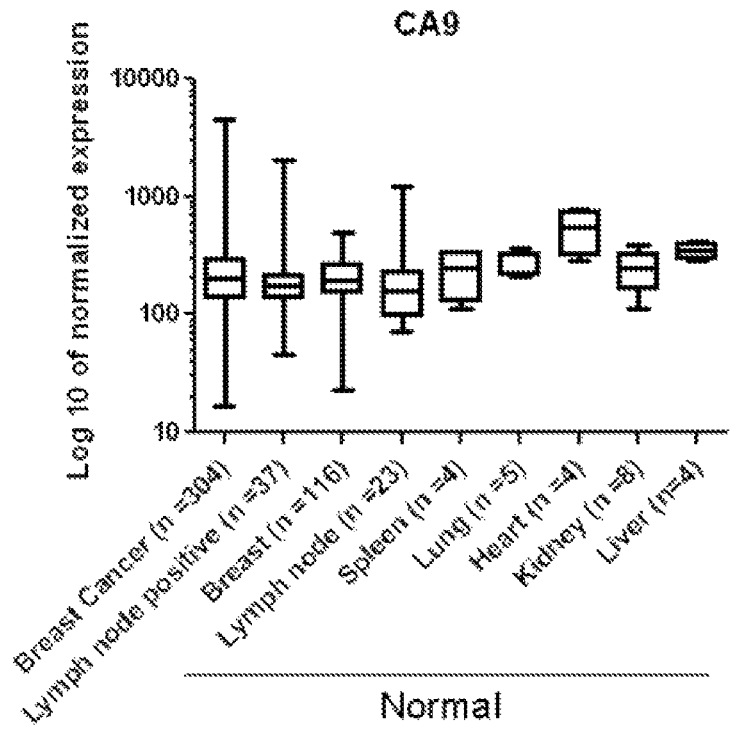
FIGS. 1A and 1B are bar graphs showing CA9 (FIG. 1A) and CA12 (FIG. 1B) mRNA expression ($\log_{10}$ of normalized expression) in breast cancer, lymph node positive, breast, lymph node, spleen, lung, heart, kidney, and liver samples. Data are represented as mean±s.d.
Figure 1B:
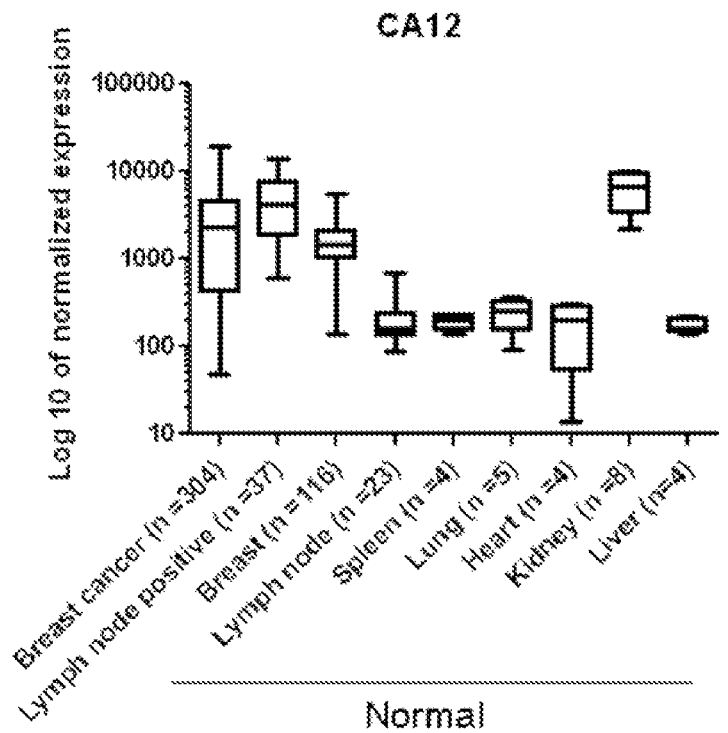

The term "targeted molecular imaging" refers to the in vivo detection of a biological process, such as biodistribution, at the cellular and molecular level. The in vivo detection is accomplished using a targeted imaging probe that specifically binds a molecular or cellular target and an imaging device that detects the probe in vivo.

The term "targeted imaging probe" refers to a molecule that specifically binds to a molecular or cellular target in vivo that can be detected using in vivo imaging techniques. Detection is generally accomplished by linking the binding molecule to a detectable label. Preferred binding molecules include antibodies, peptides, peptidomimetics, and small molecules.

The term "antibody" refers to a polyclonal, monoclonal, recombinant, or synthetic immunoglobulin molecule that specifically binds a target antigen. The term includes intact immunoglobulin molecules, fragments or polymers of those immunoglobulin molecules, chimeric antibodies containing sequences from more than one species, class, or subclass of immunoglobulin, and human or humanized versions of immunoglobulin molecules or fragments thereof containing a least the idiotype of an immunoglobulin that specifically binds the target antigen.

The term "idiotype" refers to the portion of an immunoglobulin molecule that confers the molecule's ability to bind an antigen. The idiotype of an antibody is determined by the complementarity determining regions (CDRs) of the immunoglobulin variable domains (V$_L$ and V$_H$).

The term "peptide" can be used to refer to a natural or synthetic molecule comprising two or more amino acids linked by the carboxyl group of one amino acid to the alpha amino group of another. The peptide is not limited by length; thus "peptide" can include polypeptides and proteins.

The term "peptidomimetic" refers to a mimetic of a peptide which includes some alteration of the normal peptide chemistry. Peptidomimetics typically enhance some property of the original peptide, such as increase stability, increased efficacy, enhanced delivery, increased half life, etc.

The term "aptamer" refers to oligonucleic acid molecules that specifically bind to a target molecule.

As used herein, the term "small molecule" refers to a compound having a molecular weight of less than 1000 Daltons, and typically between 300 and 700 Daltons. The term may include monomers or primary metabolites, secondary metabolites, a biological amine, a steroid, or synthetic or natural, non-peptide biological molecule(s). In the context of targeted imaging probes that are small molecules, the small molecule can specifically bind the molecular or cellular target.

The term "specifically binds" refers to the binding of a molecule to a target molecule, such as an antibody to its cognate antigen, while not significantly binding to other molecules. Preferably, a molecule "specifically binds" to a target molecule with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with the target molecule.

The term "neoplasm" refers to a cell undergoing abnormal cell proliferation. The growth of neoplastic cells exceeds and is not coordinated with that of the normal tissues around it. The growth typically persists in the same excessive manner even after cessation of the stimuli, and typically causes formation of a tumor. Neoplasms may be benign, premalignant, or malignant.

The term "cancer" or "malignant neoplasm" refers to a cell that displays uncontrolled growth, invasion upon adjacent tissues, and often metastasizes to other locations of the body.

The term "metastatic" or "metastasized" refer to cancer cells that have spread from the site of origin (primary site) to a distant location (metastatic site) in the body.

The term "occult tumor" refers to metastasized cancer cells with unknown primary origin.

The term "subject" or "patient" refers to any individual who is the target of administration. The subject can be a vertebrate, for example, a mammal. Thus, the subject can be a human. The subject can be domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. The term does not denote a particular age or sex.

The term "effective amount" refers to an amount of targeted imaging probes sufficient for in vivo detection of the probes in an organ or a tissue by an imaging device. The exact amount required will vary from subject to subject, depending on the age, and general condition of the subject, the organ or tissue that is being imaged, the particular probes used, and its mode of administration. An appropriate "effective amount" can be determined by one of ordinary skill in the art using only routine experimentation.

The term "detectable label" as used herein refers to any molecule that can be detected by in vivo imaging techniques, such as a fluorescent molecule, a metal (e.g., gold), or a radioactive isotope.

The term "near-infrared (NIR) fluorophore" refers to a molecule that has an absorption and emission wavelength in the NIR spectrum between 680 and 900 nm. NIR molecular probes work in a preferential wave range for in vivo fluorescence imaging called "biological window." These molecules can be detected deeper while minimizing the absorption of the fluorescence by tissues.

The terms "label-guided surgery," "fluorescent-guided surgery," and the like, refer to surgery where the location of relevant tissue and/or cells is marked by a label, such a fluorescent label, where the label is visible during surgery (this is intraoperative imaging). Label-guided surgery where the label is visualized via an image of tissue and/or cells can be referred to as image-guided-surgery.

II. Compositions

A. Targeted Imaging Probes

Targeted imaging probes for detecting cancer cells are provided that specifically bind cellular targets on cancer cells in vivo. In general, the cellular targets can be proteins exposed on the surface of cancer cells and the imaging probes are able to access and bind these targets in vivo. The disclosed targeted imaging probes preferably do not bind normal (non-cancerous) tissue. In some embodiments, the targeted imaging probes bind metastasized cancer cells or cells about to undergo metastasis from the primary tumor.

Probes that specifically bind carbonic anhydrase 9 (CAIX), carbonic anhydrase 12 (CAXII), mammaglobin-A, carcinoembryonic antigen-related cell adhesion molecule 6 (CEACAM6), C—X—C motif chemokine 10 (CXCL10), and matrix metallopeptidase 9 (MMP-9) in vivo are disclosed for use in detecting cancer cells, such as metastasized cancer cells. Targeted imaging probes preferably bind the cellular targets in regions that are accessible from the circulation (e.g., blood or lymph) in vivo.

Targeted imaging probes specifically binding CAIX and CAXII are preferably used together to detect cancer cells expressing either or both of these proteins. These probes can also be used in combination with other tissue specific probes to enhance specificity. For example, CAIX and CAXII probes are preferably used in combination with probes that specifically bind mammaglobin-A to detect metastasized breast cancer cells.

Probes that specifically bind Toll-like receptor 2 (TLR2) in vivo are disclosed for use in detecting cancer cells, such as pancreatic cancer, pancreatic cancer cells, and metastasized pancreatic cancer cells.

In some embodiments, the disclosed targeted imaging probes are used in combination with other targeting agents, such as other cancer-specific targeting imaging probes. As an example, a targeting agent that specifically binds tumor-associated glycoprotein-72 (TAG-72) is disclosed for use in combination with the disclosed targeted imaging probes. TAG-72 is a glycoprotein found on the surface of many cancer cells, including breast, colon, and pancreatic cells. Murine monoclonal antibody (CC49 MAb, Minretumomab) specifically binds TAG-72 and has strong reactivity with both LS-174T colon cancer extract and to a breast cancer extract.

The targeted imaging probes generally can contain a cellular target binding domain and a detectable label. The cellular target binding domain and detectable label can be linked using routine methods.

In some embodiments, the cellular target binding domain and detectable label can be chemically crosslinked using protein cross-linking agents. Commercially available labels, such as fluorophores generally contain crossing linking agents (such as a succinimidyl ester) for conjugation to proteins, such as antibodies. Non-limiting examples of suitable protein crosslinkers include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl] sulfone), BSOCOES (Bis[2-(succinimdooxycarbonyloxy) ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis (sulfosuccinimidylsuccinate)), DPDPB (1,2-Di[3'-(2'-pyridyldithio)propionamido]butane), BSSS (Bis (sulfosuccinimdyl)suberate), SMPB (Succinimdyl-4-(p-maleimidophenyl)butyrate), SULFO SMPB (Sulfosuccinimdyl-4-(p-maleimidophenyl)butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio)propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS(N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), and DMA (Dimethyladipimidate hydrochloride).

In other embodiments, the targeted imaging probe can be a fusion peptide or protein containing the cellular target binding domain and a detectable label. Fusion are proteins created through the joining of two or more genes or coding regions that originally coded (and/or were designed to code for) for separate peptides or proteins. Translation of this fusion gene or coding region results in a single peptide or polypeptide with functional properties derived from each of the original peptide or proteins. Recombinant fusion peptide or proteins can be created artificially by recombinant DNA technology. This typically involves removing the stop codon from a cDNA sequence coding for the first peptide or protein, then appending the cDNA sequence of the second peptide or protein in frame through ligation or overlap extension PCR. Alternatively, the coding regions can be synthesized and then joined or can even be synthesized as a fusion coding region. The resulting fusion DNA sequence can then be expressed by a cell as a single peptide or protein. The protein can be engineered to include the full sequence of both original peptides or proteins, or only a portion of either. If the two entities are proteins, often linker (or "spacer") peptides can also be added that make it more likely that the proteins fold independently and behave as expected. Alternatively, internal ribosome entry sites (IRES) elements can be used to create multigene, or polycistronic, messages. IRES elements are able to bypass the ribosome scanning model of 5' methylated Cap dependent translation and begin translation at internal sites. Multiple open reading frames can be transcribed together, each separated by an IRES, creating polycistronic messages. By virtue of the IRES element, each open reading frame is accessible to ribosomes for efficient translation. IRES sequences are known in the art and include those from encephalomycarditis virus (EMCV) (Ghattas, I. R. et al., Mol. Cell. Biol., 11:5848-5849 (1991); BiP protein (Macejak and Sarnow, Nature, 353:91 (1991)); the Antennapedia gene of *drosophilia* (exons d and e) [Oh et al., Genes & Development, 6:1643-1653 (1992)); those in polio virus [Pelletier and Sonenberg, Nature, 334:320325 (1988); see also Mountford and Smith, TIG, 11:179-184 (1985)). Numerous other recombinant and fusion techniques are known and can be adapted for producing the disclosed peptides and proteins.

Also disclosed are compositions including a first antibody comprising the idiotype of monoclonal antibody clone 303123 linked to a first near-infrared (NIR) fluorophore and a second antibody comprising the idiotype of monoclonal antibody clone 315602 linked to a second NIR fluorophore.

The composition can further include a third antibody comprising the idiotype of monoclonal antibody clone 304-1A5 or clone 31A5 linked to a third NIR fluorophore. The first antibody can consists essentially of monoclonal antibody clone 303123. The second antibody can consists essentially of monoclonal antibody clone 315602. The third antibody can consists essentially of monoclonal antibody clone 304-1A5 or clone 31A5.

1. Cellular Target Binding Domain
    a. Antibodies

In preferred embodiments, the targeted imaging probes are antibodies that specifically bind the cellular targets. Therefore, antibodies that specifically bind CAIX, CAXII, mammaglobin-A, CEACAM6, CXCL10, and MMP-9 are disclosed for use in the disclosed compositions and methods.

The anti-CAIX antibody preferably specifically binds human CAIX protein (Accession No. NP_001207). In some embodiments, the anti-CAIX antibody specifically binds the N-terminus and the extracellular domain of human CAIX. In particularly preferred embodiments, the anti-CAIX antibody specifically binds amino acids 59-414 of human CAIX protein. As an example, the anti-CAIX antibody can be the monoclonal antibody (mAb) clone 303123 (R&D systems) or can have the idiotype of this clone. In addition, suitable anti-CAIX antibody can be identified that bind the same epitope as this clone.

The anti-CAXII antibody preferably specifically binds human CAXII protein (Accession No. NP_001209). In some embodiments, the anti-CAXII antibody specifically binds the N-terminus and the extracellular domain of human CAXII. In particularly preferred embodiments, the anti-CAXII antibody specifically binds amino acids 25-291 of human CAXII protein. As an example, the anti-CAXII antibody can be the monoclonal antibody (mAb) clone 315602 (R&D systems) or can have the idiotype of this clone. In addition, suitable anti-CAXII antibody can be identified that bind the same epitope as this clone.

The anti-Mammaglobin-A antibody preferably specifically binds human Mammaglobin-A (Accession No. NP_002402.1). As an example, the anti-Mammaglobin-A antibody can be the monoclonal antibody (mAb) clone 304-1A5 or 31A5 (Zeta Corp., California, Sierra Madre) or can have the idiotype of one of these clones. In addition, suitable anti-Mammaglobin-A antibody can be identified that bind the same epitope as this clone.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Antibodies for use in the disclosed compositions and methods can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. Fab is the fragment of an antibody that contains a monovalent antigen-binding fragment of an antibody molecule. A Fab fragment can be produced by digestion of whole antibody with the enzyme papain to yield an intact light chain and a portion of one heavy chain. Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region. (Fab')$_2$ is the fragment of an antibody that can be obtained by treating whole antibody with the enzyme pepsin without subsequent reduction. F(ab')$_2$ is a dimer of two Fab' fragments held together by two disulfide bonds. Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

Techniques can also be adapted for the production of single-chain antibodies specific for the cellular targets. Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two $V_H$ and two $V_L$ regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Preferably, if the antibody is to be administered to humans, the antibody is a human antibody or is a "humanized" antibody derived from a non-human animal. Methods for humanizing non-human antibodies are known in the art and have been described in, for example, U.S. Pat. Nos. 5,530,101; 5,585,089; 5,693,762; 6,180,370; and 6,407,213.

b. Peptides

In some embodiments, the targeted imaging probe can contain a peptide that binds the cellular target CAIX, CAXII, mammaglobin-A, CEACAM6, CXCL10, or MMP-9. In some embodiments, the peptide comprises the idiotype of an antibody, such as those described above. In other embodiments, the peptide can be identified by screening a library of peptides against the cellular target.

c. Peptidomimetics

In some embodiments, the targeted imaging probe can contain a peptidomimetic that binds CAIX, CAXII, mammaglobin-A, CEACAM6, CXCL10, or MMP-9. A peptidomimetic is a small protein-like chain designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. This can have a role in the development of drug-like compounds from existing peptides. These modifications involve changes to the peptide that will not occur naturally (such as altered backbones and the incorporation of nonnatural amino acids).

Methods of making peptidomimetics based upon a known polypeptide sequence is described, for example, in U.S. Pat. Nos. 5,631,280; 5,612,895; and 5,579,250. Peptidomimetics can have a non-amino acid residue with non-amide linkages at a given position. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

d. Aptamers

In some embodiments, the targeted imaging probe can contain an aptamer that binds CAIX, CAXII, mammaglobin-A, CEACAM6, CXCL10, or MMP-9. Aptamers are single-stranded RNA or DNA oligonucleotides 15 to 60 base in length that bind with high affinity to specific molecular targets. Most aptamers to proteins bind with Kds (equilibrium constant) in the range of 1 pM to 1 nM, similar to monoclonal antibodies. These nucleic acid ligands bind to nucleic acid, proteins, small organic compounds, and even entire organisms.

Aptamers can be selected by incubating the target molecule in a large (e.g., 1010 to 1020) pool of oligonucleotide (usually 40 to 60mers). The large pool size of the oligonucleotide ensures the selection and isolation of the specific aptamer. Aptamers can distinguish between closely related but non-identical members of a protein family, or between different functional or conformational states of the same protein. The protocol called systematic evolution of ligands by exponential enrichment (SELEX) is generally used with modification and variations for the selection of specific aptamers. Using this process, it is possible to develop new aptamers in as little as two weeks.

e. Sulfonamide-Based Inhibitors

In some embodiments, the targeted imaging probe can contain a carbonic anhydrase inhibitor that binds CAIX and/or CAXII. Carbonic anhydrase inhibitors are a class of pharmaceuticals that suppress the activity of carbonic anhydrase by binding to its catalytic site. Suitable carbonic anhydrase inhibitors generally contain a sulfonamide group. Non-limiting examples of carbonic anhydrase inhibitors include Acetazolamide, Brinzolamide, Methazolamide, Dorzolamide, and Topiramate.

f. Natural Ligands and Synthetic Analogues

In some embodiments, the targeted imaging probe can contain a natural ligand of the cellular targets on cancer cells, or a fragment or analogue thereof.

For example, Toll-like receptor 2 (TLR2) recognizes cell-wall components such as peptidoglycan, lipoteichoic acid and lipoprotein from gram-positive bacteria, lipoarabinomannan from mycobacteria, and zymosan from yeast cell wall. Therefore, in some embodiments, the natural ligand is a cell-wall component of a microorganism, such as bacteria or yeast.

In other embodiments, the targeted imaging probe contains a synthetic analogue of a natural ligand. For example, synthetic diacylated lipoprotein corresponding to N-terminal partial structures of bacterial lipoproteins have also been developed that bind TLR2. In some embodiments, the targeted imaging probe contains the TLR2 ligand dipalmitoyl-S-glyceryl-L-Cys-Ser-(Lys)$_4$ (Pam$_2$CSK$_4$), which has the following structure:

In some embodiments, the targeted imaging probe contains the lipolanthionine peptide (2R,6R)-Pam$_2$LanHda-Ser-(Lys)$_4$-NH$_2$ (lipolan).

In some embodiments, the targeted imaging probe contains MALP-2, which is a diacylated lipopeptide isolated from *Mycoplasma Fermentans*.

In some embodiments, the targeted imaging probe contains a cellular target binding domain having the formula:

X-Dhp(Pam$_2$)-peptide MALP2, where "X" represents the addition of: Palmitoyl, Fluorescein, Ac-PEGO20, Ac-Aha, Adapaleneyl, Ac-Aun, or Tretinoyl. Ac=acetyl; Dhc=1,2-dihydroxypropylcysteine; Aha=epsilon-aminohexanoic acid; Aun=epsilon-aminoundecanoic acid; PEGO20=20 atoms long polyethelene glycol (4 Peg units); Pam$_2$=dipalmitoyl-S-glyceryl; Pam$_3$=tripalmitoyl-S-glyceryl.

Figure 14:
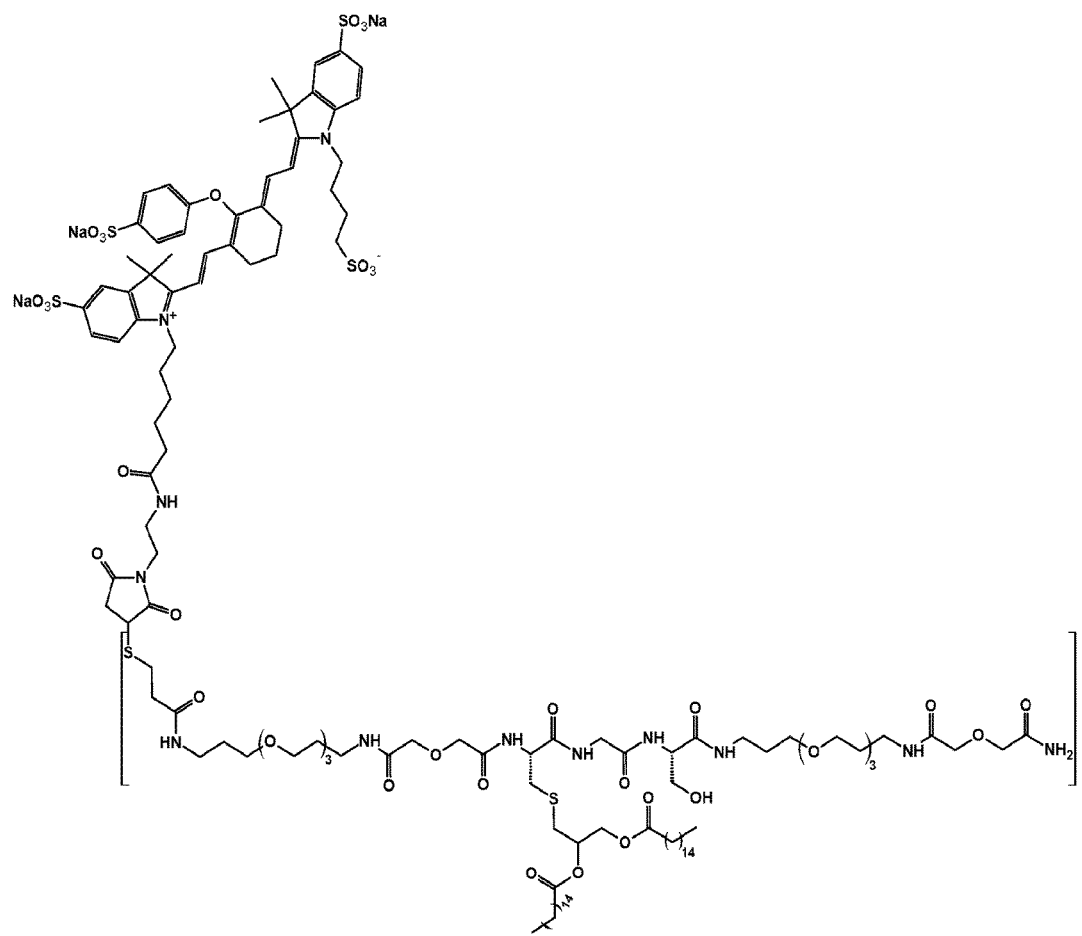
FIG. 14 is the chemical structure of the T-02 compound conjugated to the LiCor IRDye800CW.

In some embodiments, the targeted imaging probe contains a PEGO group. For example, the TLR2 agonist analog T-02 (Ac-PEGO-Dhc (Pam)$_2$-Gly-Ser-PEGO-NH$_2$) was derived from synthetic origin based on the scaffold of MALP2 with manipulation of N terminal PEGO (see FIG. 14 for the structure of T-02 labeled with Licor IR® 800CW Maleimide dye). T-03 (Ac-PEGO-Dhc(Pam)$_2$-Ser-Arg-Phe-Asp-Glu-Asp-Asp-Leu-Glu-NH$_2$, SEQ ID NO:5) was

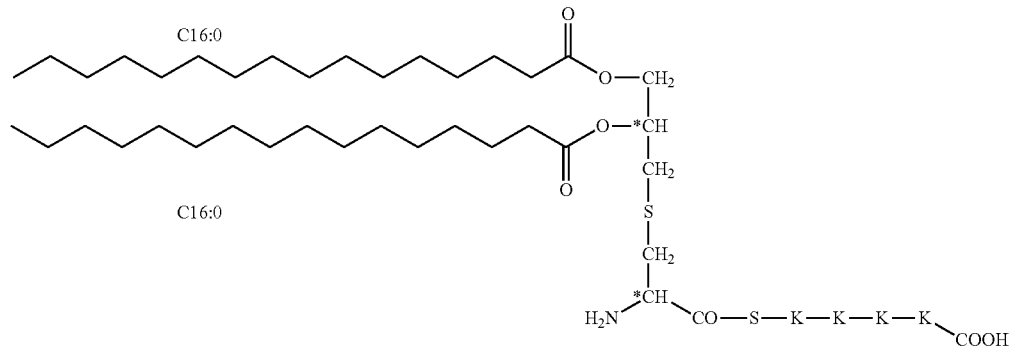

In some embodiments, the targeted imaging probe contains the TLR2 ligand tripalmitoyl-S-glyceryl-L-Cys-Ser-Lys-Lys-Lys-Lys (Pam$_3$CSK$_4$), which has the following structure:

derived from CD14 peptide origin manipulation of N-terminal PEGO. T-05 (Ac-PEGO-Dhc(Pam)$_2$-Gly-Ser-Gln-Asn-Leu-Ala-Ser-Leu-Glu-Glu-NH$_2$, SEQ ID NO:6) was derived from *S. aureus* peptide origin.

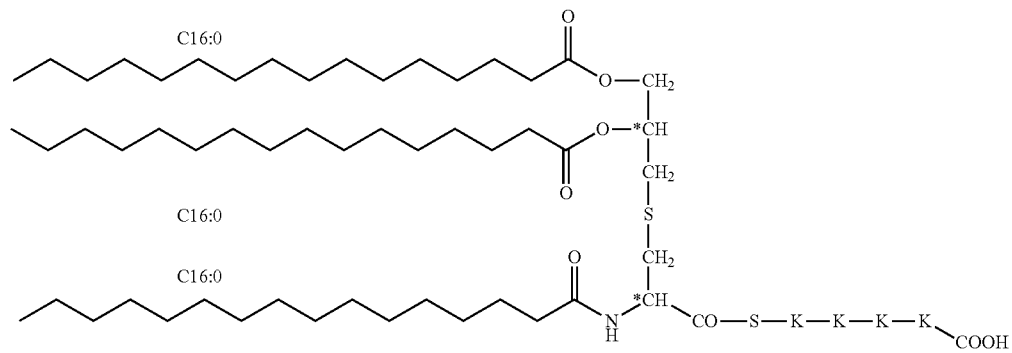

In some embodiments, the targeted imaging probe can have the structure

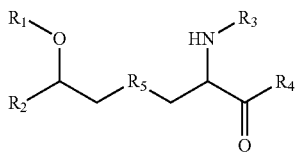

where R$_1$ is —CO—R$_6$ or H, wherein R$_6$ is C$_{12}$ to C$_{18}$ alkyl or alkenyl;

where R$_2$ is —CH$_2$—O—CO—R$_7$, —CH$_2$—OH, or —H, wherein R$_7$ is any C$_{12}$ to C$_{18}$ alkyl, alkenyl, amine, alkyl amine, alkenyl amine, alkyl ether, polyether, wherein R$_7$ is optionally substituted with one or more functional group(s) selected from the group consisting of alkyl, alkenyl, ether, polyether, or alkyl amine;

where R$_3$ is R$_8$-label, wherein R$_8$ is acetyl-PEGO- (Ac-PEGO), palmitoyl-, fluorescein-, acetyl-6-aminohexanoyl- (Ac-Aha), adapalenoyl-, acetyl-11-aminoundecanoyl- (Ac-Aun), or tretinoyl-;

where R$_4$ is -Gly-DSer-PEGO-NH$_2$, -Gly-DSer-NH$_2$, -Cys-Ser-(Lys)$_4$-NH$_2$, -Gly-Asn-Asn-Asp-Glu-Ser-Asn-Ile-Ser-Phe-Lys-Glu-Lys-NH$_2$, -Ser-Arg-Phe-Asp-Glu-Asp-Asp-Leu-Glu-NH$_2$, -Gly-Ser-Gln-Asn-Leu-Ala-Ser-Leu-Glu-Glu-NH$_2$, or -serine methyl ester; and where R$_5$ is —S— or —Se—.

In some embodiments, if R$_1$ is H, then R$_2$ is —CH$_2$—O—CO—R$_7$ wherein R$_7$ is any C$_{12}$ to C$_{18}$ alkyl or alkenyl.

In some embodiments, R$_1$ can be —CO—R$_6$, wherein R$_6$ is C$_{12}$ to C$_{18}$ alkyl; R$_2$ can be —CH$_2$—O—CO—R$_7$, wherein R$_7$ is any C$_{12}$ to C$_{18}$ alkyl; R$_3$ can be R$_8$-label, wherein R$_8$ is acetyl-PEGO- (Ac-PEGO), palmitoyl-, fluorescein-, acetyl-6-aminohexanoyl- (Ac-Aha), adapalenoyl-, acetyl-11-aminoundecanoyl- (Ac-Aun), or tretinoyl-; R$_4$ can be -Gly-DSer-PEGO-NH$_2$, -Gly-DSer-NH$_2$, -Cys-Ser-(Lys)$_4$-NH$_2$, -Gly-Asn-Asn-Asp-Glu-Ser-Asn-Ile-Ser-Phe-Lys-Glu-Lys-NH$_2$, -Ser-Arg-Phe-Asp-Glu-Asp-Asp-Leu-Glu-NH$_2$, -Gly-Ser-Gln-Asn-Leu-Ala-Ser-Leu-Glu-Glu-NH$_2$, or -serine methyl ester; and R$_5$ can be —S—.

2. Detectable Labels

The disclosed targeted imaging probes are preferably linked to a detectable label. Substances suitable for detectably labeling imaging agents include fluorescent molecules (a.k.a. fluorochromes and fluorophores), chemiluminescent reagents (e.g., luminol), bioluminescent reagents (e.g., luciferin and green fluorescent protein (GFP)), metals (e.g., gold nanoparticles), and radioactive isotopes (radioisotopes). Suitable detectable labels can be selected based on the choice of imaging method. For example, in preferred embodiments, the detectable label is near infrared fluorescent dye for optical imaging, a Gadolinium chelate for MRI imaging, a radionuclide for PET or SPECT imaging, or a gold nanoparticle for CT imaging.

a. Fluorophores

Fluorophores are compounds or molecules that absorb energy of a specific wavelength and re-emit energy at a different (but equally specific) wavelength. In preferred embodiments, the detectable label is a near-infrared (NIR) fluorophore. Suitable NIRs include, but are not limited to, VivoTag-S® 680 and 750, Kodak X-SIGHT Dyes and Conjugates, DyLight 750 and 800 Fluors, Cy 5.5 and 7 Fluors, Alexa Fluor 680 and 750 Dyes, and IRDye 680 and 800CW Fluors. In some embodiments, Quantum dots, with their photostability and bright emissions, can also be used with optical imaging.

b. Radioisotopes

A radioisotope can be incorporated into or attached directly to a targeted imaging agent. Examples of useful radioisotopes include, but are not limited to, tritium, $^{11}$C, $^{13}$N, $^{14}$C, $^{15}$O, $^{18}$Fl, $^{62}$Cu, $^{64}$Cu, $^{67}$Cu, $^{68}$Ga, $^{76}$Br, $^{82}$Rb, $^{90}$Y, $^{99m}$Tc, $^{111}$In, $^{123}$I, $^{124}$I, $^{125}$I, $^{131}$I, $^{153}$Sm, $^{201}$Tl, $^{186}$Re, $^{188}$Re, and $^{212}$Bi. In some embodiments, the radioisotope is attached to the targeted imaging agent by halogenation. In some embodiments, the radioisotopes is attached to the targeted imaging agent by a linking group or bound by a chelating group, which is then attached to the targeted imaging agent directly or by means of a linker.

3. Adjuvants

The disclosed TLR2 agonists can also be used as adjuvants to enhance stimulation of an immune response, such as with a vaccine.

B. Pharmaceutical Formulations

Pharmaceutical formulations are provided that contain one or more targeted imaging probes in combination with one or more pharmaceutically acceptable excipients.

1. Pharmaceutically Acceptable Excipients

The disclosed targeted imaging probes are preferably formulated for parenteral administration. Parenteral formulations can be prepared as aqueous compositions using techniques is known in the art. Typically, such compositions are prepared as solutions or suspensions; solid forms suitable to prepare solutions or suspensions upon the addition of a reconstitution medium; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

2. Dosage

Targeted imaging probes are preferably administered in a dose equivalent to parenteral administration of about 0.1 ng to about 100 g per kg of body weight, such as about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight, and from about 1 mg to about 50 mg per kg of body weight. For example, the amount of targeted imaging probes administered to achieve an effective dose for imaging can be about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

C. Kits

One or more of the compositions described herein can be assembled in kits. Printed instructions, either as inserts or as labels, indicating quantities of the components to be administered, guidelines for administration, and/or guidelines for mixing the components, can also be included in the kit. Kits of the invention can optionally include pharmaceutically acceptable carriers and/or diluents.

The disclosed kit can contain, for example, antibodies that specifically bind one, two, three, or more of CAIX, CAXII, mammaglobin-A, CEACAM6, CXCL10, and MMP-9. In preferred embodiments, the disclosed kit can contain antibodies that specifically bind CAIX and CAXII. In some embodiments, the disclosed kit can contain antibodies that specifically bind CAIX, CAXII, and mammaglobin-A. In these embodiments, the antibodies that specifically bind different cellular targets can in some embodiments be linked to the same detectable label, or to a different label that is indistinguishable by the imaging device. In preferred embodiments, the antibodies that specifically bind different cellular targets can be linked to different detectable labels that are distinguishable by the imaging device. For example, where the detectable label is a near-infrared (NIR) fluorophore, the NIR fluorophores preferably absorb and emit at different wavelengths.

In preferred embodiments a pharmaceutical composition can be provided in the kit as a liquid or solution. The kit can also include means of administration, such as one or more of a syringe (e.g., a barrel syringe or a bulb syringe), intravenous (IV) bag, IV line, IV needle, and/or cannula. In some embodiments, the kit can comprise an ampoule or syringe containing a pharmaceutical compositions in liquid or solution form Kits can include one or more containers containing a one or more targeted imaging probes disclosed herein. Containers of the kit can be of any suitable material, e.g., glass, plastic, metal, etc., and of any suitable size, shape, or configuration.

Also disclosed are kits including two or more antibodies that specifically bind a cellular target selected from the group consisting of carbonic anhydrase 9 (CAIX), carbonic anhydrase 12 (CAXII), mammaglobin-A, carcinoembryonic antigen-related cell adhesion molecule 6 (CEACAM6), C—X—C motif chemokine 10 (CXCL10), and matrix metallopeptidase 9 (MMP-9) in two or more containers, wherein at least one antibody is linked to a first near-infrared (NIR) fluorophore and at least a second antibody is linked to a second near-infrared (NIR) fluorophore.

In some embodiments, light in either the absorption or emission spectrum of the first NIR fluorophore does not excite the second NIR fluorophore. In some embodiments, at least one of the two or more antibodies consists essentially of monoclonal antibody clone 303123. In some embodiments, at least one of the two or more antibodies consists essentially of monoclonal antibody clone 315602. In some embodiments, at least one of the two or more antibodies consists essentially of monoclonal antibody clone 304-1A5 or clone 31A5.

III. Methods

A. Detecting Cancer In Vivo

The disclosed targeted imaging probes can be used in combination with molecular imaging to detect cancer cells, such as those that have metastasized and therefore spread to another organ or tissue of the body, using an in vivo imaging device. A non-invasive method is therefore provided for detecting cancer cells in a subject that involves administering a pharmaceutical composition containing targeted imaging probes to the subject and then detecting the biodistribution of the targeted imaging probes using an imaging device. In some embodiments, the pharmaceutical composition is injected into the parenchyma. In other embodiments, the pharmaceutical composition is injected into the circulation.

The disclosed targeted imaging probes can also be used for intraoperative detection of cancer cells. For example, the disclosed targeted imaging probes can be used for intraoperative lymphatic mapping (ILM) to trace the lymphatic drainage patterns in a cancer patient to evaluate potential tumor drainage and cancer spread in lymphatic tissue. In these embodiments, the targeted imaging probes are injected into the tumor and their movement through the lymphatic system is traced using a molecular imaging device. As another example, the disclosed targeted imaging probes can be used for intraoperative assessment of, for example, tumor margins and tumor proximal tissues for the presence of cancer cells. This can be useful, for example, in effectively resecting tumors and detecting the spread of cancer proximal to the tumor.

The disclosed methods of imaging to detect cancer cells are referred to herein as non-invasive. By non-invasive is meant that the targeted imaging probes can be detected from outside of the subject's body. By this it is generally meant that the signal detection device is located outside of the subject's body. It is understood, however, that the disclosed targeted imaging probes can also be detected from inside the subject's body or from inside the subject's gastrointestinal tract or from inside the subject's respiratory system and that such methods of imaging are also specifically contimplated. For example, for intraoperative detection, the signal detection device can be located either outside or inside of the subject's body. From this it should be understood that the a non-invasive method of imaging can be used along with, at the same time as, or in combination with an invasive procedure, such as surgery.

In some embodiments, the method can be used to diagnose cancer in a subject or detect cancer in a particular organ of a subject. A particularly useful aspect of this method is the ability to search for metastatic cancer cells in secondary tissues or organs, such as lymph nodes, or at or near tumor margins. Therefore, the disclosed methods can be used for assessing lymph node status in patients that have or are suspected of having cancer, such as breast cancer. This avoids the need to biopsy the tissue or organ, e.g., remove a lymph node. In some embodiments, the method involves administering to the patient targeted imaging probes and detecting whether the probes have bound to cells in a lymph node. In some of these embodiments, the lymph node can be an axillary lymph node (ALN). In other embodiments, the lymph node can be a sentinel lymph node. In further embodiments, both axillary and sentinel lymph nodes can be assessed for binding of the agent to cells in the lymph node.

In some embodiments, the method can be used for intraoperative imaging, such as in label-guided surgery. An example of fluorescence-guide surgery is described in Example 18.

The method can also be used with other therapeutic or diagnostic methods. For example, the method can also be used during an operation to, for example, guide cancer removal, which is referred to herein as "intraoperative guidance" or "image guided surgery." In a particular embodiment, the method can be used for therapeutic treatment to remove or destroy cancer cells in a patient's lymph nodes. For example, targeted imaging probes can be administered to a patient, and the location of cancerous tissue (e.g., lymph nodes) can be determined and removed using image guided surgery. In another preferred embodiment, the method can be used for therapeutic treatment to prevent positive microscopic margins after tumor resection. For example, targeted imaging probes can be administered to a patient, the location of cancer cells around a tumor can be determined, and the complete tumor removed using image guided surgery. In these embodiments, the physician administers targeted imaging probes to the patient and uses an imaging device to detect the cancer cells, guide resection of tissue, and assure that all of the cancer is removed, i.e., negative cancer margins. In addition, the imaging device can be used post-operatively to determine if any cancer remains or reoccurs.

In some embodiments, the targeted imaging probes can be linked to a therapeutic compound. The therapeutic compound or moiety can be one that kills or inhibits cancer cells directly (e.g., cisplatin) or it can be one that can kill or inhibit a cancer cell indirectly (e.g., gold nanoparticles that kill or destroy cancer cells when heated using a light source). If the therapeutic compound or moiety is one that kills or inhibits a cancer cell indirectly, then the method further comprises a step of taking appropriate action to "activate" or otherwise implement the anti-cancer activity of the compound or moiety. In a specific embodiment, the therapeutic compound or moiety attached to the agent can be a gold nanoparticle and following administration to the patient and binding of the agent to cancer cells, the gold nanoparticles are heated, e.g., using a laser light, to kill or destroy the nearby cancer cells (photothermal ablation). For example, in some embodiments, the method involves image guided surgery using targeted imaging probes to detect and resect cancer from a subject followed by the use of the same or different targeted imaging probes linked to a therapeutic compound to kill remaining cancer cells.

Disclosed are non-invasive methods for in vivo detection of cancer cells in a subject, the method including administering to the subject a targeted imaging probe that specifically binds a cellular target selected from the group consisting of carbonic anhydrase 9 (CAIX), carbonic anhydrase 12 (CAXII), mammaglobin-A, carcinoembryonic antigen-related cell adhesion molecule 6 (CEACAM6), C—X—C motif chemokine 10 (CXCL10), and matrix metallopeptidase 9 (MMP-9); and imaging the subject with a molecular imaging device to detect the targeted imaging probe in the subject, wherein detection of the targeted imaging probe in an organ of a subject is an indication of cancer cells in the organ.

The cellular target can be CAIX, CAXII, mammaglobin-A, or a combination thereof. The method can include administering to the subject a first targeted imaging probe that specifically binds CAIX, a second targeted imaging probe that specifically binds CAXII, or a combination thereof, wherein detection of the first targeted imaging probe or the second targeted imaging probe in an organ of a subject is an indication of cancer cells in the organ. The method can include administering to the subject a targeted imaging probe that specifically binds mammaglobin-A, wherein detection of the targeted imaging probe that specifically binds mammaglobin-A in an organ of a subject is an indication of breast cancer cells in the organ.

The molecular imaging device can include a gamma radiation detector. The targeted imaging probe can include an antibody linked to a detectable label. The targeted imaging probe that specifically binds CAIX is an antibody can include the idiotype of monoclonal antibody clone 303123. The targeted imaging probe that specifically binds CAXII is an antibody can include the idiotype of monoclonal antibody clone 315602. The targeted imaging probe that specifically binds mammaglobin-A is an antibody can include the idiotype of monoclonal antibody clone 304-1A5 or clone 31A5.

The antibody can consist essentially of monoclonal antibody clone 303123, clone 315602, clone 304-1A5, or clone 31A5. The detectable label can be a near-infrared (NIR) fluorophore. The targeted imaging probe can include a first antibody having the idiotype of monoclonal antibody clone 303123 linked to a first NIR fluorophore and a second antibody having the idiotype of monoclonal antibody clone 315602 linked to a second NIR fluorophore.

The cancer cells can be metastasized cancer cells. The cancer cells can be breast cancer cells. The cancer cells can be non small-cell carcinoma cells.

1. Cancers

In some embodiments, the cancer of the disclosed methods can be any cell in a subject undergoing unregulated growth. In preferred embodiments, the cancer is any cancer cell capable of metastasis. For example, the cancer can be a sarcoma, lymphoma, leukemia, carcinoma, blastoma, or germ cell tumor. A representative but non-limiting list of cancers that the disclosed compositions can be used to detect include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In preferred embodiments, the cancer is breast cancer. Breast cancers originating from ducts are known as ductal carcinomas, and those originating from lobules that supply the ducts with milk are known as lobular carcinomas. Common sites of breast cancer metastasis include bone, liver, lung and brain.

In other preferred embodiments, the cancer is non-small-cell lung carcinoma (NSCLC). NSCLC is any type of epithelial lung cancer other than small cell lung carcinoma (SCLC). The most common types of NSCLC are squamous cell carcinoma, large cell carcinoma, and adenocarcinoma, but there are several other types that occur less frequently, and all types can occur in unusual histologic variants and as mixed cell-type combinations.

In other preferred embodiments, the cancer is pancreatic cancer. The most common type of pancreatic cancer, accounting for 95% of these tumors is adenocarcinoma, which arises within the exocrine component of the pancreas. A minority arises from the islet cells and is classified as a neuroendocrine tumor.

2. Molecular Imaging

Methods are disclosed for in vivo detection of cancer cells using the disclosed targeted imaging probes in combination with a molecular imaging device. Molecular imaging differs from traditional imaging in that probes known as biomarkers are used to help image particular targets or pathways. There are many different modalities that can be used for noninvasive molecular imaging. Each have their different strengths and weaknesses and some are more adept at imaging multiple targets than others.

a. Magnetic Resonance Imaging (MRI)

MRI has the advantages of having very high spatial resolution and is very adept at morphological imaging and functional imaging. However, MRI has a sensitivity of around $10^{-3}$ mol/L to $10^{-5}$ mol/L which, compared to other types of imaging, can be very limiting. This problem stems from the fact that the difference between atoms in the high energy state and the low energy state is very small. For example, at 1.5 tesla, a typical field strength for clinical MRI, the difference between high and low energy states is approximately 9 molecules per 2 million. Improvements to increase MR sensitivity include hyperpolarization by increasing magnetic field strength, optical pumping, or dynamic nuclear polarization. There are also a variety of signal amplification schemes based on chemical exchange that increase sensitivity.

b. Optical Imaging

There are a number of approaches used for optical imaging. The various methods depend upon fluorescence, bioluminescence, absorption or reflectance as the source of contrast. Optical imaging's most valuable attribute is that it does not have strong safety concerns like the other medical imaging modalities. The downside of optical imaging is the lack of penetration depth, especially when working at visible wavelengths. Depth of penetration is related to the absorption and scattering of light, which is primarily a function of the wavelength of the excitation source. Light is absorbed by endogenous chromophores found in living tissue (e.g. hemoglobin, melanin, and lipids). In general, light absorption and scattering decreases with increasing wavelength. Below ~700 nm (e.g. visible wavelengths), these effects result in shallow penetration depths of only a few millimeters. Thus, in the visible region of the spectrum, only superficial assessment of tissue features is possible. Above 900 nm, water absorption can interfere with signal-to-background ratio. Because the absorption coefficient of tissue is considerably lower in the near infrared (NIR) region (680-900 nm), light can penetrate more deeply, to depths of several centimeters.

Fluorescent probes and labels are an important tool for optical imaging. A number of near-infrared (NIR) fluorophores have been employed for in vivo imaging, including Kodak X-SIGHT Dyes and Conjugates, DyLight 750 and 800 Fluors, Cy 5.5 and 7 Fluors, Alexa Fluor 680 and 750 Dyes, IRDye 680 and 800CW Fluors. In some embodiments, the detectable label is a Quantum dot.

c. Nuclear Medicine Imaging

Nuclear medicine imaging involves the use and detection of radioisotopes in the body. Nuclear medicine imaging techniques include scintigraphy, single photon emission computed tomography (SPECT), and positron emission tomography (PET). In these techniques, radiation from the radioisotopes is captured by a gamma camera to form two-dimensional images (scintigraphy) or 3-dimensional images (SPECT and PET).

Suitable gamma-emitting radioisotopes for scintigraphy and SPECT include $^{99m}$Tc, $^{111}$In, $^{123}$I, $^{133}$Xe, $^{201}$Tl. Suitable radioisotopes have relatively long half lives (a few hours to a few days) making them easy to produce and relatively cheap. This represents a major advantage, since it is significantly cheaper than either PET or MRI. However it lacks good spatial resolution. Additionally, due to the radioactivity of the contrast agent, there are safety aspects concerning the administration of radioisotopes to the subject, especially for serial studies.

Radionuclides used in PET scanning are typically isotopes with short half-lives. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F being the most clinically utilized. One of the major disadvantages of PET is that most of the probes must be made with a cyclotron. Most of these probes also have a half life measured in hours, forcing the cyclotron to be on site. PET imaging is, however, very sensitive. A typical PET scanner can detect between $10^{-11}$ mol/L to $10^{-12}$ mol/L concentrations.

Gamma radiation from radioisotopes is detected using a gamma particle detection device. In some embodiments, the gamma particle detection device is a Gamma Finder® device (SenoRx, Irvine Calif.). In some embodiments, the gamma particle detection device is a Neoprobe® GDS gamma detection system (Dublin, Ohio).

B. Administration

The disclosed pharmaceutical compositions are preferably administered parenterally into the parenchyma or into the circulation so that the targeted imaging probes reach target tissues where cancer cells may be located. In some preferred embodiments, the pharmaceutical composition is administered directly into or adjacent to a tumor mass. In other preferred embodiments, the pharmaceutical composition is administered intravenously. In still other embodiments, the pharmaceutical composition is administered intraperitoneally, intramuscularly, subcutaneously, intracavity, or transdermally.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

C. Actions Based on Imaging and Identifications

The disclosed methods include the determination, identification, indication, correlation, diagnosis, prognosis, etc. (which can be referred to collectively as "identifications") of subjects, diseases, conditions, states, etc. based on imagings, measurements, detections, comparisons, analyses, assays, screenings, etc. For example, the disclosed imaging methods allow identification of patients, organs, tissues, etc. having cancer cells, metastasized cancer cells, cancer cells beyond tumor margins, etc. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a imaging, measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different imagings, measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

The disclosed imagings, measurements, detections, comparisons, analyses, assays, screenings, etc. can be used in other ways and for other purposes than those disclosed. For example, imaging of cancer cells can be used to identify areas of organs of tissues or margins of cancer-affected organs or tissues. Thus, the disclosed imagings, measurements, detections, comparisons, analyses, assays, screenings, etc. do not encompass all uses of such imagings, measurements, detections, comparisons, analyses, assays, screenings, etc.

EXAMPLES

Example 1: Microarray and TMA Studies on Patient Tissue Samples

Materials and Methods
DNA Microarray Analysis:
A list of 3,800 cell surface genes was compiled from Gene Bank and used to filter Affymetrix® expression microarray data from 304 breast cancer samples of which 37 were noted as being from LN positive patients; and from normal tissues including 116 normal breast, 23 lymph node, 4 spleen, 5 lung, 4 heart, 8 kidney and 4 liver samples. The Affymetrix® CEL files for the tumor samples were downloaded from the Gene Expression Omnibus (GEO) database (www.ncbi.nlm.nih.gov/projects/geo/index.cgi), data series GSE2109. This is the Expression Project for Oncology carried out by the International Genomics Consortium (IGC). Normal tissue data were from the GEO data series GSE7307, Human Body Index, which was a transcriptional profiling project carried out by Neurocrine Biosciences, Inc. The CEL files were analyzed using the MAS 5.0 algorithm (Affymetrix Corp.) and then screened through a rigorous quality control panel to remove samples with low percentages of probe sets called present by the MAS 5 algorithm, indicating problems with the amplification process; high scaling factors, indicating poor transcript abundance during hybridization; and poor 3'/5' ratios, indicating RNA degradation either prior to or during processing. The remaining samples were normalized to the trimmed average of 500 in the MAS 5 algorithm.

Immunohistochemistry (IHC) of Tissue Mircroarray (TMA):
A TMA was constructed at the Tissue Core of Moffitt Cancer Center containing human breast tissue samples of formalin-fixed and paraffin-embedded (FFPE) specimens. The TMA contains 50 normal breast tissue, 50 ductal carcinoma in situ, 50 invasive ductal carcinomas without metastasis, 50 invasive ductal carcinomas with metastasis, and 50 lymph node with macrometastases of breast. The procedure of the TMA construction and the protocol were described previously (Schlauder, S. M. et al. *Fetal Pediatr Pathol* 27:83-97 (2008)). For the current project, a 1:500 dilution of anti-CAXII antibody (Prestige Antibodies Powered by Atlas Antibodies, Sigma-Aldrich) was used as a primary antibody for CAXII staining and a 1:500 dilution of anti-CAIX rabbit polyclonal antibody (Abcam plc) was used for CAIX staining.

Statistics:
Data are represented as mean±s.d. and Student's t-test was used to determine significance.

Results
CAIX and CAXII were identified and validated as cell-surface markers for breast cancer lymph node (LN) metastasis. CAIX expression is observed in a variety of cancer types including breast cancer (Brennan, D. J. et al. *Clin Cancer Res* 12:6421-6431 (2006); Chia, S. K. et al. *J Clin Oncol* 19:3660-3668 (2001); Colpaert, C. G. et al. *Breast Cancer Res Treat* 81:137-147 (2003); Hussain, S. A. et al. *Br J Cancer* 96:104-109 (2007); Lancashire, L. J. et al. *Breast Cancer Res Treat* 120:83-93 (2010); Span, P. N. et al. *Br J Cancer* 89:271-276 (2003); Trastour, C. et al. *Int J Cancer* 120:1451-1458 (2007)), but is relatively absent from corresponding normal tissues (Supuran, C. T. et al. *Bioorg Med Chem* 15:4336-4350 (2007)). CAIX expression is correlated with high tumor grade and increased tumor size in breast cancer (Chia, S. K. et al. *J Clin Oncol* 19:3660-3668 (2001); Span, P. N. et al. *Br J Cancer* 89:271-276 (2003)).

To identify additional targets, a list of 3800 cell surface and secreted genes was curated from Gene Bank and used to filter DNA microarray data from 304 breast tumor samples (37 node positive), 111 normal breast tissue samples, 15 unaffected lymph node, and 189 samples from 6 unaffected organ sites in the area surrounding the axillary nodes and those involved in clearance and toxicity. Five genes, CA12, CEACAM6, CXCL9, CXCL10 and MMP9, were identified with high expression in breast cancer including lymph node positive tumors, but low expression in the normal tissues surveyed (FIGS. 1A-1B, 4A-4D). Since CXCL9, CXCL10 and MMP9 products are secreted, and CEACAM6 had significant expression in the lung, CAXII was selected for validation. Also, CAXII was intriguing because of the potential for development of probes targeting the carbonic anhydrase catalytic site using sulfonamide-based inhibitors as imaging probes, which would target both CAXII and CAIX.

For validation of protein expression, immunohistochemistry (IHC) of CAIX and CAXII was performed on a tissue microarray (TMA) containing 50 normal breast tissue samples, 50 ductal carcinoma in situ, 50 invasive ductal carcinomas without metastasis, 50 invasive ductal carcinoma with metastasis, and 50 lymph node macrometastases. As shown in Table 1, positive staining of CAIX and CAXII was observed in the ductal epithelium of 73.9% and 100% of normal breast tissue samples, respectively. These markers were not present in normal breast stroma. CAIX and CAXII staining was distributed in the cell membranes of tumor tissues. Lymph node metastases samples (44%) were positive for both CAIX and CAXII and all of the positive lymph nodes were found to express either CAIX or CAXII. Tumor heterogeneity was found in 28.6% and 35% for CAIX and CAXII, respectively.

TABLE 1

Expression of CAIX and CAXII in normal breast and breast cancer patients

|   | CA9 | CA12 | Combination |
|---|---|---|---|
| Normal | 73.9% | 100% | 100% (n = 7) |
| DCIS | 71.4% | 81.3% | 100% (n = 9) |
| IDC without Mets | 55.8% | 78.7% | 100% (n = 28) |
| IDC with Mets | 56.5% | 80.4% | 93% (n = 26) |
| LN Macro Mets | 71.4% | 75.5% | 100% (n = 31) |

Mammaglobin A is expressed in 45% of LN macrometastases on breast TMA. An analysis of expression of all three of these markers on our TMA shows that 100% of the samples LN macrometastses express at least one of the three markers, 31% express only one, 51% express two, and 18% express all three markers. Therefore, a combination of CAIX, CAXII and mammaglobin markers can be used as suitable targets for imaging agents for early diagnosis of metastatic breast cancer in lymph nodes.

Example 2: Cell Models and In Vitro Studies

Materials and Methods
Cell Culture:
A breast cancer cell line that expresses luciferase, MDA-mb-231-luc, (Baggett, B. et al. *Mol Imaging* 3:324-332

(2004)) was grown in RPMI 1640 containing 10% fetal bovine serum (Life Technologies), 0.03% L-glutamine, 100 units/mL penicillin, 100 µg/mL streptomycin and 300 µg/ml G418 (Mediatech) in 5% CO2 at 37° C.

Generation of Stably Transfected MDA-mb-231 Cells Bearing the CA12 Gene:

pCMV6-XL5 containing *homo sapiens* CA12 was purchased (Origene) and it was subcloned to pcDNA3.1-Zeo (Invitrogen) containing Zeocin™ as a selectable marker for mammalian cells. Briefly, pCMV6-XL5 and pcDNA3.1-Zeo were digested by NotI and XbaI (Invitrogen) and the digested fragment was inserted into NotI/XbaI restriction sites of digested pcDNA3.1-Zeo vector and the ligated mixture was transformed into competent cells of *E. coli* DH5α.

To identify the optimal concentration for selection, a range (50-1000 µg/ml) of Zeocin™ (Invitrogen) was tested on MDA-mb-231 cells. MDA-mb-231 cells expressing luciferase were transfected with 5 µg of pcDNA3.1-Zeo containing CA12. In response to zeocin, massive cell death was observed after ~5 days. After 2 weeks, resistant colonies appeared. Large colonies were selected and transferred to individual plates. The clone with the highest expression of CA12 was determined using qRT-PCR as previously described (Morse, D. L. et al. *Anal Biochem* 342:69-77 (2005)). RNA was extracted from each clone using an RNA extraction kit (Qiagen). CA12 specific primer sets were designed using Gene Runner Software for Windows version 3.05: forward, 5'-CTGGCATCATGTATTTAGGGGC-3' (SEQ ID NO:1) and reverse, 5'-GAGTTGCGCCTGTCA-GAAAC-3' (SEQ ID NO:2). β-actin was used for normalization. A clone with the highest expression was selected and maintained in medium containing 300 µg/ml of G418 and 800 µg/ml of zeocin.

Immunocytochemistry (ICC) and Fluorescence Microscopy:

To verify expression of CAXII in engineered cells, two sets of MDA-mb-231 (as a negative control) and MDA-mb-231/CAXII cells (each 1×10⁴) were plated onto glass coverslips placed at the bottom of culture wells and incubated for 16 h. Cells were fixed with a 1:1 mixture of cold methanol and acetone, air dried for 20 min, blocked with 3% BSA and 0.2% saponin in PBS for 1 hour at room temperature and incubated with 1:50 CAXII antibody (Sigma-Aldrich) for 1 h. Plates were then washed (3 times, 5 min each) with PBS containing 0.2% saponin, and incubated with 1:2000 secondary antibody (Alexa-Fluor 488 goat anti-mouse IgG, Invitrogen). After three washes, coverslips were mounted using mounting medium with DAPI, 4,6-diamidino-2-phenylindole (Vector Laboratories, Inc.). Samples were viewed in the Analytic Microscopy Core Facility at Moffitt Cancer Center using an automated Zeiss Observer Z.1 inverted microscope with 40×/1.3NA oil immersion objectives through narrow bandpass DAPI, FITC/A488 Chroma filter cubes, Nomarski Differential Interference Contrast polarizing, and analyzing prisms. Images were produced using the AxioCam MRm CCD camera and Axiovision version 4.6 software suite (Carl Zeiss Inc.).

Conjugation of Antibodies to Dye and Fluorescence Microscopy Studies:

A mixture of 10 µg anti-human CAIX monoclonal antibody (mAb) (Clone 303123, R&D systems) was incubated with 10 µg VivoTag-S® 680 (VisEn Medical) at room temperature for 1 hour. The immunogen for this antibody is rhCA9; accession # NP_001207; aa 59-414, which corresponds to the N-terminus and the extracellular domain. The conjugate was purified with a Sephadex® G25 column (Roche) and eluted into a sterile tube. Protein (A280) and dye (A680) absorbance was determined using an ND-1000 spectrophotometer (NanoDrop) and used to confirm the number of fluorophore molecules conjugated to each antibody molecule. The conjugate was termed CA9Ab-680.

The same procedure was used for conjugation of CAXII mAb (Clone 315602, R&D system) to the dye. The immunogen for this antibody is rhCA12; accession #NP_001209; aa 25-291, which corresponds to the N-terminus and the extracellular domain. The conjugate was termed CA12Ab-680.

To verify that CA9Ab-680 and CA12Ab-680 retained binding specificity, 1×10⁴ MDA-mb-231 cells (constitutively expressing CAIX and not expressing CAXII) and the same number of MDA-mb-231/CAXII (engineered cells to express CAXII) were seeded and incubated for 16 hours, then fixed as described above. The fixed cells that constitutively express CAIX were incubated with 0.5 µg/µl CA9Ab-680, and both cell lines were incubated with 0.5 µg/µl CA12Ab-680. Cells were also incubated with 5.0 µg/mL of wheat germ agglutinin (WGA), Oregon Green 488 conjugate (Invitrogen) for 30 min. After three washes, coverslips were mounted using mounting medium with DAPI. Micrographs were acquired at 200 Hz in the Analytic Microscopy Core at Moffitt Cancer Center using a Leica DMI6000 inverted microscope and TCS SP5 tandem confocal scanner, through a 63×/1.40NA Plan Apochromat oil immersion objective lens (Leica Microsystems) with triple photomultiplier tube detectors. Lasers, 405 diode (DAPI/Lysotracker Blue), 488 tunable argon (Green dye) and 543 diode (Rhodamine), were applied to excite the samples and a tunable emission filter was used to eliminate crosstalk between fluorochromes. LAS AF software version 2.1.0 (Leica Microsystems) was used to acquire and save the images using no compression of the original files.

Statistics:

Data are represented as mean±s.d. and Student's t-test was used to determine significance.

Results

Cells were needed that express CAIX and CAXII for in vitro as well as in vivo studies. MDA-mb-231 breast cancer cells constitutively express CAIX (Brennan, D. J. et al. *Clin Cancer Res* 12:6421-6431 (2006); Robey, I. F. et al. *Neoplasia* 7:324-330 (2005); Li, Y. et al. *Cancer Invest* 27:613-623 (2009)), but do not express the CA12 gene (and presumably the protein) as determined by qRT-PCR. Therefore, MDA-mb-231-luc cells were engineered to stably express CAXII as confirmed by qRT-PCR and ICC.

Monoclonal antibodies (mAbs) from R&D Systems that bind to the extracellular domain of CAIX and CAXII, respectively, were determined to be highly target specific by Western analysis and ICC, and were conjugated to a near-infrared (NIR) fluorescent dye (VivoTag-S® 680, VisEn). To verify the selectivity of the CAIX antibody-dye conjugate (CA9Ab-680), ICC was performed using the molecular probe on the CAIX constitutively expressing MDA-mb-231 cells and MCF-7 cells which do not express CAIX in normoxia condition as a negative control (Robey, I. F. et al. *Neoplasia* 7:324-330 (2005)). For CA12Ab-680, ICC was performed using MDA-mb-231 cells engineered to express CAXII (MDA-mb-231/CAXII) and the parental cells as a negative control. CA12Ab-680 bound only to expressing cells. Hence, the conjugated agents retained specificity for CAIX and CAXII proteins.

Example 3: In Vivo and Ex Vivo Selectivity Studies

Materials and Methods
Tumor Xenograft Studies:

To study selectivity of the CA9Ab-680 imaging probe, female nu/nu mice 6-8 weeks old (Harlan Sprague Dawley, Inc.) were implanted with $5 \times 10^6$ MDA-mb-231 (as CAIX expressing cells) in the right mammary fat pad (MFP). To study CA12Ab-680, the same procedure was done, except that MDA-mb-231/CAXII (as CAXII expressing cells) were implanted in the right MFP and MDA-mb-231 (as non-expressing cells) in the left MFP. Tumor volume was determined with calipers using the formula: volume=(length× width)/2. Once tumors reached 500-800 mm$^3$, 50 µg CA9Ab-680 in 100 µL sterile saline, was injected into the tail vein. In vivo fluorescence images were acquired using an IVIS 200 small animal imaging system (Caliper LifeSciences) using a 615-665 nm excitation filter and a 695-770 nm emission filter. According to the manufacturer, the excitation maxima of unconjugated VivoTag-S® 680 dye is 673±5 nm and the emission maxima is 691±5. Living Image 3.2 Software was used to draw regions of interest (ROIs) over the tumors to determine the mean tumor surface radiance (photons/sec/steradian/cm$^2$). Autofluorescence background was subtracted by determining the mean tumor fluorescence signal prior to injection.

Ex Vivo Studies:

One half of each excised tumor from animals was fixed in formalin and embedded in paraffin, the other half placed in Tissue-Tek Optical Cutting Temperature (OCT) cryoembedding media (Sakura Finetek) and snap frozen in liquid nitrogen. For histology, formalin fixed sections (5 µm) were stained with hematoxylin and eosin (H&E). Frozen sections were stained with the CA9Ab-680 and CA12Ab-680 using the ICC protocol described above. Sections were also stained with mammaglobin-A primary antibody as described above for TMAs.

Statistics:

Data are represented as mean±s.d. and Student's t-test was used to determine significance.

Results

To study the selectivity of the CA9Ab-680 in vivo, MDA-mb-231 cells that constitutively express CAIX were used to form a positive MFP tumor in nude mice. Since CAIX is expressed under hypoxic conditions, all tumors may express CAIX, including small metastases which may not have established vasculature. Therefore, a blocking experiment was used to determine specificity, where unlabeled CAIX mAb was added prior to CA9Ab-680.

For CA12Ab-680, MDA-mb-231/CAXII cells were used for generating the positive tumor in the right MFP, and parental cells were used for the negative left MFP tumor. After tumor growth to approximately 500-800 mm$^3$ in volume, agent was intravenously (i.v.) injected. CA9Ab-680 was retained in the CAIX positive MDA-mb-231 tumor 24 hours after injection, and that after blocking with unlabeled CAIX mAb, the amount of probe retained in the tumor was decreased. After blocking, the probe-related fluorescence signal decreased by 1.7 times relative to the unblocked tumor. The MDA-mb-231/CAXII tumor also retained high levels of the CA12Ab-680 compared to the CAXII negative xenograft. Expression in the CAXII positive tumor was quantified as having a 7.0±1.0 s.d. (n=3, p<0.001) fold greater fluorescence compared to the negative tumor. These results demonstrate the in vivo targeting specificity of the molecular probes.

For further confirmation, an ex vivo analysis was performed. Sections of flash-frozen tumors were stained with the probes, a nuclear stain, (DAPI), and a cell-surface/cytoplasmic stain, wheat germ agglutinin (WGA), and were imaged using confocal microscopy. CAIX staining was observed in the positive tumor, and was reduced by blocking with unlabeled mAb. CAXII staining was only observed in tumors from the positively expressing cell line but not in the negative line. Ex vivo images of the corresponding center sections of the tumors confirmed the in vivo results and allow comparison of probe signal relative to target expression in adjacent sections by IHC and histology.

Example 4: Pharmacokinetics and Biodistribution Studies

Materials and Methods
Pharmacodynamics and Biodistribution Studies:

Pharmacodynamics studies were performed by imaging at various time points. For biodistribution studies, mice were imaged and euthanized at 24 h and 48 h post-injection, tissues excised, rinsed with PBS, blotted dry, and then imaged ex vivo in the IVIS-200. A center slice cut from the tumor was imaged and the remaining halves were formalin fixed and fresh frozen, respectively, as described below. Mean surface radiance was determined for each tumor and organ. Autofluorescence background was subtracted using measurements from comparable tissues from an untreated animal.

Statistics:

Data are represented as mean±s.d. and Student's t-test was used to determine significance.

Results

Figure 2A:
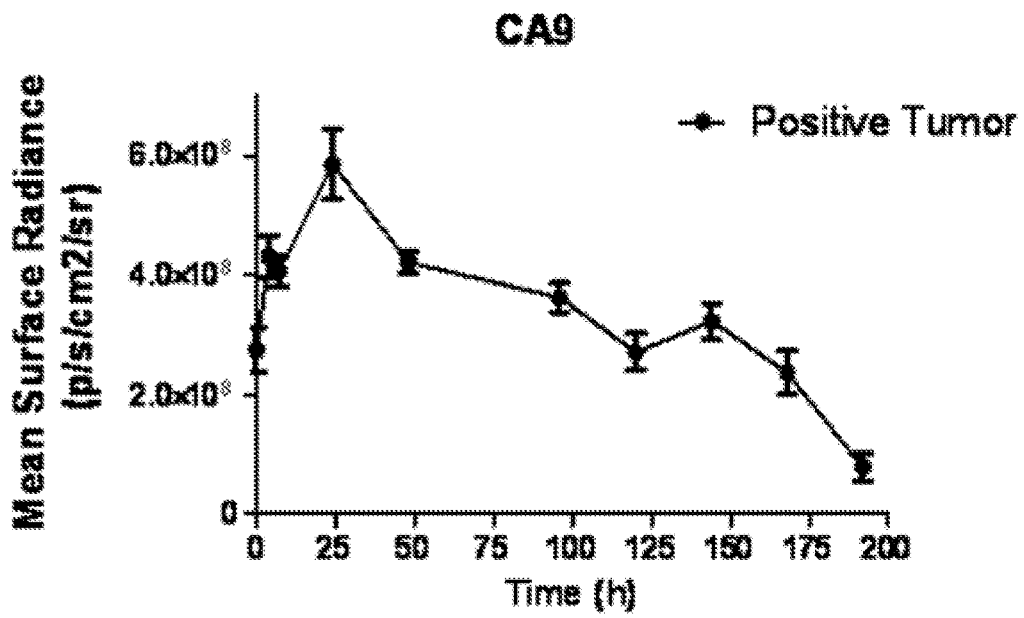
FIGS. 2A and 2B are graphs showing mean surface radiance (photons/sec/cm$^2$/steradian) as a function of time (hrs) for CA9Ab-680 (FIG. 2A) and CA12Ab-680 (FIG. 2B) antibodies in positive (●) and negative (■) mammary fat pad (MFP) tumors. Note that the peak signal in the positive Carbonic anhydrases 9 (CAIX) and 12 (CAXII) tumors is 24-hours post-injection, and that the agents are nearly cleared after 8 days. Data represent mean±s.d.
Figure 2B:
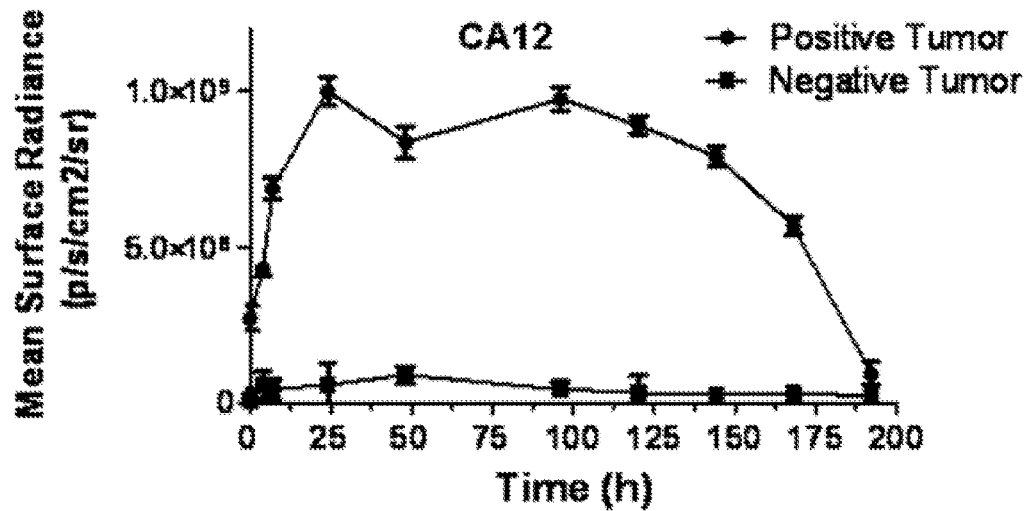

To evaluate the pharmacodynamics of probe uptake and clearance in the tumors, CA9Ab-680 and CA12Ab-680 were intravenously (i.v.) injected and images acquired at intervals from 5 minutes to 8 days post injection (FIGS. 2A and 2B). Fluorescence signal in positive tumors increased to a maximum at 24 hours following injection of both probes, and signal slowly cleared until approximately 7 days post-injection. Fluorescence signal in CAXII negative tumors increased slightly for about 24 hours and slowly cleared over the following 5 days.

Figure 2C:
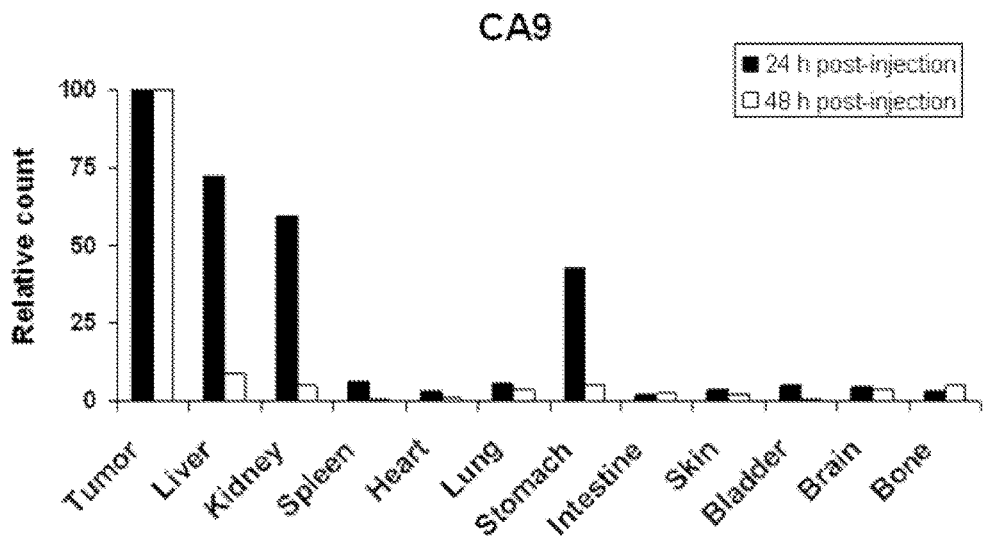
FIGS. 2C and 2D are bar graphs showing biodistribution (relative count) of CA9Ab-680 (FIG. 2C) and CA12Ab-680 (FIG. 2D) in tumors (FIG. 2C) or positive and negative tumors (FIG. 2D), liver, kidney, spleen, heart, lung, stomach, intestine, skin, bladder, brain, and bone 24 hours (solid bars) and 48 hours (open bars) post-injection. The values were normalized as percentage of the highest signal.
Figure 2D:
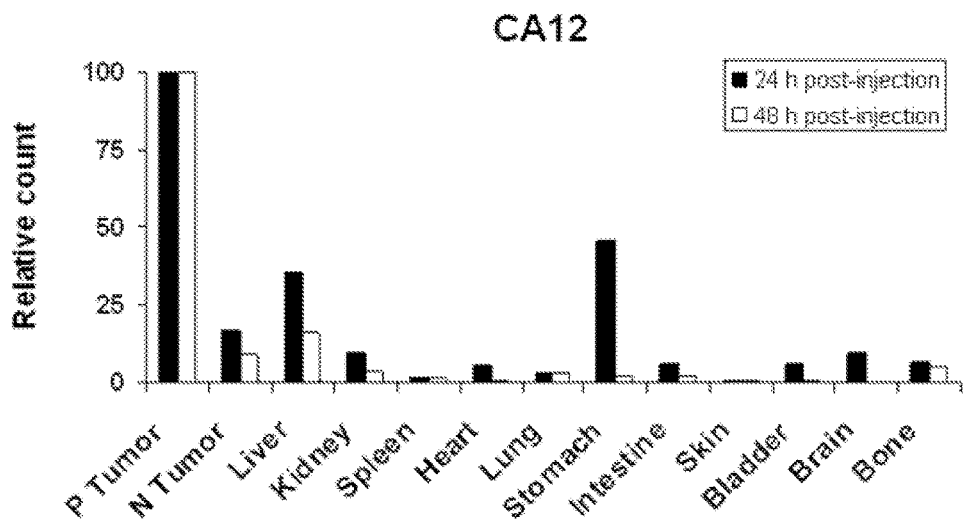

For biodistribution studies, mice bearing tumors were injected with probe, and tissue distribution of fluorescence signal determined after removing tumors and organs at 24-hours and 48-hours post-administration (FIGS. 2C and 2D). Twenty four hours post-injection, CA9Ab-680 and CA12Ab-680 retained at relatively high levels in the positive tumor relative to a corresponding negative tumor and other organs. However, the CAIX probe was elevated in liver, kidney and stomach and the CAXII probe was elevated in the liver and stomach. After 48 hours, probe had nearly cleared from all tissues except for positive tumors.

Example 5: Detection of Malignant Cells in ALNs Using CA9Ab-680 and CA12Ab-680 Imaging Probes Materials and Methods
Metastases to ALNs of Mouse Model:

For the CA9Ab-680 study, $5 \times 10^6$ luciferase expressing MDA-mb-231 cells were implanted into the right MFP of 6-8 weeks old female nu/nu mice. Eight to nine weeks later, bioluminescence imaging was used to follow metastasis formation in the ALN. Animals were anesthetized and 300 µl of D-luciferin potassium salt (GoldBio) was introduced via intraperitoneal (i.p.) injection. Five minutes after the injection, a bioluminescence image was acquired using standard bioluminescence settings on the IVIS 200. The same protocol was used for CA12Ab-680, except that MDA-mb-231 cells that express both luciferase and CAXII were used.

To determine agent sensitivity, precise numbers of cells were injected into ALNs using ultrasound image guidance. Female nu/nu mice (6-8 weeks old) were anesthetized with 3-4% isoflurane using a nose-cone manifold and restrained on the stage of a VEVO® 770 high-resolution small animal ultrasound imaging system (VisualSonics) using tape; ultrasound gel was applied to the area over the right axillary node; the 40 MHz ultrasound probe was placed in the probe guide and the node located by mechanically adjusting the probe guide to resolve the nodes; and a 1 cc syringe with a 29 gauge needle was loaded with 500 to 100,000 cells in a 20 µL volume of 1:1 matrigel and sterile PBS and positioned in the needle guide so that the end of the needle could be moved into the node and cells injected. Ultrasound images were acquired at the time of each injection. Four hours after injection of cells, animals were imaged using bioluminescence as described above. Twenty-four hour after injection of cells, 30 µg of agent was injected into the mammary fat pad proximal to axillary nodes, and fluorescence imaging was performed using the IVIS-200 as described above for pharmacodynamics and biodistribution studies.

Statistics:

Data are represented as mean±s.d. and Student's t-test was used to determine significance.

Results

To investigate whether the CAIX and CAXII molecular imaging probes can be delivered through the lymphatics and are selectively retained in positive ALNs, the MDA-mb-231-luc spontaneous metastasis model was used. After injecting cells in the MFP, ALN metastases were observed after 6-8 weeks by bioluminescence imaging. Probe was then injected peritumorally into the MFP and observed to traverse through the MFP into the lymph node within 4 hours. At 24 h post-injection, a strong fluorescence signal was obtained from the area of the ALN corresponding to a metastasis positive for the marker, and the probe had mostly cleared from the MFP. A specific and durable fluorescence signal was observed in target positive metastases out to at least 48 hours post-injection, long after completely clearing from the MFP. Probe was not retained in ALN metastases that did not express the target marker.

Figure 3A:
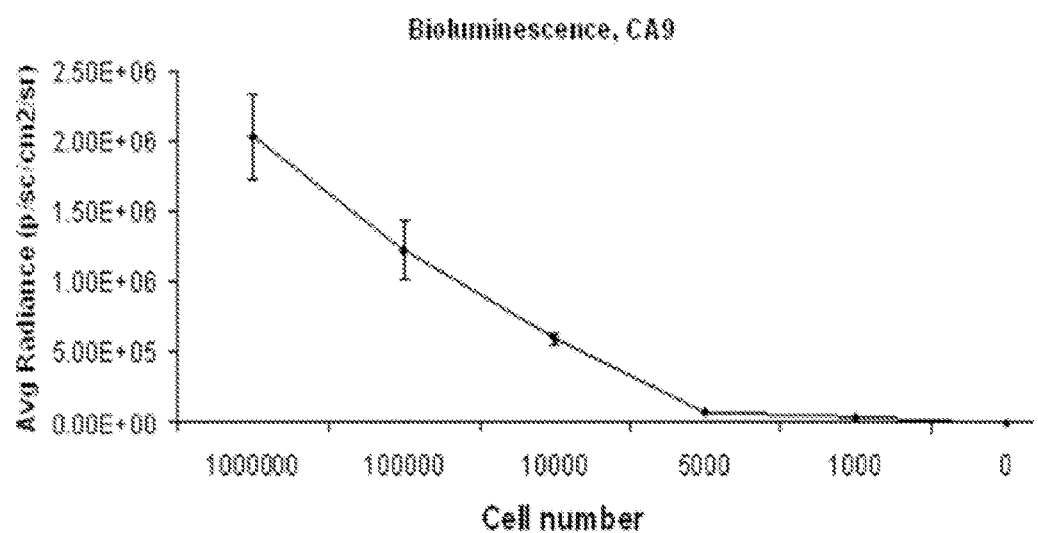
FIGS. 3A and 3B are graphs showing bioluminescence (average radiance (photons/sec/cm²/steradian)) of MDA-mb-231 cells expressing CAIX (FIG. 3A) or CAXII (FIG. 3B) four hours after injection into ALN of 6-8 weeks old female nu/nu mice as a function of the number of cells injected (1,000,000, 100,000, 10,000, 5,000, 1,000, or 0).
Figure 3B:
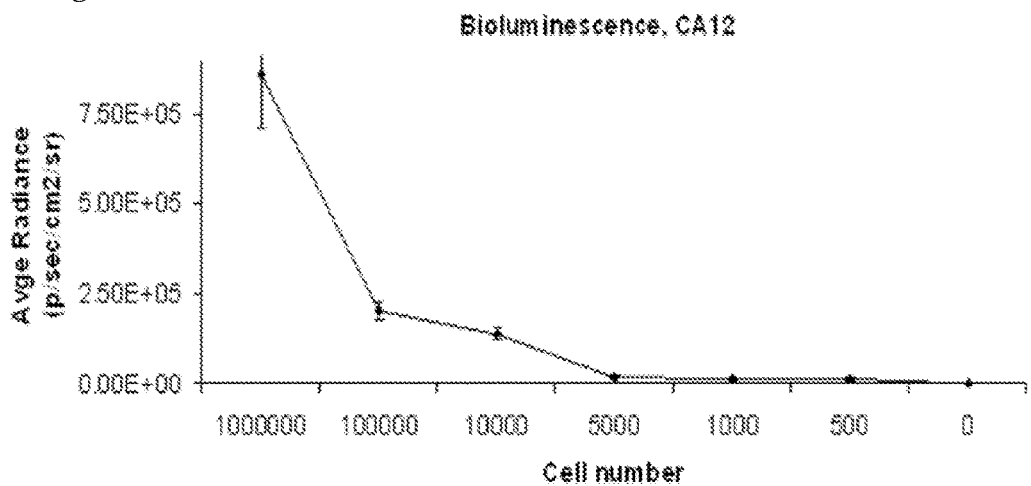
Figure 3C:
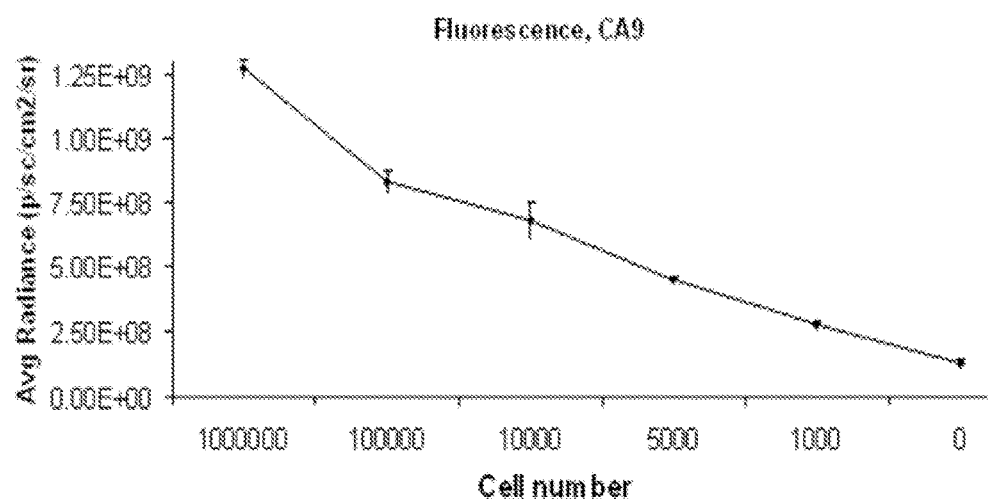
FIGS. 3C and 3D are graphs showing fluorescence (average radiance (photons/sec/cm²/steradian) 24 hours after injection of CA9Ab-680 (FIG. 3C) or CA12Ab-680 (FIG. 3D) into MFP of the mice of FIGS. 3A and 3B as a function of the number (1,000,000, 100,000, 10,000, 5,000, 1,000, or 0) of MDA-mb-231 cells expressing CAIX or CAXII injected into ALN. All data represent mean±s.d. of pixel values within the ROIs.
Figure 3D:
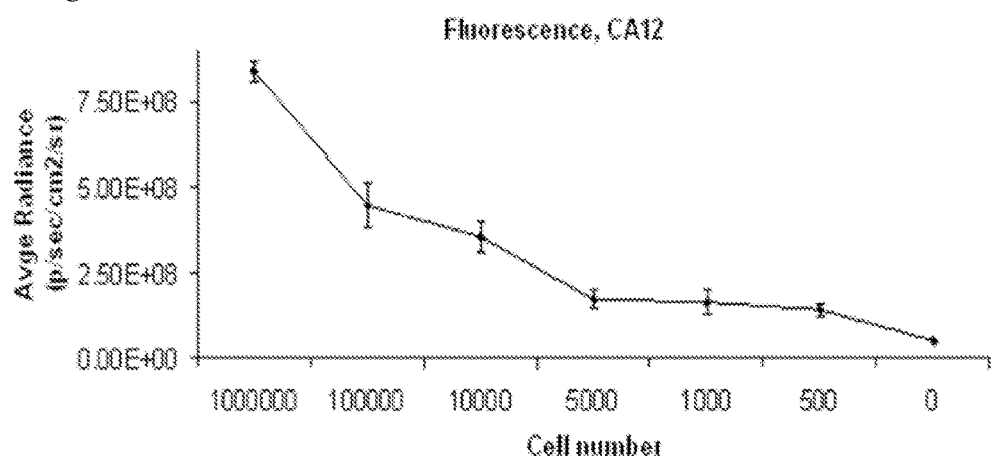
Figure 4A:
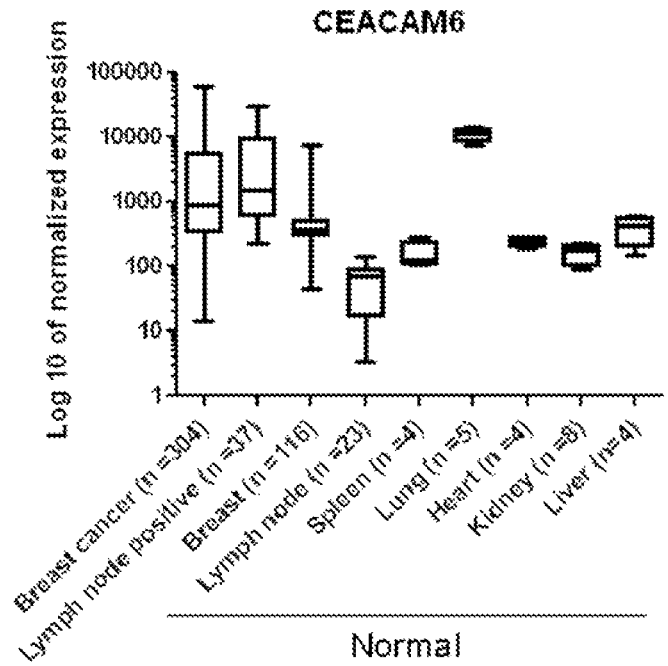
FIGS. 4A to 4D are bar graphs showing CEACAM6 (FIG. 4A), CXCL9, (FIG. 4B), CXCL10 (FIG. 4C), and MMP9 (FIG. 4D) mRNA expression (Log 10 of normalized expression) in breast cancer, lymph node positive, breast, lymph node, spleen, lung, heart, kidney, and liver samples. Data are represented as mean±s.d. Note the Log 10 scale.
Figure 4B:
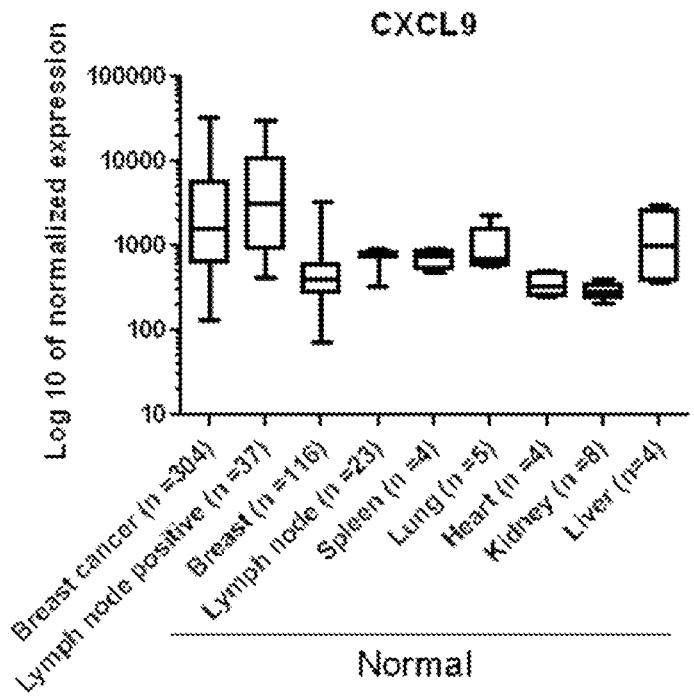
Figure 4C:
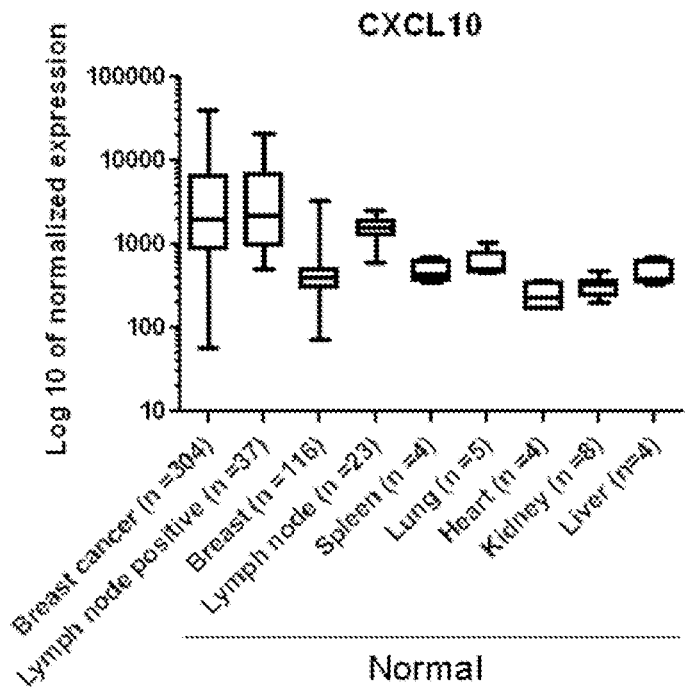
Figure 4D:
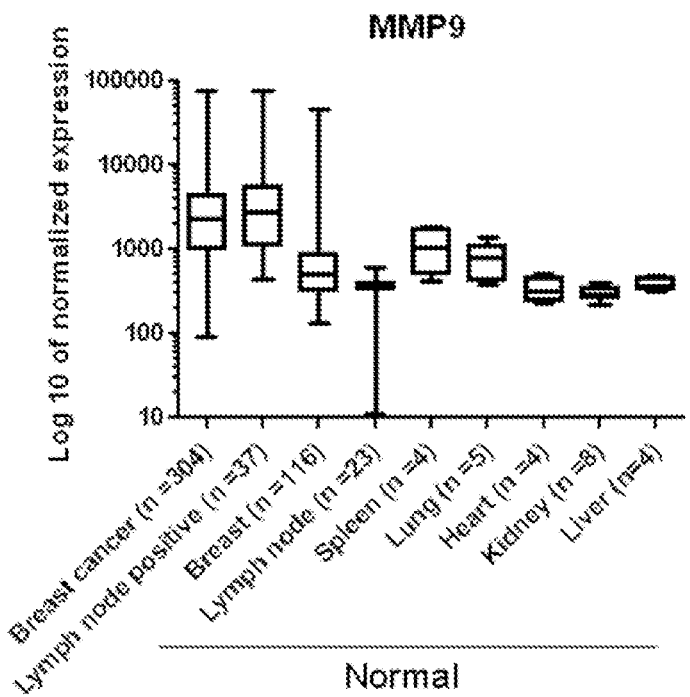

Agent selectivity and sensitivity for positive lymph nodes was also measured using an orthotopic model of lymph node metastasis. A range in number of MDA-mb-231/Luc cells that constitutively express CAIX but do not express CAXII, and a range of MDA-mb-231/Luc/CAXII cells (500 to 1 million) were directly injected into the ALN using ultrasound image guidance. For confirmation of successful cell implantation, cells were detected by bioluminescence imaging four hours after implantation. Twenty four hours after cell implantation, CA9Ab-680 and CA12Ab-680 were delivered by MFP injection and fluorescence images were acquired 24 hours after injection. Bioluminescence and fluorescence signals were quantified by drawing a region-of-interest (ROI) surrounding the tumor cells in the ALN. As expected, signal intensities for both bioluminescence and fluorescence decreased with cell number (FIGS. 3A-3D). With fluorescence, the CA12Ab-680 probe detected as few as 500 cells above background and CA9Ab-680 detected as few as 1000 cells (FIG. 3C-3D). When CA12Ab-680 was injected into the MFP of animals that were sham injected into the axillary lymph node with matrigel and PBS, probe was not retained at the 24 hour time point.

In conclusion, either CAIX or CAXII are expressed in 100% of lymph node metastasis from patients with breast cancer. CAIX and CAXII targeted molecular imaging probes were developed for non-invasive in vivo imaging and detection of breast cancer metastases in ALNs using small animal models. These imaging probes detected tumor cells in ALNs with high sensitivity. This targeted imaging strategy has potential for future translation into the clinic for ALN assessment and intraoperative surgical guidance as well as monitoring alteration in CAIX/CAXII expression as an indicator of treatment response. In the future, the agents may be improved by development of small targeting peptides and agents with theragnostic capability.

Example 6: CAIX and CAXII are Cell-Surface Markers for Non Small-Cell Lung Cancer (NSCLC)

Figure 5A:
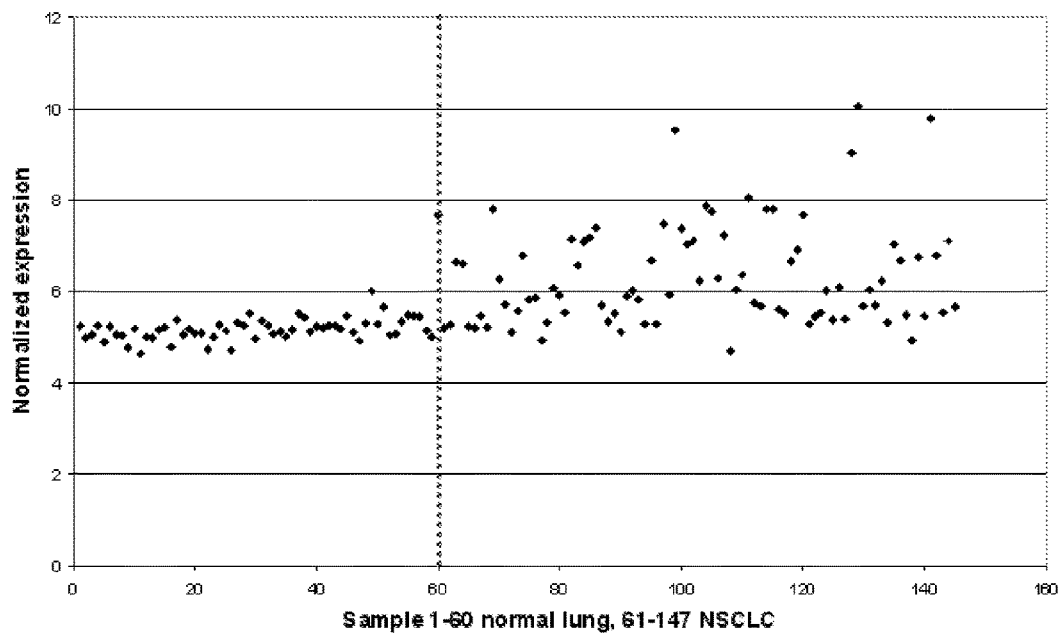
FIGS. 5A and 5B are plots showing CAIX (FIG. 5A) and CAXII (FIG. 5B) expression ($log_2$ normalized expression) in normal lung (samples 1-60) and adjacent non small-cell lung cancer (NSCLC) (samples 61-147) samples.
Figure 5B:
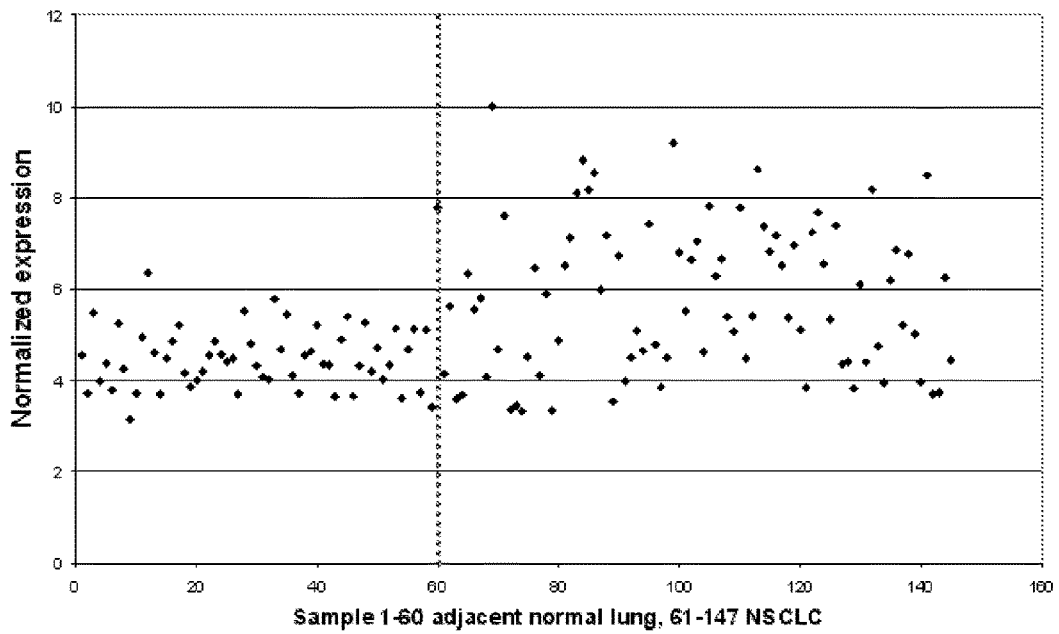

Expression profiling of CAIX and CAXII in 147 NSCLC patient samples, 87 from NSCLC tumors and 60 from adjacent normal lung, are shown in FIGS. 5A and 5B. NCBI Gene Expression Omnibus (GEO) dataset GSE19188, shows that CAIX is expressed higher in 45% of NSCLC tumors compared to the highest expression observed in any adjacent normal tissue in the dataset, and that CAXII is expressed higher in 39% of NSCLC tumors (FIGS. 5A and 5B). Hence, these markers may be general markers for cancer and imaging probes against these markers may be used for detection of cancer of the lung as well as breast, and possibly other cancer types as well.

Example 7: Mammaglobin-A Expression in Patient Tissue Samples

Materials and Methods

DNA Microarray Analysis:

Affymetrix expression data for the mammaglobin-A gene (SCGB2A2) in patient tissue samples were compiled from publicly available datasets. The CEL files for the tumor samples were downloaded from the Gene Expression Omnibus (GEO) database (http://www.ncbi.nlm.nih.gov/projects/geo/index.cgi), data series GSE2109. Normal tissue data were from the GEO data series GSE7307, Human Body Index. The CEL files were processed using the MAS 5.0 algorithm (Affymetrix, Santa Clara, Calif.) and screened through a rigorous quality control panel to remove samples with a low percentage of probesets called present by the MAS 5 algorithm, indicating problems with the amplification process or poor sample quality; high scaling factors, indicating poor transcript abundance during hybridization; and poor 3'/5' ratios, indicating RNA degradation either prior to or during processing. The remaining samples were normalized to the trimmed average of 500 in the MAS 5 algorithm before comparison of the expression values across tumors and normal samples.

Immunohistochemistry (IHC) of Tissue Mircroarray (TMA):

A TMA was constructed at the Moffitt Tissue Core, containing 50 normal breast tissue, 50 ductal carcinoma in situ, 50 invasive ductal carcinomas without metastasis, 50 invasive ductal carcinomas with metastasis and 50 lymph node with macrometastases of breast carcinoma. The same method was previously reported by our group for construction of a Ewing sarcoma TMA (Sharma, P. et al. *Chem Mater* 20:6087-6094 (2008)), except the breast TMA has only one sample per case. Mouse anti-mammaglobin-A mAb, 1:50, (Clone 304-1 A5, Thermo Scientific, Rockford, Ill.) was used for staining Positive staining was arbitrarily set as membranous (partial or complete) and cytoplasmic immunoreactivity in greater than or equal to 5% of tumor cells. Results were recorded as positive or negative.

Statistics:

Data are represented as mean±s.d. and the t-test was used to determine significance.

Results

Figure 6:
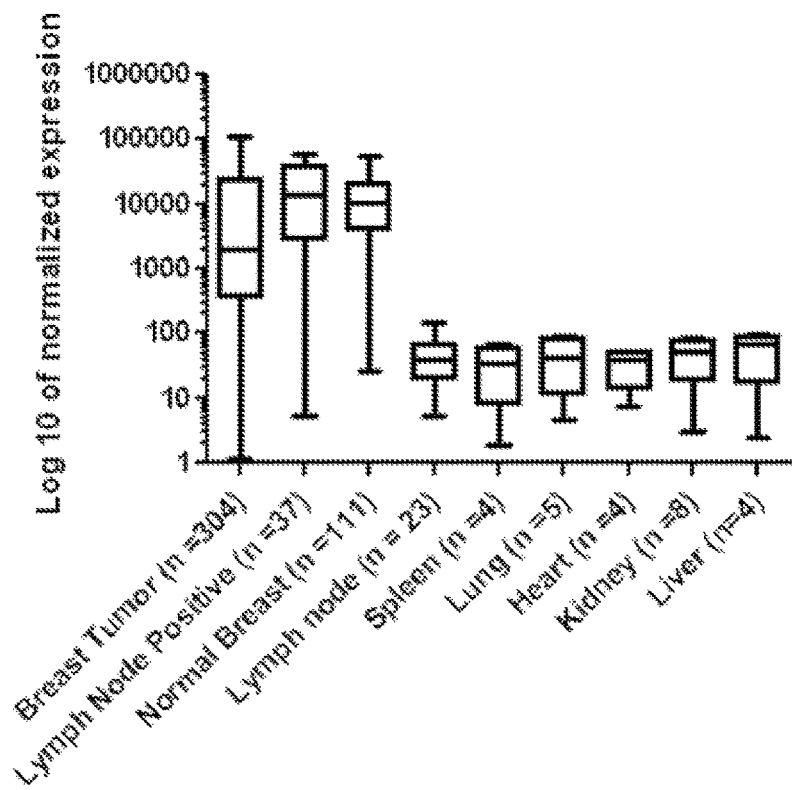
FIG. 6 is a bar graph showing Mammaglobin-A mRNA expression ($log_{10}$ of normalized expression) in breast cancer, lymph node positive, breast, lymph node, spleen, lung, heart, kidney, and liver samples. Data are represented as mean±s.d.

Several studies have demonstrated high expression of mammaglobin-A in breast cancer (Span, P. N. et al. *Br J Cancer* 89:271-276 (2003)). For further confirmation and to characterize mRNA expression in patient tissue samples, including lymph node metastases and normal tissues, publicly available DNA microarray data sets were analyzed. Mammaglobin-A mRNA was highly and generally expressed in breast tumors, breast cancer lymph node metastases and in normal breast (FIG. 6). A high percentage (83%) of lymph node metastases expressed mammoglobin-A. In contrast, mammaglobin-A was not expressed in normal lymph nodes. Also, other organs involved in toxicity or drug clearance, i.e., liver, kidney, heart, lung and spleen did not express mammaglobin-A mRNA.

To determine mammaglobin-A protein expression in patient samples, immunohistochemistry (IHC) was performed on a breast cancer tissue microarray containing 250 samples. Positive staining was observed in the ductal epithelium of 63% of normal breast tissues, 80% DCIS, 53% invasive ductal carcinoma without metastasis, 43% invasive ductal carcinoma with metastasis and 45% lymph node with macrometastasis of breast cancer.

Example 8: ZR-75.1 Breast Cancer Cells Express Mammaglobin-A

Materials and Methods

Stable Transfection of ZR-75.1 Cells:

The cells were transfected with 5 µg of pLenti PGK Blast V5-LUC luciferase containing vector (Addgene, Cambridge, Mass.) using the ViraPower lentiviral expression system (Invitrogen, Carlsbad, Calif.). In response to blasticidin (5 ug/ml), resistant colonies appeared. Clones were screened by adding medium containing 150 µg/ml D-luciferin potassium salt (GoldBioTechnology, St. Louis, Mo.) to the cells and the light detected by a Victor X4 2030 multiple plate reader (PerkinElmer, Waltham, Mass.).

Cell Culture:

Mammaglobin-A expressing ZR-75.1 (Robey, I. F. et al. *Neoplasia* 7:324-330 (2005); Goonewardene, T. I. et al. *Microsc Res Tech* 59:41-48 (2002); Ivanov, S. et al. *Am J Pathol* 158:905-919 (2001)) and non-expressing MDA-mb-231 (Ivanov, S. et al. *Am J Pathol* 158:905-919 (2001)) were obtained from and cultured according to ATCC recommendations.

Quantitative Real-Time RT-PCR:

Mammaglobin-A primers were designed using Gene Runner Software for Windows version 3.05: forward, 5'-CT-TCTTCAAGAGTTCATAGACGAC-3' (SEQ ID NO:3) and reverse, 5'-TGCTCAGAGTTTCATCCGTTTG-3' (SEQ ID NO:4). β-actin was used for normalization as described in our previous study (Sevick-Muraca, E. M. et al. *Radiology* 246:734-741 (2008)).

Results

ZR-75.1 breast cancer cells endogenously express mammaglobin-A (Robey, I. F. et al. *Neoplasia* 7:324-330 (2005); Goonewardene, T. I. et al. *Microsc Res Tech* 59:41-48 (2002); Ivanov, S. et al. *Am J Pathol* 158:905-919 (2001)) and MDA-mb-231 cells do not (Ivanov, S. et al. *Am J Pathol* 158:905-919 (2001)). To confirm this, mammaglobin-A mRNA expression was quantified by qRT-PCR in ZR-75.1 and MDA-mb-231 cells. As expected, mammaglobin-A was expressed in ZR-75.1 but not MDA-mb-231 cells. Western blot and immunocytochemistry (ICC) also confirmed protein expression.

Example 9: Antibody and MamAb-680 Characterization

Materials and Methods

Conjugation of Antibody to Dye:

Fifteen µg human Mammaglobin-A specific mouse mAb (Zeta Corp., California, Sierra Madre) was incubated with 10 µg VivoTag-S 680 (VisEn Medical, Bedford, Mass.) and purified with a Sephadex G25 column (Roche, Indianapolis, Ind.). Protein (A280) and dye (A680) absorbance was determined using an ND-1000 spectrophotometer (NanoDrop, Wilmington, Del.) and used to confirm the number of fluorophore molecules conjugated to each antibody molecule.

Results

The specificities of three different mammaglobin-A monoclonal antibodies were evaluated for sensitivity and specificity by Western blot and ICC. A highly specific mAb (Zeta Corp.) was selected for conjugation to near-infrared dye (VivoTag-S 680). The mAb conjugated with near-infrared dye is referred to herein as MamAb-680. To evaluate the antibody-dye conjugation and to verify that MamAb-680 retained binding specificity, ICC was performed using only the dye-labeled primary antibody on the endogenously expressing ZR-75.1 cells, MDA-mb-231 cells engineered to express mammaglobin-A and the non-expressing MDA-mb-231 cells. MamAb-680 bound only to mammaglobin-A expressing cells. Hence, the conjugated agent retained specificity for mammaglobin-A protein.

Example 10: Mammaglobin-A is Expressed on the Cell-Surface

Mammaglobin-A is directly associated with the surface of breast cancer cells (Supuran, C. T. et al. *Bioorg Med Chem* 15:4336-4350 (2007)). As described above, permeabilized fixed cells were used for ICC. To verify cell-surface expression, ZR-75.1 cells were incubated with MamAb-680 at 4° C. Agent was observed at the cell surface co-localized with agglutinin dye. Western blots of membrane protein extracts of mammaglobin-A positive cells stained positive for mammaglobin-A protein.

Example 11: MamAb-680 Selectively Accumulates in Positive Tumors

Materials and Methods

Microscopic Studies:

Cells and tissues from positive and negative xenograft tumors were fixed with cold methanol:acetone and incubated with 1 µg/µl MamAb-680 and 5.0 µg/mL of WGA (Invitrogen, Carlsbad, Calif.) for 30 min. After washing, coverslips were mounted. Micrographs were acquired using a Leica DMI6000 inverted microscope and TCS SP5 tandem confocal scanner (Leica Microsystems, Germany).

Statistics:

Data are represented as mean±s.d. and the t-test was used to determine significance.

Results

To determine the specificity of MamAb-680 targeting in vivo, ZR-75.1 and MDA-mb-231 cells were implanted in the right and left mammary fat pads (MFP) of female nude mice. After tumor growth to approximately 500-800 mm$^3$ in volume, MamAb-680 was intravenously (i.v.) injected.

ZR-75.1 tumors retained higher levels of the agent signal compared to MDA-mb-231. Fluorescence signal in the positive tumor was 8.6±0.8 s.d. (n=4, p<0.001) fold higher relative to the negative tumor. These results demonstrate the in vivo targeting specificity of MamAb-680.

To confirm the presence of mammaglobin-A protein in vivo, sections from flash-frozen tumors were stained with MamAb-680, a nuclear stain, 4',6-diamidino-2-phenylindole (DAPI), and a cell-surface/cytoplasmic stain, wheat germ agglutinin (WGA), and analyzed using confocal microscopy. Mammaglobin-A staining was observed in tumors from the positively expressing cell line but not in the negative line. Ex-vivo images of the corresponding center sections of the tumors confirmed MamAb-680 localization to the positive tumor relative to the negative tumor.

Example 12: Pharmacodynamics and Biodistribution of MamAb-680

Materials and Methods

Tumor Xenograft Studies:

Female nu/nu mice 6-8 weeks old (Harlan Sprague Dawley, Inc., Indianapolis, Ind.) were implanted subcutaneously with 0.72 mg of estradiol (Innovative Research of America, Sarasota, Fla.). After two days, 5×10$^6$ cells were implanted in the mammary fat pad. Once tumors reached 500-800 mm$^3$, 50 µg MamAb-680, in 100 µL saline, was injected into the tail vein. In vivo fluorescence images were acquired using an IVIS-200 small animal imaging system (Caliper LifeSciences, Hopkinton, Mass.) using a 615-665 nm excitation and a 695-770 nm emission filter. Living Image 3.2 Software was used to draw regions of interest (ROIs) over the tumors to determine the mean tumor surface radiance. Autofluorescence background was subtracted by determining the mean tumor fluorescence signal prior to injection. Pharmacodynamics studies were performed by imaging at various time points. For biodistribution studies, mice were euthanized at 24 h post-injection, tissues excised and imaged ex vivo in the IVIS-200.

Statistics:

Data are represented as mean±s.d. and the t-test was used to determine significance.

Results

Figure 7A:
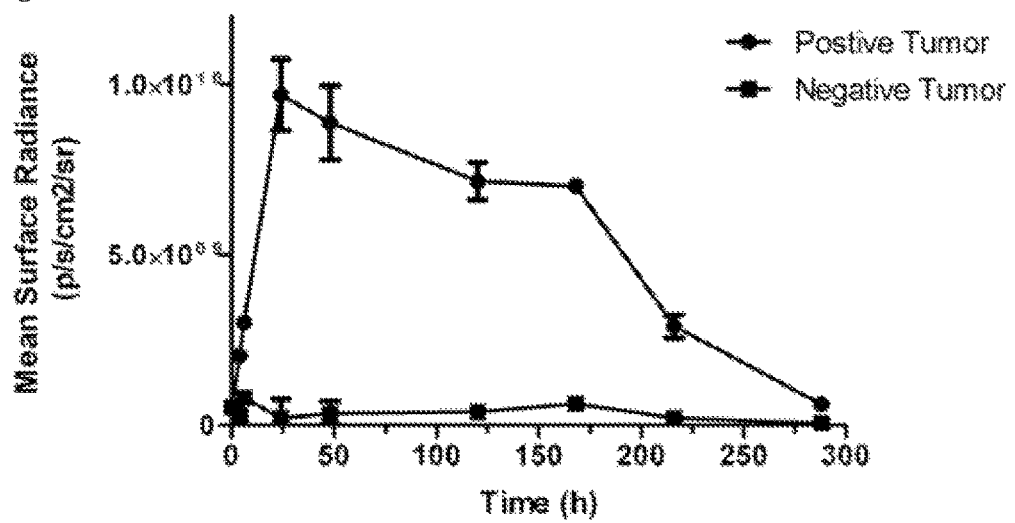
FIG. 7A is a graph showing mean surface radiance (photons/sec/cm²/steradian) as a function of time (hrs) for Mammaglobin-A antibodies (MamAb-680) in positive (●) and negative (■) mammary fat pad (MFP) tumors. Data represent mean±s.d.

To assess the pharmacodynamics of tumor uptake and clearance, MamAb-680 was injected intravenously (i.v.) and images acquired at intervals from 5 min to 12 d post injection. Fluorescence signal increased for 24 h and then slowly decreased at later time-points (FIG. 7A). Elevation of fluorescence in the positive tumor relative to the negative tumor was detected from 4 h to 10 days after injection.

Figure 7B:
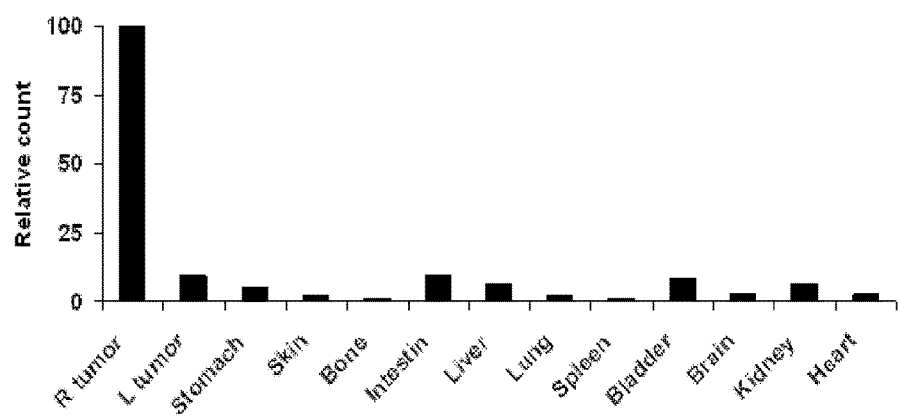
FIG. 7B is a bar graph showing bio-distribution (relative count) of MamAb-680 in Mamma-globin-A positive and negative tumors, stomach, skin, bone, intestine, liver, lung, spleen, bladder, brain, kidney, and heart 24 hours post-injection.

For biodistribution studies, MamAb-680 was i.v. injected into mammaglobin-A positive and negative tumor-bearing mice and, 24 h later, the tumors and organs were removed and imaged ex vivo. Fluorescence was present in the positive tumor but agent was largely cleared from the negative tumor and other organs (FIG. 7B).

Example 13: MamAb-680 Detects Tumor Cells in Axillary Lymph Nodes

Materials and Methods

Tumor Xenograft Studies:

see description in Example 12.

Orthotopic Implantation of Cells into ALN:

A range of 100 to 100,000 ZR-75.1/Luc cells in a 20 µL volume of 1:1 matrigel and PBS were injected into the axillary lymph node using image guidance by a VEVO 770 ultrasound imaging system (VisualSonics, Toronto, Canada). Four h after injection of cells, 300 µl of 15 mg/ml D-luciferin potassium salt was introduced via intraperitoneal injection and bioluminescence images were acquired using an IVIS-200. Twenty-four h after injection of cells, 50 µg MamAb-680 was injected into the mammary fat pad proximal to ALN, and fluorescence imaging was performed.

Statistics:

Data are represented as mean±s.d. and the t-test was used to determine significance.

Results

ZR-75.1 cells have not been reported to form ALN metastases. To determine this, 5×10$^6$ ZR-75.1/Luc cells were implanted into the right MFP of estrogen-pelleted mice. Three weeks after implantation, tumors were surgically removed. Two weeks later, the tumor had re-grown and bioluminescence imaging showed metastasis to the ALN. Hence, ZR-75.1 cells are a suitable model for ER+ breast cancer lymph node metastasis.

To investigate whether MamAb-680 can be delivered through the lymphatics to selectively bind positive nodes, the agent was injected peritumorally into the MFP. At 24 h post-injection, the area of the ALN showed a strong fluorescence signal, which co-localized with the bioluminescence image of the luciferase expressing metastases. After imaging, the metastases was removed and the presence of cancer cells confirmed by H & E staining and pathological examination.

Agent selectivity was also determined for positive lymph nodes using an orthotopic model of lymph node metastasis. ZR-75.1/luc cells were directly injected into the ALN using ultrasound image guidance and were detected by bioluminescence. MamAb-680 was delivered by MFP injection and was observed to have traversed to the lymph node within 4 h. Fluorescence signal was retained in lymph nodes implanted with mammaglobin-A positive cells long after clearance from the MFP and negative lymph nodes. Positive lymph nodes were resolved as early as 4 h and were detected up to at least 7 days post-injection. These results show that in vivo lymphatic imaging using MamAb-680 provided a specific and durable signal in mammaglobin-A expressing lymph node metastases.

As a control, animals were injected with PBS and Matrigel (no cells) into the ALN using the same method and amounts used above, then injected MamAb-680 into the MFP and imaged. Minimal signal was detected in the draining lymphatics at 4 h post-injection and no signal was observed at 24 h. At 48 h, agent was cleared from the animal.

To determine the sensitivity of the agent, a range in number of ZR-75.1/luc (1000 to 1 million) were injected into ALN via ultrasound guidance. For confirmation of successful cell implantation, bioluminescence images were acquired and as few as 1,000 cells (FIG. 8A) detected. Four hours after cell injection, MamAb-680 were injected into mammary fat pad proximal to the ALN and acquired fluorescence images 24 h after injection (FIG. 8B) and bioluminescent and fluorescent signals quantified by drawing a region-of-interest (ROI) encompassing the tumor cells in the ALN. Signal intensity decreased with cell number and at least 1,000 cells were detectable above background (FIG. 8B).

Mammaglobin is expressed in malignant breast tissues and is not expressed in normal lymph node (LN) or skin, as determined by DNA and tissue microarray. A mammaglobin targeted imaging probe has therefore been developed. Three monoclonal antibodies (mAbs) were compared by immunostaining of cells, tissues and Western analysis. One highly specific mAb was conjugated to a near-infrared dye (VivoTag 680, VisEn) and intravenously injected into nude mice bearing bilateral mammary fat pad (MFP) tumors of mammaglobin-positive (ZR-75.1) and mammaglobin-negative (MDA-mb-231) cells. In vivo fluorescence imaging showed agent was retained only in ZR-75.1 tumors. Selectivity for positive LNs was determined by implanting ZR-75.1/luc cells in the axillary LN using ultrasound guidance and monitoring by bioluminescence Labeled mAb was delivered by MFP injection and traversed to LN. Label was retained in mammaglobin-positive LNs long after clearance from the MFP and negative LNs.

Example 14: Combination with Other Antibodies

Materials and Methods

DNA Microarray Analysis:

Affymetrix expression data for the mammaglobin-A gene (SCGB2A2) in patient tissue samples were compiled from publicly available datasets. The CEL files for the tumor samples were downloaded from the Gene Expression Omnibus (GEO) database (http://www.ncbi.nlm.nih.gov/projects/geo/index.cgi), data series GSE2109. Normal tissue data were from the GEO data series GSE7307, Human Body Index. The CEL files were processed using the MAS 5.0 algorithm (Affymetrix, Santa Clara, Calif.) and screened through a rigorous quality control panel to remove samples with a low percentage of probesets called present by the MAS 5 algorithm, indicating problems with the amplification process or poor sample quality; high scaling factors, indicating poor transcript abundance during hybridization; and poor 3'/5' ratios, indicating RNA degradation either prior to or during processing. The remaining samples were normalized to the trimmed average of 500 in the MAS 5 algorithm before comparison of the expression values across tumors and normal samples.

Immunohistochemistry (IHC) of Tissue Mircroarray (TMA):

A TMA was constructed at the Moffitt Tissue Core, containing 50 normal breast tissue, 50 ductal carcinoma in situ, 50 invasive ductal carcinomas without metastasis, 50 invasive ductal carcinomas with metastasis and 50 lymph node with macrometastases of breast carcinoma. The same method was previously reported by our group for construction of a Ewing sarcoma TMA (Sharma, P. et al. *Chem Mater* 20:6087-6094 (2008)), except the breast TMA has only one sample per case. Mouse anti-mammaglobin-A mAb, 1:50, (Clone 304-1 A5, Thermo Scientific, Rockford, Ill.) was used for staining Positive staining was arbitrarily set as membranous (partial or complete) and cytoplasmic immunoreactivity in greater than or equal to 5% of tumor cells. Results were recorded as positive or negative.

Statistics:

Data are represented as mean±s.d. and the t-test was used to determine significance.

Results

To identify more targets, 3800 cell surface genes were curated from Gene Bank and used to filter DNA microarray data from 304 breast tumors (38 node positive), 111 normal breast tissues, 15 LNs, and 189 samples from 6 unaffected organ sites in the area surrounding the LNs and involved in clearance and toxicity. Of all genes, CA-9 and CA-12 were seen to be highly expressed in breast and LN-positive cancers but not in the normal tissues. Immunohistochemistry was performed on 50 normal breast tissues, 50 DCIS, 50 IDCs without metastasis, 50 IDCs with metastasis and 50 LN macrometastases. Nearly all (95%) of LN metastases expressed either CAIX or CAXII (Table 2). Thus, these CAs are valid targets for imaging of LN status for breast cancer.

TABLE 2

Coverage of breast cancer samples in the Moffitt breast cancer tissue microarray, including LN metastases, by three cell-surface markers, individually and in combination.

| | Mammaglobin | CA9 | CA12 | Combination |
|---|---|---|---|---|
| DCIS | 80.0% | 71.4% | 81.3% | 100% (n = 9) |
| IDC without Mets | 53.1% | 55.8% | 78.7% | 100% (n = 28) |
| IDC with Mets | 42.9% | 56.5% | 80.4% | 93% (n = 26) |
| LN Macro Mets | 45.2% | 71.4% | 75.5% | 100% (n = 31) |

Note that the three markers, mammaglobin, CA9 and CA12 cover 100% of the lymph node metastases (n = 51) on the tissue microarray

Example 15: In Vitro Identification and Functional Characterization of TLR2 Ligands Materials and Methods Peptides, Antibodies, and Tetramers The test compounds (359, 360, 361, 362, 363, T-02, T-03, T-05) were synthesized and prepared with high purity. Lyophilized compounds were dissolved in DMSO at a 1 mg/mL concentration as stock solutions stored at −20° C. For biological experimental use, 10 μg/mL working solutions of the compounds were prepared from stock solutions in sterilized, deionized water and used immediately. Commercially available synthetic TLR-2 agonists were used as references: Pam2CSK4 and Pam3CSK4 were purchased from InvivoGen (San Diego, Calif.) and recombinant human apo-SAA1 was purchased from Peprotech (Rocky Hill, N.J.).

Cell Culture

For the in vitro TLR2 bioassay, the parental HEK293 cells (ATCC, Manassas, Va.) were cultured in DMEM/F12 media (Invitrogen, Carlsbad, Calif.) supplemented with 10% normal calf serum (Atlanta Biologicals, Lawrenceville, Ga.) and 1% penicillin/streptomycin solution (Sigma, St. Louis, Mo.). The commercially purchased HEK293/hTLR2 cells (InvivoGen, San Diego, Calif.), which are HEK293 cells stably transfected with pUNO-hTLR2 plasmid expressing the human TLR2 gene (Zuany-Amorim, C., J., et al. *Nat Rev Drug Discov,* 2002. 1(10):797-807), were cultured in DMEM/F12 media supplemented with 10% normal calf serum, 1% penicillin/streptomycin solution, 10 ug/mL blasticidin (InvivoGen). All cells were grown at 37° C. and 5% $CO_2$.

RT-PCR

HEK293/hTLR2 and the parental HEK293 cells were seeded in T-25 flasks and grown to approximately 80% confluency. RNA was extracted from the cells using the GenElute Mammalian Total RNA Mini Prep kit (Sigma Aldrich). The RNA was treated with DNASE (Applied Biosystems Ambion, Austin, Tex.) then the RNA concentration was determined using the Nanodrop. Next, the RT-PCR was run using Superscript First-strand Synthesis System kit for RT-PCR (Invitrogen) and a Biorad PCR machine. The sequence for the forward TLR2 primer was TCTCCCA-GTGTTTGGTGTTG (SEQ ID NO:7); while the sequence for the reverse TLR2 primer was TGGTGTTCATTATCT-TCCGCAG (SEQ ID NO:8). The DNA samples were run on a 1% agarose gel with ethidium bromide and a 1 kb ladder.

Western Blot

Western blot was performed under standard denatured and reduced conditions. The samples, HEK293 cells and HEK293/htlr2 p3 cells, were prepared by growing up cells on 10 cm petri dishes until 90% confluency was reached. The cells were lysed using RIPA Lysis and Extraction Buffer (Thermo Fisher Scientific Pierce) with Halt Protease Inhibitor Cocktail (Thermo Fisher Scientific Pierce). The protein concentrations of the cell lysates were measured by Pierce BCA Assay. The samples were then prepared for loading onto the SDS-PAGE gel by mixing 1:1 with 2× Laemmilli Sample Buffer and boiled for 5 min at 95° C. 30 µg per well of each cell lysate (n=3) was loaded onto a 10% Tris-glycine readymade gel (Invitrogen Novex). A molecular weigh marker (Biorad) was used. The gel ran at 125V for 90 min. The protein was then transferred from the gel to 0.4 micron nitrocellulose membrane (BioRad) for 2 hrs at 25V at 4° C. After the transfer, the nitrocellulose blot was stained to check the transfer efficiency (Thermo Fisher Scientific Pierce). Membrane was blocked with 5% BSA/TBST blocking solution for 1 h, then washed for 5 min with TBST, incubated for 2 h with goat anti-TLR2 pAb (Abcam) at ½₀₀₀ dilution, 3× wash with TBST for 15 min each, incubated with rabbit anti-goat (Abcam) at ⅕₀₀₀ dilution for 1 hr, 3× wash with TBST for 15 min each. The blot was then developed using ECL Western Blotting Detection Kit efficiency (Thermo Fisher Scientific Pierce). The developed blot was then stripped using a stripping buffer so that the B-actin loading control could be shown. After stripping the blot, the blot was again developed to show that it had been successfully stripped of the previous antibodies. Next, it was then blocked for 1 hr with 5% BSA/TBST, then washed for 5 min with TBST, incubated for 2 hrs with goat anti-B-Actin pAb (Abcam) at ¹⁄₁₀₀₀ dilution, 3× wash with TBST for 15 min each, incubated with rabbit anti-goat at ⅕₀₀₀ dilution for 1 hr, 3× wash with TBST for 15 min each. The blot was then developed using ECL Western Blotting Detection Kit. The methods above were optimized conditions.

In Vitro TLR2 Functional Bioassay

The in vitro TLR2 functional bioassay was developed and optimized for use in screening soluble compound libraries to identify both TLR2 agonists and antagonists. In this study, the TLR2 functional bioassay was used as a fast high throughput screening to identify TLR2 agonist ligands by measuring the inducing activity of NF-κB. HEK293/hTLR2 cells, highly overexpressing human TLR2, were used along with the parental HEK293, cells as a negative control. Cells were seeded at a density of 40,000 per well using a WellMate® Microplate dispenser (Thermo Fischer Scientific/Matrix) in black 96-well plates with opaque white wells (Perkin Elmer Wallac, Waltham, Mass.) and then incubated at 37° C. On day 2, the cells were transiently transfected with pNifty-Luc (InvivoGen), an NF-κB inducible reporter plasmid expressing the luciferase reporter gene (Zuany-Amorim, C., J., et al. Nat Rev Drug Discov, 2002. 1(10): 797-807), using an optimized 4:1 ratio by volume of Fugene® HD Transfection Reagent (Roche Applied Science, Indianapolis, Ind.) to pNifty-Luc plasmid DNA (1 µg/mL). On day 3, the cells were stimulated with either test peptides or controls adjusted to a final concentration of 1 µg/mL using a NanoDrop Spectrophotometer, ND1000 (Thermo Fisher Scientific). On day 4 after 24 hrs of peptide stimulation, luciferase induced activity by the induction of NF-κB was measured. Media was aspirated from the wells using an ELx405 Select plate washer (BioTek, Winooski, Vt.), 150 µg/mL D-luciferin (Gold Biotechnology, St. Louis, Mo.) was dispensed using the microplate dispenser; the plates were incubated at 37° C. for 5 min. The luminescence intensity was measured using the standard luminescence protocol on a Victor™ X4 plate-reader equipped with a plate stacker for readout of multiple plates at a time (PerkinElmer, Waltham, Mass.). For each in vitro TLR2 bioassay, at least three different experiments were performed in triplicate (n=3+). Data were analyzed with GraphPad Prism software and curves were generated with the appropriate nonlinear fit regression analysis.

Statistical Analysis

The results were represented as mean±s.d. and statistically evaluated by the Student's t test to determine statistical significance.

Results

Figure 9:
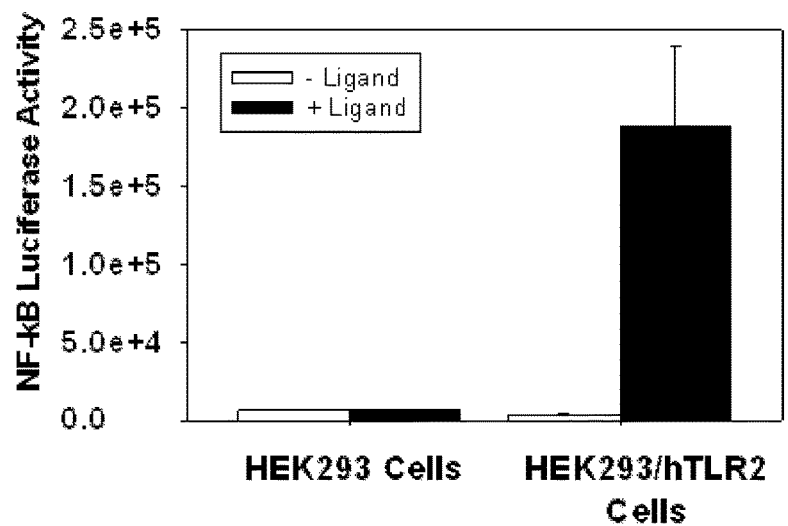
FIG. 9 is a bar graph showing Toll-like receptor 2 (TLR2) activity (luciferase bioluminescence) in HEK293 controls cells (first set of bars) or HEK293/hTLR2 cells (transfected with expression vector (TLR2-NF-κB-luc) containing the luciferase gene under control of an NF-κB activatable promoter) (second set of bars) that were either untreated (open bars) or treated with Pam3CSK4 (solid bars). n=6, p<0.001 by t-test.

To identify TLR2 ligands with high activity and a built-in site for attachment of imaging contrast or therapeutic agents for the detection or treatment of pancreatic cancer, an in vitro high-throughput functional bioassay was developed to screen agonist ligand libraries for TLR2 activity. The assay was optimized prior to screening using the commercially available synthetic ligand Pam3CSK4, which induces TLR2 signaling to produce NF-κB. An expression vector containing the luciferase gene under control of an NF-κB activatable promoter was transfected into HEK293/hTLR2 cells. Optimal luciferase activity was observed 48 h post transient transfection and 24 h post ligand stimulation (FIG. 9). Luciferase activity was significantly greater (50 fold, n=6, p<0.001 by t-test) in Pam3CSK4 ligand stimulated HEK293/hTLR2 cells relative to HEK293/hTLR2 cells incubated with no ligand; while the ligand stimulated HEK293 cells did not exhibit any significant NF-κB luciferase activity. Therefore, the measured luciferase activity via NF-κB induced activity is not due to non-specific interactions. Expression of human TLR2 in the HEK293/hTLR2 cells relative to the parental HEK293 cells was confirmed by RT-PCR and Western blot.

The TLR2 functional bioassay was used to screen a set of seven X-Dhp(Pam2)-peptide MALP2 compounds to identify TLR2 agonist ligands (Table 3). These X-Dhp(Pam2)-peptide MALP2 compounds (1-7 in Table 6; 357-363 in Table 3) are fully synthetic soluble compounds that were designed using the commercially available synthetic TLR2 agonist peptide ligand, Pam2CSK4 (Invivogen), as a template. Pam2CSK4 (S-[2,3-bis(palmitoyloxy)-(2RS)-propyl]-[R]-cysteinyl-[S]-seryl-[S]-lysyl-[S]-lysyl-[S]-lysyl-[S]-lysine) is a commercially available synthetic diacylated lipopeptide (LP). Typically, Pam2CSK4 and other diacylated LPs activate the formation of heterodimers between TLR2 and TLR6. Each compound in the set had the same scaffold, X-Dhp(Pam2)-peptide MALP2, where "X" represents an N-terminal manipulation for each compound. "X" represents the addition of: Palmitoyl (C16) for compound 1, Fluorescein for compound 2, Ac-PEGO20 for compound 3, Ac-Aha (C6) for compound 4, Adapaleneyl for compound 5, Ac-Aun (C11) for compound 6, and Tretinoyl for compound 7. Palmitoyl was chosen for 1 because palmitoyl groups are the most common type of lipid chain in bacterial lipoproteins (Belisle, J. T., et al. *J Bacteriol*, 1994. 176(8):2151-7; Mizuno, T., et al. *J Biochem*, 1979. 86(4):991-1000; Zlotnick, G. W., et al. *J Biol Chem*, 1988. 263(20):9790-4; Braun, V., et al. *Biochim Biophys Acta*, 1975. 415(3):335-77).

TABLE 3

X-Dhp(Pam2)-peptide MALP2 derived synthetic compound library set

| Compound | Structure | X Modification | Molecular Weight (g/mole) | TLR2 Agonist Activity |
|---|---|---|---|---|
| 357 | Pam-Dhc(Pam)$_2$-Gly-Asn-Asn-Asp-Glu-Ser-Asn-Ile-Ser-Phe-Lys-Glu-Lys-NH$_2$ (SEQ ID NO: 10) | Palmitoyl (C16) | 2371.4 | Yes |
| 358 | Fluorescein-Dhc(Pam)$_2$-Gly-Asn-Asn-Asp-Glu-Ser-Asn-Ile-Ser-Phe-Lys-Glu-Lys-NH$_2$ (SEQ ID NO: 10) | Fluorescein | 2491.3 | Yes |
| 359 | Ac-PEGO20-Dhc(Pam)$_2$-Gly-Asn-Asn-Asp-Glu-Ser-Asn-Ile-Ser-Phe-Lys-Glu-Lys-NH$_2$ (SEQ ID NO: 10) | Ac-PEGO20 | 2493.4 | Yes |
| 360 | Ac-Aha-Dhc(Pam)$_2$-Gly-Asn-Asn-Asp-Glu-Ser-Asn-Ile-Ser-Phe-Lys-Glu-Lys-NH$_2$ (SEQ ID NO: 10) | Ac-Aha (C6) | 2288.3 | Yes |
| 361 | Adapalene-Dhc(Pam)$_2$-Gly-Asn-Asn-Asp-Glu-Ser-Asn-Ile-Ser-Phe-Lys-Glu-Lys-NH$_2$ (SEQ ID NO: 10) | Adapaleneyl | 2526.4 | Yes |
| 362 | Ac-Aun(C11)-Dhc(Pam)$_2$-Gly-Asn-Asn-Asp-Glu-Ser-Asn-Ile-Ser-Phe-Lys-Glu-Lys-NH$_2$ (SEQ ID NO: 10) | Ac-Aun (C11) | 2358.4 | Yes |
| 363 | Tretinoin-Dhc(Pam)$_2$-Gly-Asn-Asn-Asp-Glu-Ser-Asn-Ile-Ser-Phe-Lys-Glu-Lys-NH$_2$ (SEQ ID NO: 10) | Tretinoyl | 2414.4 | Yes |

The structure activity relationships (SAR) of the compound set was investigated by manipulating the N-terminus portion of the peptide to enhance specificity, potency, and binding to TLR2 expressed on the cell surface. Synthetic LPs containing di- or tri-acylated cysteine groups are known mimic lipoprotein proinflammatory properties; indicating the acylated N-terminal cysteine is the most critical portion of the immune stimulatory motif (Bessler, W. G., et al. *J Immunol*, 1985. 135(3):1900-5; Berg, M., et al. *Am J Physiol*, 1994. 266(6 Pt 1):C1684-91; Seifert, R., et al. *Biochem J*, 1990. 267(3):795-802). Wu et al closely examined the roles of the highly conserved Cys reside and Cys-Ser dipeptide unit using a human TLR2 reporter gene assay (Takeda, K., et al. *Annu Rev Immunol*, 2003. 21:335-76). They concluded that (R)-diacylthioglycerol analogues are maximally active. Others have reported that the Cys-Ser dipeptide unit is the minimal structure for biological activity (Wu, W., et al. *J Med. Chem*. 53(8):3198-213; Prass, W., et al. *Biochim Biophys Acta*, 1987. 900(1):116-28) and the thioether bridge between the diacyl and dipeptide units is crucial (Takeda, K., et al. *Annu Rev Immunol*, 2003. 21:335-76).

Figure 10:
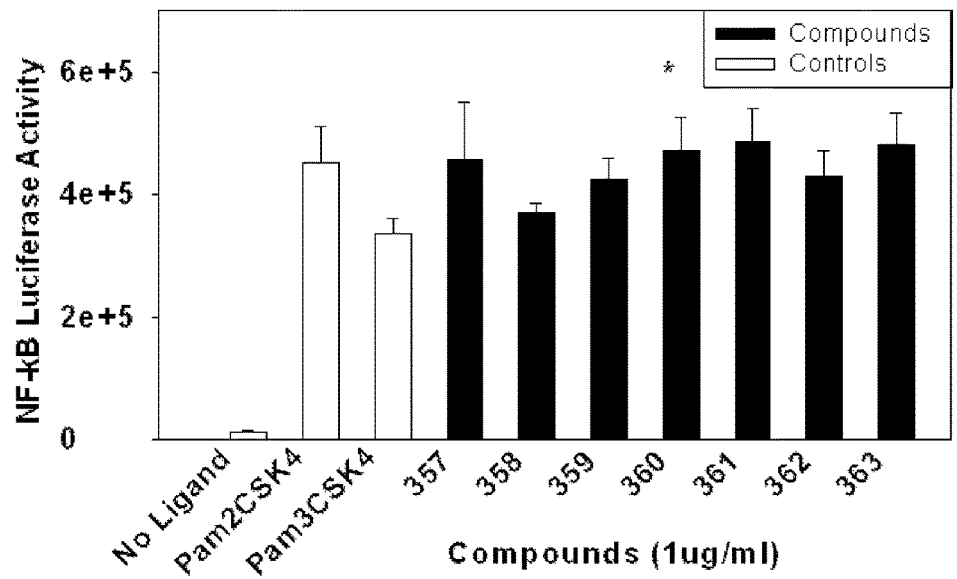
FIG. 10 is a bar graph showing TLR2 activity (luciferase bioluminescence) in HEK293/hTLR2 cells treated with no ligand, control ligand Pam3CSK2 or Pam3CSK4, or one of seven X-Dhp(Pam2)-peptide MALP2 compounds (357, 358, 359, 360, 361, 362, 363). n=3 assays with quadruplicate wells, p value<0.0003

All seven of the compounds exhibited high levels of NF-κB induced luciferase activity when screened using the TLR2 functional bioassay comparable to the reference TLR2 agonist ligand controls, Pam2CSK4 and Pam3CSK4 (FIG. 10). Typically, Pam2CSK4 and other diacylated LPs activate the formation of heterodimers between TLR2 and TLR6. However, TLR2 is also recognized by some diacylated LPs, such as Pam2CSK4, to induce signaling in a TLR6-independent manner according to murine model studies suggesting that both the lipid and peptide portion of the LP play a role in the recognition of TLR2 heterodimers (Buwitt-Beckmann, U., et al. *FEBS J*, 2005. 272(24):6354-64; Buwitt-Beckmann, U., et al. *Eur J Immunol*, 2005. 35(1):282-9). Pam3CSK4 (N-Palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine) is a synthetic tripalmitoylated LP that mimics the acylated amino terminus of bacterial LPs. It is a highly potent activator of NF-κB through induction of a signaling cascade by the recognition of the heterodimerization of TLR2 with TLR1 and also independently of TLR6 (Aliprantis, A. O., et al. *Science*, 1999. 285(5428):736-9; Ozinsky, A., et al. *Proc Natl Acad Sci USA*, 2000. 97(25):13766-71; Takeuchi, O., et al. *Int Immunol*, 2001. 13(7):933-40; Takeuchi, O., et al. *J Immunol*, 2002. 169(1):10-4). In the screenings the positive agonist ligand controls, Pam2CSK4 and Pam3CSK4, did not exhibit significant NF-κB induced luciferase activity in the non-expressing TLR2 cell line, HEK293. This indicated that the NF-κB induced luciferase activity was specifically due to the TLR2 agonist ligand that specifically binds and activates TLR2s and was not due to non-specific interactions. Based on these results, all seven X-DhP(Pam2)-peptide MALP2 compounds exhibit TLR2 agonist activity when screened using the TLR2 bioassay at a 1 µg/mL concentration.

A TLR2 agonist analog derived peptide library of soluble compounds designed to be more potent TLR2 agonists based on the SAR modifications was developed, synthesized, and screened (Table 4). This set of compounds are all fully synthetic, derived from different origins, and based on SAR low potency of SAA observed in the screening assay may be due to heat degradation because the cells were stimulated with ligand for 24 h at 37° C. versus only 5 hours in the Cheng et al screening assay (Jin, M. S., et al. *Immunity*, 2008. 29(2):182-91). The higher potency of the X-Dhp (Pam2)-peptide MALP2 compound set may indicate that there is improved stability compared to SAA compound.

TABLE 4

TLR2 agonist analog synthetic compound library set

| Compound | Structure | Origin | Molecular Weight (g/mole) |
|---|---|---|---|
| 359 | Ac-PEGO20-Dhc(Pam)$_2$-Gly-Asn-Asn-Asp-Glu-Ser-Asn-Ile-Ser-Phe-Lys-Glu-Lys-NH$_2$ (SEQ ID NO: 10) | Synthetic MALP2 | 2493.4 |
| T-02 | Ac-PEGO-Dhc(Pam)$_2$-Gly-Ser-PEGO-NH$_2$ | Synthetic MALP2 | 1492.9 |
| T-03 | Ac-PEGO-Dhc(Pam)$_2$-Ser-Arg-Phe-Asp-Glu-Asp-Asp-Leu-Glu-NH$_2$ (SEQ ID NO: 5) | CD14 | 2137.2 |
| T-05 | Ac-PEGO-Dhc(Pam)$_2$-Gly-Ser-Gln-Asn-Leu-Ala-Ser-Leu-Glu-Glu-NH$_2$ (SEQ ID NO: 6) | S. aureus | 2059.2 |
| Pam2CSK4 | S-[2,3-bis(palmitoyloxy)-(2RS)-propyl]-[R]-cysteinyl-[S]-seryl-[S]-lysyl-[S]-lysyl-[S]-lysyl-[S]-lysine (SEQ ID NO: 11) | Synthetic | 1271.85 |
| Pam3CSK4 | N-Palmitoyl-S-[2,3-bis(palmitoyloxy)-(2RS)-propyl]-[R]-cysteinyl-[S]-seryl-[S]-lysyl-[S]-lysyl-[S]-lysyl-[S]-lysine (SEQ ID NO: 11) | Synthetic | 1509.6 |
| SAA (recombinant human apo-SAA1) | MRSFFSFLGE AFDGARDMWR AYSDMREANY IGSDKYFHAR GNYDAAKRGP GGVWAAEAIS DRENIQRFFG HGAEDSLADQ AANEWGRSGK DPNHFRPAGL PEKY (SEQ ID NO: 9) | E. coli | 11.7 |

Figure 11:
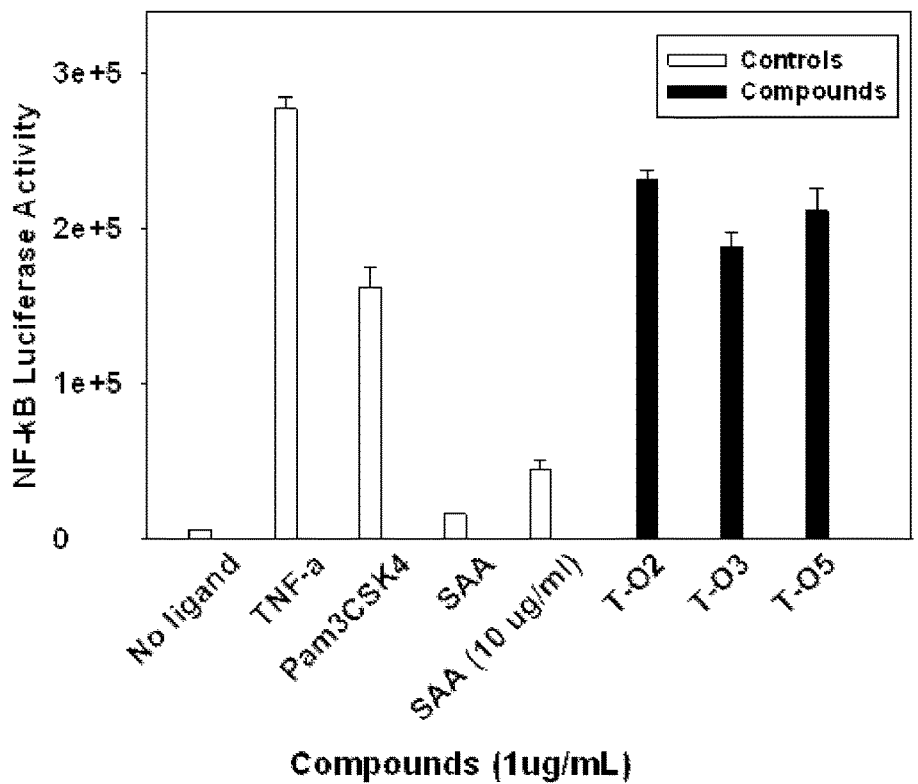
FIG. 11 is a bar graph showing TLR2 activity (luciferase bioluminescence) in HEK293/hTLR2 cells treated with no ligand, TNF-α, Pam3CSK4, serum amyloid A (SAA) (1 µg/mL), SAA (10 µg/ml), or one of three TLR2 agonist analog derived peptide library (T-02, T-03, T-05). n=3 assays with quadruplicate wells, p value<0.001.
Figure 12A:
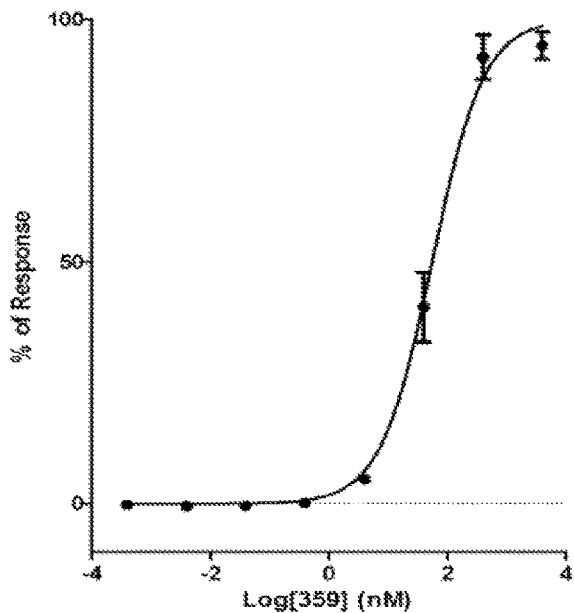
FIGS. 12A-12F are dose-response curves (% response as a function of concentration (Log nm)) generated by measuring the TLR2 agonistic activity of HEK293/hTLR2 cells treated with 359 (FIG. 12A), T-02 (FIG. 12B), T-03 (FIG. 12C), T-05 (FIG. 12D), Pam2CSK4 (FIG. 12E) and Pam3CSK4 (FIG. 12F). Data points represent the mean±SEM, n=6 assays using quadruplicate wells for 359, T-02, T-03, T-05 compounds and n=3 assays using quadruplicate wells for Pam2CSK4 and Pam3CSK4.
Figure 12B:
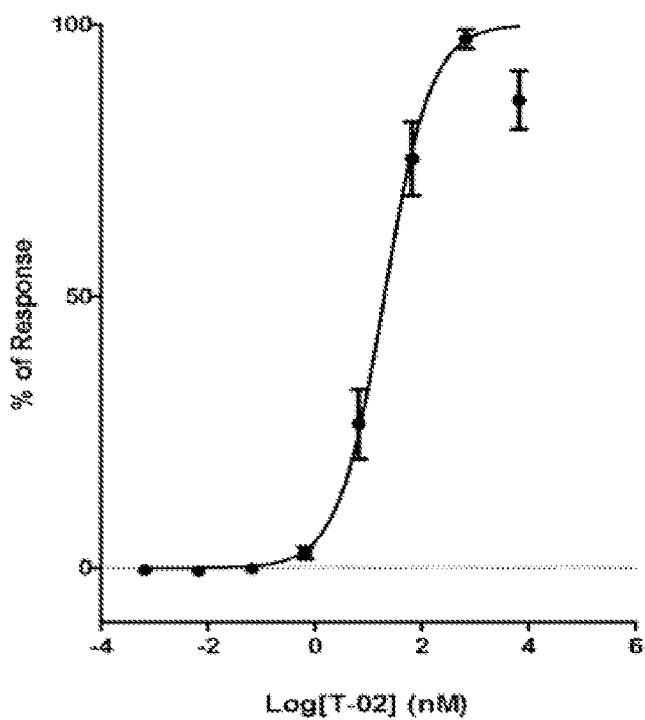
Figure 12C:
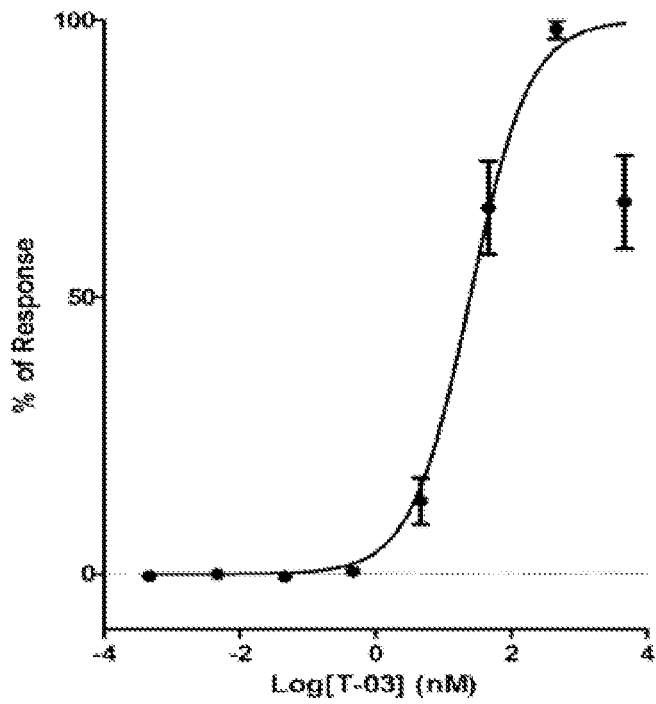
Figure 12D:
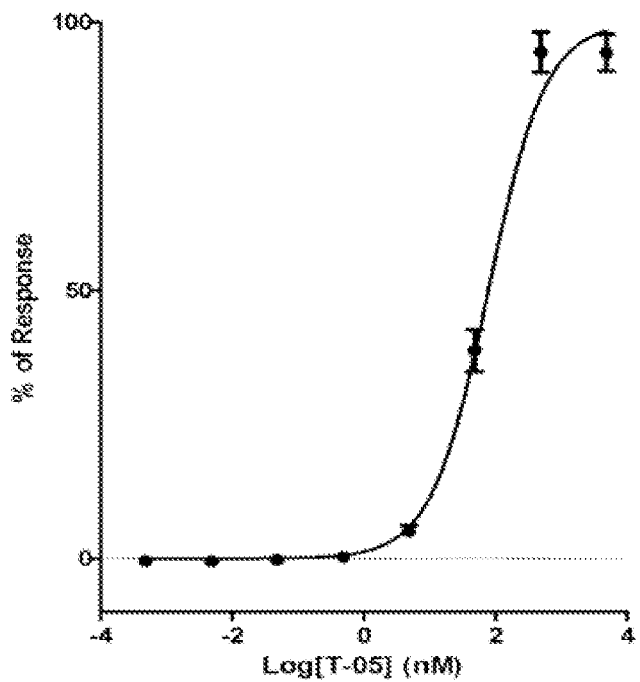
Figure 12E:
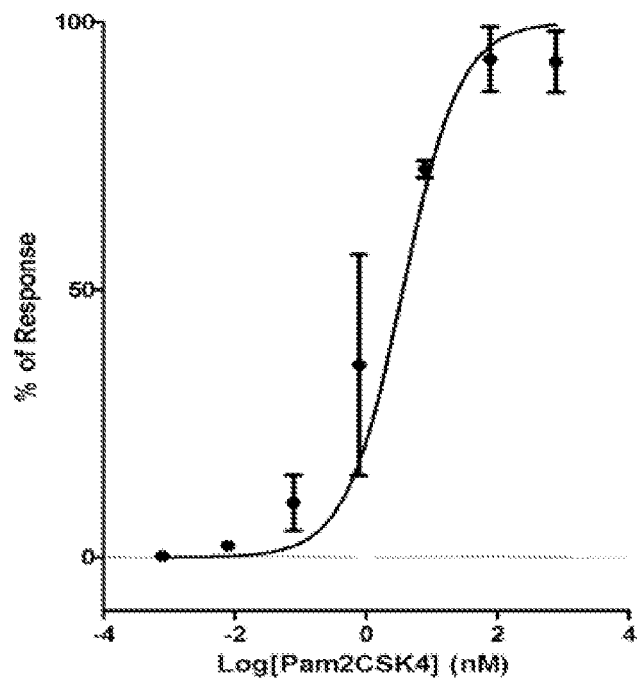
Figure 12F:
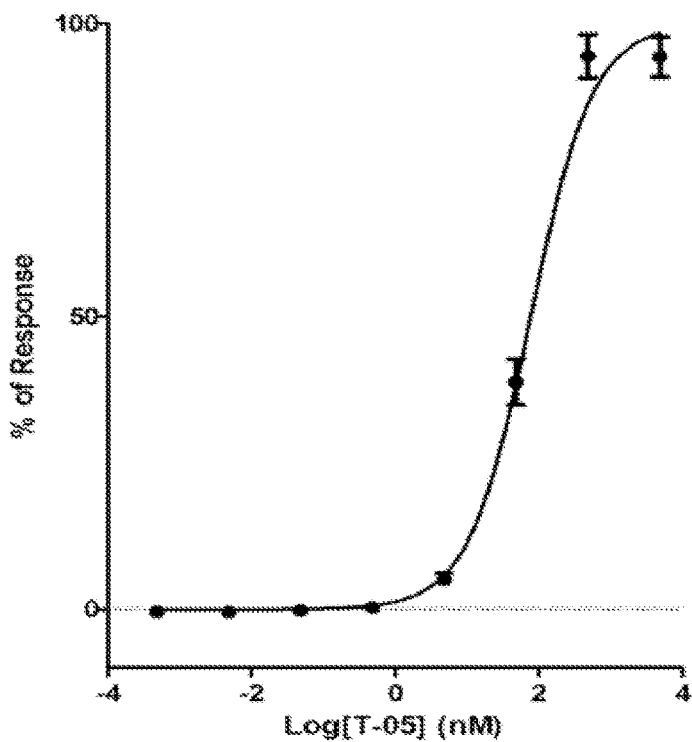

* indicates reference peptide.

modifications they should have more potential to be more acidic, hydrophilic, and more soluble than first library due to the addition of PEGO groups, which are hydrophilic components. T-02 (Ac-PEGO-Dhc (Pam)$_2$-Gly-Ser-PEGO-NH$_2$) was derived from synthetic origin based on the scaffold of MALP2 with manipulation of N terminal PEGO. T-03 (Ac-PEGO-Dhc(Pam)$_2$-Ser-Arg-Phe-Asp-Glu-Asp-Asp-Leu-Glu-NH$_2$, SEQ ID NO:5) was derived from CD14 peptide origin manipulation of N-terminal PEGO. T-05 (Ac-PEGO-Dhc(Pam)$_2$-Gly-Ser-Gln-Asn-Leu-Ala-Ser-Leu-Glu-Glu-NH$_2$, SEQ ID NO:6) was derived from *S. aureus* peptide origin that should be more acidic or at least neutral compared to recently identified potent TLR2 agonist, SAA (serum amyloid A) by Cheng et al. (Jin, M. S., et al. *Immunity*, 2008. 29(2):182-91). The tested SAA was a recombinant human Apo-SAA1 (Peprotech) derived from *E. coli*. SAA is a major acute-phase protein that is considered to be a marker for inflammatory diseases even though its role is still not fully known. As shown in FIG. 11, all three of the compounds exhibited high levels of luciferase activity when screened using the TLR2 functional bioassay (n=4, p<0.001 by t-test). These levels were comparable to the Pam3CSK4 reference control and much more potent than SAA at both 1 µg/mL and 10 µg/mL. However, Cheng et al. did observe that heat-treated SAA (95° C. for 30 min) lost 95% of its activity in a similar type of NF-κB luciferase screening assay, thus indicating that SAA may be easily degraded by heat (Jin, M. S., et al. *Immunity*, 2008. 29(2):182-91). The The potency of the second set of TLR2 agonist analog compounds (T-02, T-03, and T-05) were further characterized along with compound 359 from the first set, and Pam2CSK4, and Pam3CSK4 as reference compounds. The activity of each TLR2 agonist was measured using the in vitro TLR2 functional bioassay over a range of doses from 0.01 ng/mL to 1 µg/mL. FIGS. 12A-12F show the normalized dose-response curves generated by measuring the TLR2 agonistic activity for each compound over the range of concentrations.

$EC_{50}$ values were generated from the dose-response curves. The $EC_{50}$ of a dose response curve represents the concentration of an agonist where 50% of its maximal effect is observed. The $EC_{50}$ value of T-02 was the lowest at 20.09 nM concentration with a 95% confidence interval of 26.55 to 30.05 nM; while 3.66 nM and 22.54 nM are the $EC_{50}$ values for Pam2CSK4 and Pam3CSK4 respectively (Table 5). T-02 is also the smallest structure, with a molecular weight of 1492 g/mol, amongst the novel synthetic TLR2 agonists. Even though it is still in the low nanomolar concentration range, compound T-05 exhibited the highest $EC_{50}$ value, 78.41 nM in our TLR2 functional bioassay which was nearly 4 times higher concentration than T-02. Compound T-05 was not the largest of the peptides but was the only peptide that had a bacterial origin scaffold, while the origin of T-02 is the synthetic form of MALP-2. It is also worth noting that the curves for each ligand tested follow the typical sigmoidal shape that is expected of a receptor binding curve. Except for the curves of the 2 most potent TLR2 ligands, T-02 and T-03, NF-κB luciferase activity decreased at 1 μg/mL, the highest concentration. This decrease in NF-κB luciferase activity may be due to steric hindrance caused by over saturation of the ligand; which is supported by the fact these 2 ligands are nearly 2 to 4 times more potent compare than the other ligands. Based on these results, it was concluded that T-02, T-03, T-05, and 359 are highly potent activators of TLR2 with in vitro $EC_{50}$ concentrations in the low nanomolar range from 20.09 nM to 78.41 nM, indicating that these fully synthetic agonists have high affinity and high efficacy for TLR2.

TABLE 5

EC50 Values calculated from log(agonist) vs. normalized response

| Compound | EC50 (nM) | 95% Confidence Interval (nM) | R Square Value |
|---|---|---|---|
| 359 | 55.64 | 181.60 to 201.10 | 0.9989 |
| T-02 | 20.09 | 26.55 to 30.05 | 0.9997 |
| T-03 | 24.97 | 45.27 to 63.20 | 0.9979 |
| T-05 | 78.41 | 118.80 to 130.40 | 0.9993 |
| Pam2CSK4 | 3.66 | 1.08 to 4.91 | 0.9577 |
| Pam3CSK4 | 22.54 | 17.70 to 102.30 | 0.9363 |

Example 16: Evaluation of In Vivo Cellular Immune Responses

Materials and Methods
Animals

All procedures were in compliance with the Guide for the Care and Use of laboratory Animal Resources (1996), National Research Council, and approved by the Institutional Animal Care and Use Committee, University of South Florida. Immunocompromised mice were housed in a clean facility with special conditions that include HEPA filtered ventilated cage systems, autoclaved bedding, autoclaved housing, autoclaved water, irradiated food and special cage changing procedures. Mice were handled under aseptic conditions including the wearing of gloves, gowns and shoe coverings.

In Vivo Cellular Immune Response Assays

To assess the efficacy of T-02 as an immune adjuvant, mice were immunized i.v. with a mixture of 100 μg optimized $Trp1_{455/9M}$ peptide (Guevara-Patino, J. A., et al. *J Clin Invest*, 2006. 116(5):1382-90), 50 μg anti-CD40 mAb (Clone; FGk-45.5), and 50 μg TLR-2 peptide (T-02, Pam2CSK4, or Pam3CSK4). When the $Trp1_{455/9M}$ peptide was tested using the TLR2 functional bioassay, it was determined that it is not a TLR2 agonist. The response of tetramer+ CD8 T cells in the blood was measured on day 7, 21, and 34 by tetramer staining. For tetramer staining, peripheral blood was taken from the submandibular vein and treated briefly with ammonium chloride buffer to lyse red blood cells. Blood cells were stained with FITC-conjugated anti-MHC class II, PerCP Cy5.5-conjugated CD8a (both from eBioscience, San Diego, Calif.), and phycoerythrin-conjugated $Trp1_{455/9M}/H-2D^b$ tetramers (provided by the NIH tetramer Facility, Emory University, Atlanta Ga.) for 40 min in ice. Fluorescence was evaluated using a FACSCalibur™ flow cytometer (BD Biosciences) and analyzed using FlowJo software.

Results

Using TLR agonists as vaccine adjuvants is a very promising application that has been highly explored to prevent and treat cancer as well as infectious diseases. The use of TLR agonists as immune adjuvants in peptide vaccination together with anti-CD40 monoclonal antibodies can increase the magnitude and duration of T-cell responses resulting from various types of immunizations including peptide vaccines (Cho, H. I., et al. *Cancer Res*, 2009. 69(23):9012-9; Celis, E., et al. *Cancer Res*, 2007. 67(17):7945-7).

Accordingly, the activity of T-02 as an immune adjuvant was selected to be evaluated in vivo and compared to the well-characterized commercially available synthetic TLR-2 agonists, Pam2CSK4 and Pam3CSK4. For these experiments, a peptide was selected from mouse tyrosinase-related protein-1 ($Trp1_{455/9M}$) that serves as an epitope for CD8 T cells in the context of H-$2D^b$ (Guevara-Patino, J. A., et al. *J Clin Invest*, 2006. 116(5):1382-90). The $Trp1_{455/9M}$-specific CD8 T cell responses were monitored in the blood on days 7, 21, 34 post-administration of immune adjuvants and analyzed by flow cytometry. No signs or symptoms of stress or toxicity were observed in the mice over the course of the experiment. Kimbrell et al. reported that LPs are extremely potent TLR2 agonists in vivo with no apparent toxicity in animal models (Kimbrell, M. R., et al. *Immunol Lett*, 2008. 118(2):132-41).

Figure 13A:
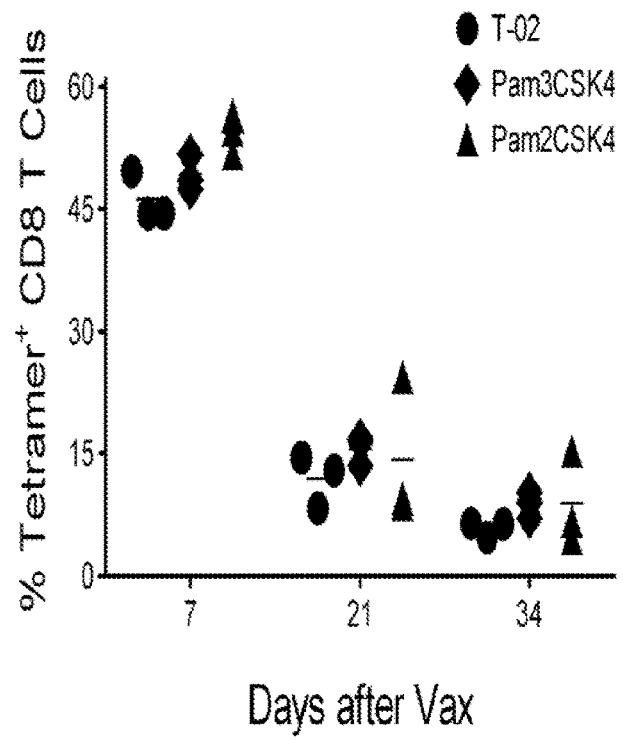
FIG. 13A is a plot showing antigen-specific CD8 T cells (% cells with Trp1455/9M/H-2 Db tetramer staining) in peripheral blood as a function of time (7, 21 and 34 days) in B6 mice (n=3) immunized i.v. with a mixture of Trp1455/9M peptide, anti-CD40 mAb plus one of the following TLR2 agonists: T-02 (●), Pam2CSK4 (♦), or Pam3CSK4 (▲).
Figure 13B:
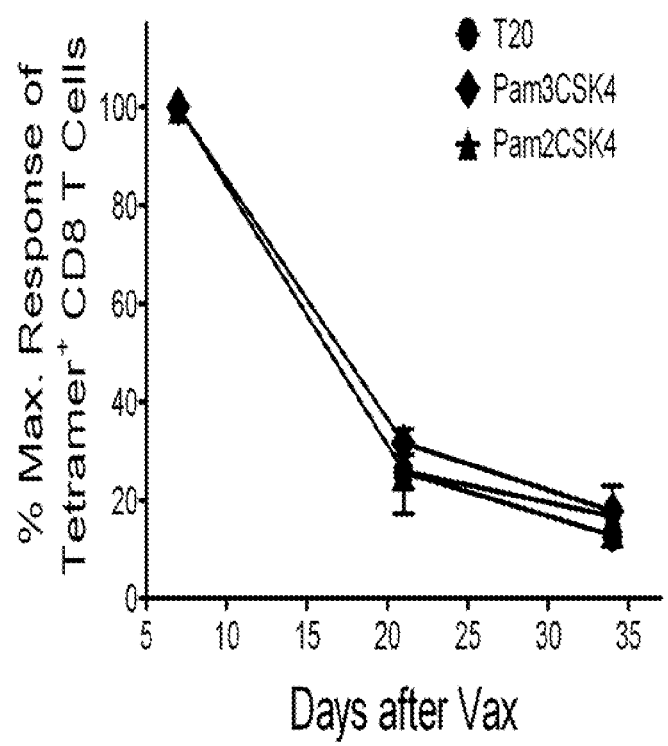
FIG. 13B is a graph showing mean maximum response of antigen-specific CD8 T cells in peripheral blood for up to 34 days post-immunization (n=3).

High fluorescence was observed on day 7 for the stained tetramer positive CD8 T cells for T-02, Pam2CSK4, and Pam3CSK4. The 100% response rate of the tetramer positive CD8 T cells using T-02 as immune adjuvant was observed on day 7 decreased to levels comparable to using either Pam2CSK4 or Pam3CSK4 on day 21 (FIG. 13). These results indicate that the TLR-2 agonist T-02 exhibited similar in vivo activity comparable to the TLR-2 agonists, Pam2CSK4 and Pam3CSK4, for the generation and persistence of antigen-specific CD8 T cells. Therefore, T-02 ligand is a highly potent TLR2 agonist both in vitro and in vivo that is comparable to the reference TLR2 ligands Pam2CSK4 and Pam3CSK4.

Example 17: Binding Assays

Materials and Methods
Time Resolved Fluorescence Competitive and Saturation Binding Assays TRF binding assays were performed as previously described (see Xu, L., et al. *Mol Cancer Ther.* 2009 8(8): 2356-65).

Results

Figure 15A:
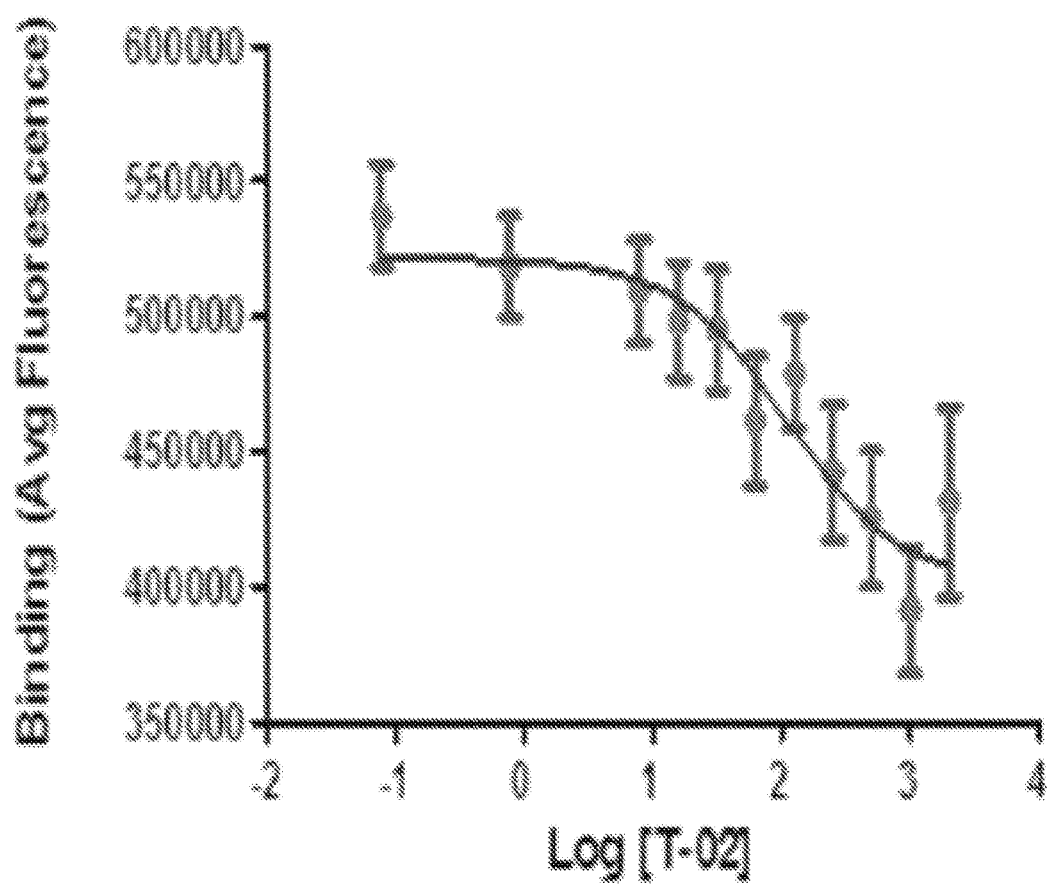
FIGS. 15A, 15B, and 15C show graphs of binding fluorescence and tissue retention. A) Competitive binding assay of T-02 bound with 25 nM $K_i$, B) A version of the T-02 conjugated to the LiCor IRDye800CW bound with a comparable 10 nM $K_i$ affinity. C) The LiCor IRDye800CW/T-02 conjugate was injected into an animal bearing a TLR2 expressing SU.86.86 pancreatic cancer cell xenograft and was shown to be retained in the tumor at 24 h post injection while the agent had cleared from the animal except for the kidneys.
Figure 15B:
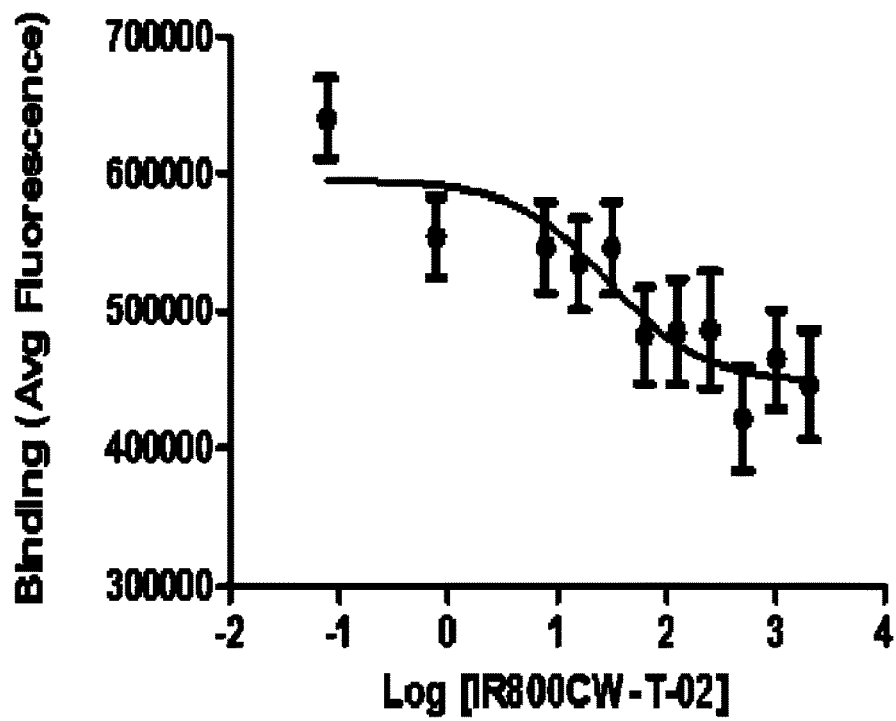
Figure 15C:
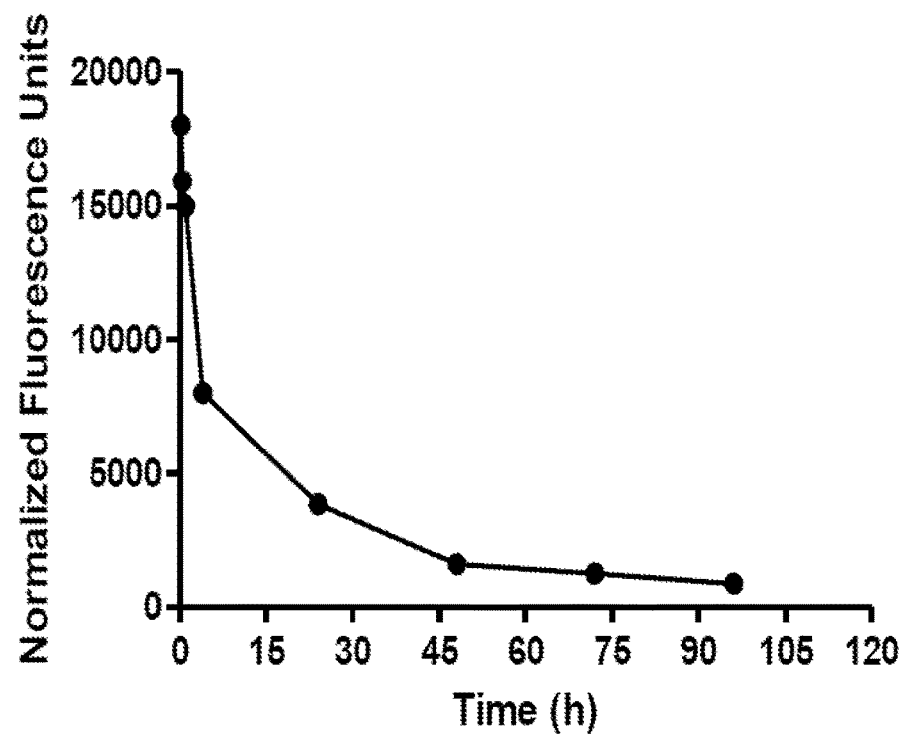

Direct binding assays for TLR2 have not typically been used to determine biological activity, while SAR has been mostly determined by various reporter gene or functional cell-based assays (Kanzler, H., et al., et al. *Nat Med*, 2007. 13(5):552-9). A time-resolved fluorescence competitive and saturation binding assays was performed for the T-02 ligand and T-02 ligand conjugates. By competitive binding assay, T-02 bound with 25 nM Ki (FIG. 15A). A version of the T-02 conjugated to the LiCor IRDye800CW (FIG. 14) bound with a comparable 10 nM Ki affinity (FIG. 15B). A version conjugated with a Eu-DTPA chelate bound with 30 nM Kd. The LiCor IRDye800CW/T-02 conjugate (FIG. 14) was injected into an animal bearing a TLR2 expressing SU.86.86 pancreatic cancer cell xenograft and was shown to be retained in the tumor at 24 h post injection while the agent had cleared from the animal except for the kidneys (FIG. 15C). The agent cleared from the kidney within days of the injection but was retained longer in the tumor. A time course demonstrated that a low 10 nmol/Kg dosage was retained in the SU.86.86 tumor for over 96 h (FIG. 15). The agent was also taken into and retained in orthotopic pancreatic tumor xenografts.

Example 18: Minimal Peptide TLR2 Ligands

The discovery of ligands and small-molecular-mass synthetic compounds that specifically activate Toll-like receptor 2 (TLR2) has raised interest in this cell-surface receptor as a potential target for the development of new therapies, including the treatment of cancer.1 TLR2 has a role in activation and regulation of the innate immune system and targeted stimulation of this receptor has been used to augment cancer immunotherapy.[1a, 2] Although TLR2 is predominantly expressed in tissues involved in immune function, the expression profile varies among tissues and cell types.[3] TLR2 is a type I transmembrane glycoprotein characterized by an external antigen recognition domain comprised of a highly conserved leucine-rich repeat motif, a transmembrane domain, and a cytoplasmic Toll/interleukin-1 (TIR) receptor homology signaling domain. Intracellular signaling is activated by agonist binding and is facilitated by the formation of the cytoplasmic TIR domain through heterodimerization with either TLR1 or TLR6.[4, 5] TLR2 is a pattern recognition receptor with the ability to recognize pathogen-associated molecular patterns (PAMPs). [6] Stimulation by PAMPs initiates signaling cascades that activate NF-κB transcription factors inducing the secretion of pro-inflammatory cytokines and effector cytokines directing the immune response.[6c]

The potential use of synthetic TLR2 agonists for the enhancement of cancer immunotherapy is an active area of research. There are four mechanisms by which TLR2 stimulation may produce significant antitumor activity: enhancement of the innate immunity, enhancement of T-cell immunity, enhancement of cytotoxic antibody function, and induction of apoptosis in TLR2-positive tumors.[1a] Examples include, the TLR2 induction of tumor necrosis factor-α (TNF-α), increasing the production of nitric oxide synthase (iNOS) and thus inducing apoptosis of chemotherapy-resistant tumor cells;[7] reduction of bladder tumor growth by TLR2 agonist, SMP-105;[8] and TLR2 targeted induction of the immune system by the lipid-A derivative drug, OM-174, as a cancer vaccine adjuvant during immunotherapy.[9] We have developed the TriVax vaccine using TLR agonists as immune adjuvants in combination with peptide vaccination and anti-CD40 monoclonal antibodies, which can increase the magnitude and duration of vaccine-induced T-cell responses, eliciting potent protective antitumor immunity as well as remarkable therapeutic effects against melanoma.[10]

In an effort to improve the less than 6% 5 year survival rate for pancreatic cancer, TLR2 ligands are being studied for use in targeted pancreatic cancer imaging and treatment. [11] Improved survival rates are associated with the surgical resection of the primary tumor if the tumor tissue is completely removed at the margins.[12] However, it is a high risk procedure with a low success rate due to difficulty in clearly identifying tumor tissue from normal tissue, resulting in positive resection margins (R1).[13] The development of new intraoperative surgical methods employing fluorescence guided tumor detection could lead to increased negative resection margins ($R_0$) resulting in improved survival rates. Recent clinical studies involving image-guided surgeries have demonstrated the potential of this approach.[14, 15] We have previously reported TLR2 as a bona fide cell surface marker for pancreatic cancer that is highly expressed in 70% of pancreatic tumors but is not highly expressed in surrounding normal pancreas tissue.[16] Fluorescence imaging probes developed using TLR2 specific ligands could be applied to the intraoperative detection of pancreatic tumor margins.

A variety of microbial component derived lipopeptides (LPs) are recognized as TLR2 ligands. For example, mycoplasma produce diacylated macrophage-activating lipopeptides 2-kDa (MALP-2), Cys(S-[2,3-bisacyloxy-(R)-propyl])-Gly-Asn-Asn-Asp-Glu-Ser-Asn-Ile-Ser-Phe-Lys-Glu-Lys (SEQ ID NO:10), bind to the TLR2/TLR6 heterodimer. [17] The structure-activity relationships (SAR) of TLR2 binding and stimulation of the immune system for many synthetic LPs are well documented in the literature. Both the well-characterized synthetic di- and tri-acylated LP ligands, $Pam_2CSK_4$ and $Pam_3CSK_4$, bind to internal protein pockets through hydrophilic interactions to selectively induce signaling via the TLR2/TLR6 and TLR2/TLR1 heterodimers, respectively.[5, 17c, 18] In addition to LPs, the serum amyloid A protein (SAA) was recently identified as a potent TLR2 agonist by Cheng et al., and is a major acute-phase protein that is considered to be a marker for inflammatory diseases.[19]

TLR2 specific agonist ligands developed herein have potential for use in both the development of targeted agents for the imaging and treatment of pancreatic cancer, and as an adjuvant for cancer immunotherapy. In an effort to identify novel TLR2 ligands that are highly potent TLR2 agonists for use in immunotherapy, or ligands with high binding affinity for TLR2 with potential for attachment of imaging contrast and therapeutic agents, we have iteratively synthesized two sets of rationally designed synthetic compounds and investigated their SAR by functional bioassays, in cyto binding assays, in vivo immune system stimulation and molecular imaging studies demonstrating tumor specificity. Compound 10 had potent bioactivity (20 nM $EC_{50}$), high affinity binding (24 nM $K_i$) and effective immune system stimulation. After conjugation of a near-infrared fluorescent dye to 10 generating 13, high bioactivity (34 nM $EC_{50}$) and binding affinity (11 nM $K_i$) were retained, and tumor specificity was observed in vivo by fluorescence imaging of mice bearing xenograft tumors. In addition, 10 has a greatly simplified synthesis strategy with improved solubility and a built-in attachment point for imaging contrast and/or a therapeutic moiety.

Figure 25:
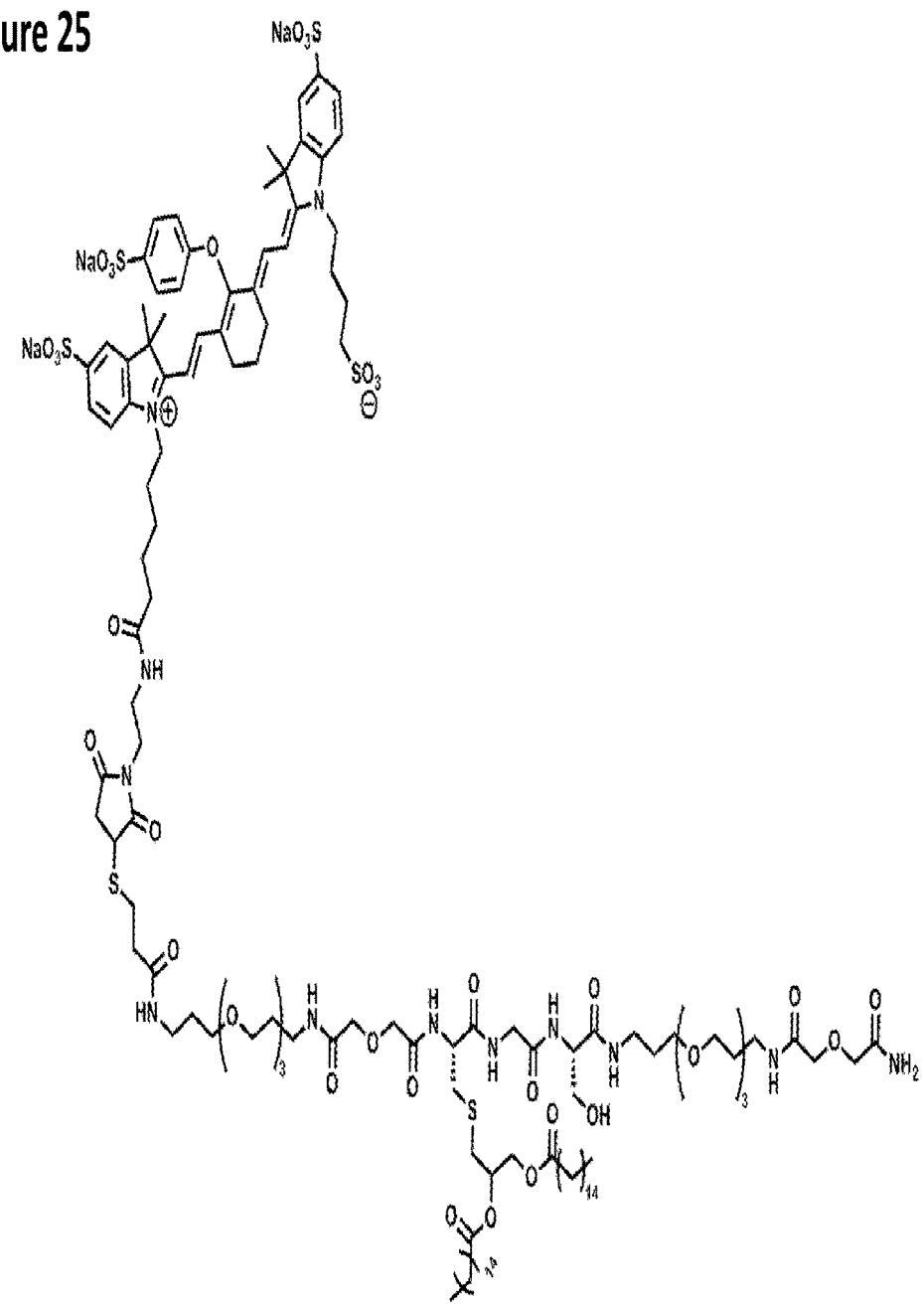
FIG. 25 shows the structure of compound 13, IRDye800CW-Mpr-PEGO-Cys(S-[2,3-bis(palmitoyl)oxy-(R)-propyl]-Gly-DSer-PEGO-NH$_2$ (T-02).

Toll-like receptor 2 (TLR2) is a target for immune system stimulation during cancer immunotherapy and a cell-surface marker for pancreatic cancer. To develop targeted agents for cancer imaging and therapy, we designed, synthesized and characterized thirteen novel, fully synthetic high affinity TLR2 agonists, based on known structure activity relationships. Analog 10 had the highest agonist activity (NF-κB functional assay, $EC_{50}$=20 nM) and binding affinity (competitive binding assay, $K_i$=25 nM). In vivo mouse studies determined that compound 10 stimulated the immune system by generation and persistence of antigen-specific CD8 T cells indicating its potential use in cancer immunotherapy. After conjugation of a near-infrared dye to 10, agonist activity ($EC_{50}$=34 nM) and binding affinity (Ki=11 nM) were retained in 13. Compound 13 has the lowest mass (2729 MW), and highest binding affinity (11 nM $K_i$) and agonist activity (34 nM $EC_{50}$) (FIG. 16A) retained after conjugation of the IR800CW NIR dye (Compound 13: IRDye800CW-MPA-PEGO-dihydroxycysteine(palmitoyl)-2-Gly-Ser-Ac-PEGO-NH$_2$; FIG. 25). Fluorescence signal was present in TLR2 expressing pancreatic tumor xenografts 24 h post-injection of 13; while an excess of unlabeled ligand blocked 13 from binding to the tumor resulting in significantly decreased signal (p<0.001) demonstrating in vivo selectivity.

Improved survival rates for pancreatic cancer are associated with the complete surgical resection of tumor resulting in a tumor-free margin ($R_0$). New methods employing intraoperative fluorescence (FL) guided tumor detection could lead to increased $R_0$ margins and improved survival. We have reported Toll-like receptor 2 (TLR2) as a bona fide cell-surface marker for pancreatic adenocarcinoma. We then developed a high-affinity TLR2 binding ligand conjugated to a near-infrared (NIR) fluorescent dye, IR800CW, as a targeted molecular imaging probe for the intraoperative detection of surgical margins. To evaluate the in vivo pharmacokinetics and biodistribution of compound 13, FL imaging was performed on multiple optical imaging systems (PerkinElmer IVIS 200 and FMT2500XL, and ART Optix MX3) using TLR2 expressing pancreatic tumor xenograft mouse models (subcutaneous and orthotopic). Tumor specificity was observed, in which FL signal was retained in TLR2 expressing tumor xenografts up to 96 h post-injection while blocking with an excess of unlabeled competing ligand significantly decreased FL signal in the tumor at 24 h (p<0.001) (Data not shown). To investigate the possibility of achieving $R_0$ margins and improved survival rates using compound 13, in vivo FL guided intraoperative surgical removal of orthotopic pancreatic tumors 24 h post-injection was performed using a Diagnostic Instruments adapted LightTools system outfitted with an 800 nm filter set, cooled CCD camera and SPOT Advanced software (Data not shown); and compared to mice that underwent surgical resection of tumors using normal light. We have previously demonstrated the feasibility of the intraoperative detection of tumors using a different well-characterized Cy5-labeled probe (Dmt-Tic-Cy5) that we also developed. The resected tumors from both groups were then FL imaged ex vivo. Prior to surgery, the orthotopic pancreatic tumor volumes were monitored weekly and measured in vivo by 3D ultrasound imaging. Mice underwent in vivo FL imaging up to 72 h post-surgery to confirm complete resection of the tumors. The excised tumors and remaining normal pancreas underwent H&E staining, IHC for TLR2 expression and pathological evaluation of the margins. In vivo tumor selectivity and intraoperative detection of pancreatic cancer were demonstrated. This method will improve pancreatic cancer survival by increasing the percentage of $R_0$ margins.

Results

TLR2 Ligand Library Design and Synthesis.

Thirteen novel fully synthetic compounds were designed and synthesized to discover novel TLR2 specific ligands with the desired properties of high specificity, high agonist activity, high binding affinity, solubility and built-in attachment points for conjugation of fluorescent dye and chelates. Initially, seven compounds (1-7) based on the structure of the bispalmitoylated MALP-2, Cys(S-[2,3-bis(palmitoyl)oxy-(R)-propyl]-Gly-Asn-Asn-Asp-Glu-Ser-Asn-Ile-Ser-Phe-Lys-Glu-Lys (SEQ ID NO:10), were synthesized.17a Each compound in the set was comprised of the same scaffold, X-Cys(S-[2,3-bis(palmitoyl)oxy-(R)-propyl]-Gly-Asn-Asn-Asp-Glu-Ser-Asn-Ile-Ser-Phe-Lys-Glu-Lys-$NH_2$ (SEQ ID NO:10), or X-MALP-2 where the X-group represents an N-terminal modification (Table 6, FIG. 23).

After screening compounds 1-7 for bioactivity, a second set of three compound analogs (8-10) was designed based on SAR knowledge gained from the first set. The scaffold, Ac-PEGO-Cys-[2,3-bis(palmitoyl)oxy-(R)-propyl])-Y, was derived using compound 3's N-terminal modification of the MALP-2 LP that included an acetylated 20 atom ethylene glycol oligomer (PEGO) plus Y modifications at the C-terminus (Table 6).

TABLE 6

Synthesized Compounds.

| # | Compounds (X, Y or Z Modifications) | MW |
|---|---|---|
| | X-Cys(S-[2,3-bis(palmitoyl)oxy-(R)-propyl])-Gly-Asn-Asp-Glu-Ser-Asn-Ile-Ser-Phe-Lys-Glu-Lys-$NH_2$ (SEQ ID NO: 10) | |
| 1 | Palmitoyl | 2371.4 |
| 2 | Fluorescein- | 2491.3 |
| 3 | Ac-PEGO[a] | 2493.4 |
| 4 | Ac-Aha[b]- | 2288.3 |
| 5 | Adapalenoyl- | 2526.4 |
| 6 | Ac-Aun[c]- | 2358.4 |
| 7 | Tretinoyl- | 2414.4 |
| | Ac-PEGO-Cys(S-[2,3-bis(palmitoyl)oxy-(R)-propyl])-Y | |
| 8[d] | Ser-Arg-Phe-Asp-Glu-Asp-Asp-Leu-Glu-$NH_2$ (SEQ ID NO: 5) | 2137.2 |
| 9 | Gly-Ser-Gln-Asn-Leu-Ala-Ser-Leu-Glu-Glu-$NH_2$ (SEQ ID NO: 6) | 2059.2 |
| 10 | Gly-DSer-PEGO-$NH_2$ | 1492.9 |
| | Z-PEGO-Cys(S[2,3-bis(palmitoyl)oxy-(R)-propyl])-Gly-DSer-PEGO-$NH_2$ | |
| 11 | Eu-DTPA[e]- | 1975.4 |
| 12 | Mpr[f]- | 1538.9 |
| 13 | IRDye800CW-Mpr- | 2728.8 |

Figure 23:
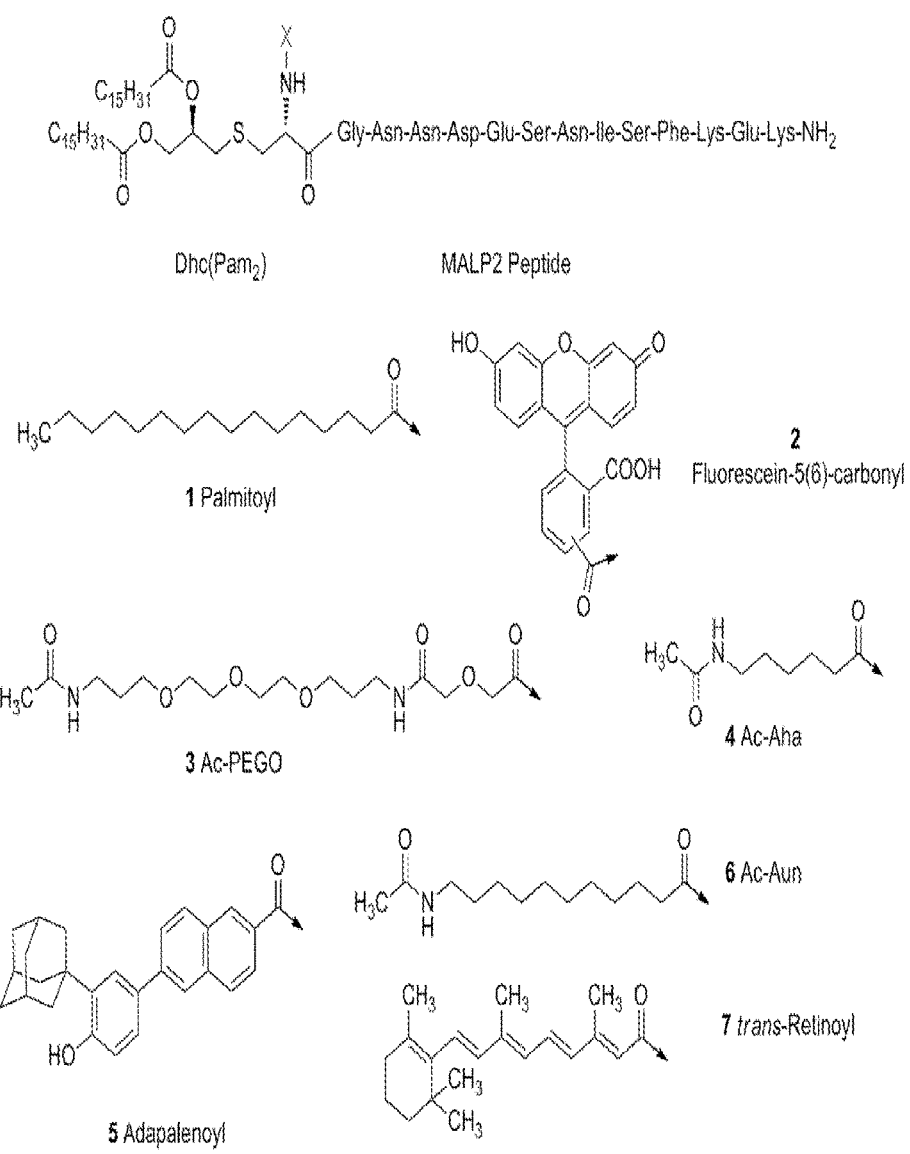
FIG. 23 shows structures for the X-MALP-2 peptide derived compounds 1-7.

[a]PEGO denotes 20 atom ethylene glycol oligomer (the full structure is depicted in FIG. 23);
[b]Aha denotes 6-aminohexanoyl residue;
[c]Aun denotes 11-aminoundecanoyl residue;
[d]all amino-acid residues are D-configuration;
[e]Eu-DTPA denotes Europium chelated in diethylenetriaminepentaacetic acid;
[f]Mpr denotes 3-mercaptopropionyl residue.

Compound 8's Y-group modification was derived from a CD14 peptide known to induce the physical proximity of CD14, TLR2 and TLR1.[20] Compound 9's Y-group modification was derived from a S. aureus peptide that should be more acidic or at least neutral compared to the recently identified potent TLR2 agonist, serum amyloid A (SAA) by Cheng et al. [19a, 21] To test the importance of the peptide component of MALP-2 in terms of potency, compound 10's Y-group modification was derived from compound 3's structure with the peptide component reduced to a short Gly-DSer linker with a PEGO-$NH_2$ at the C-terminus to enhance solubility.

Figure 24:
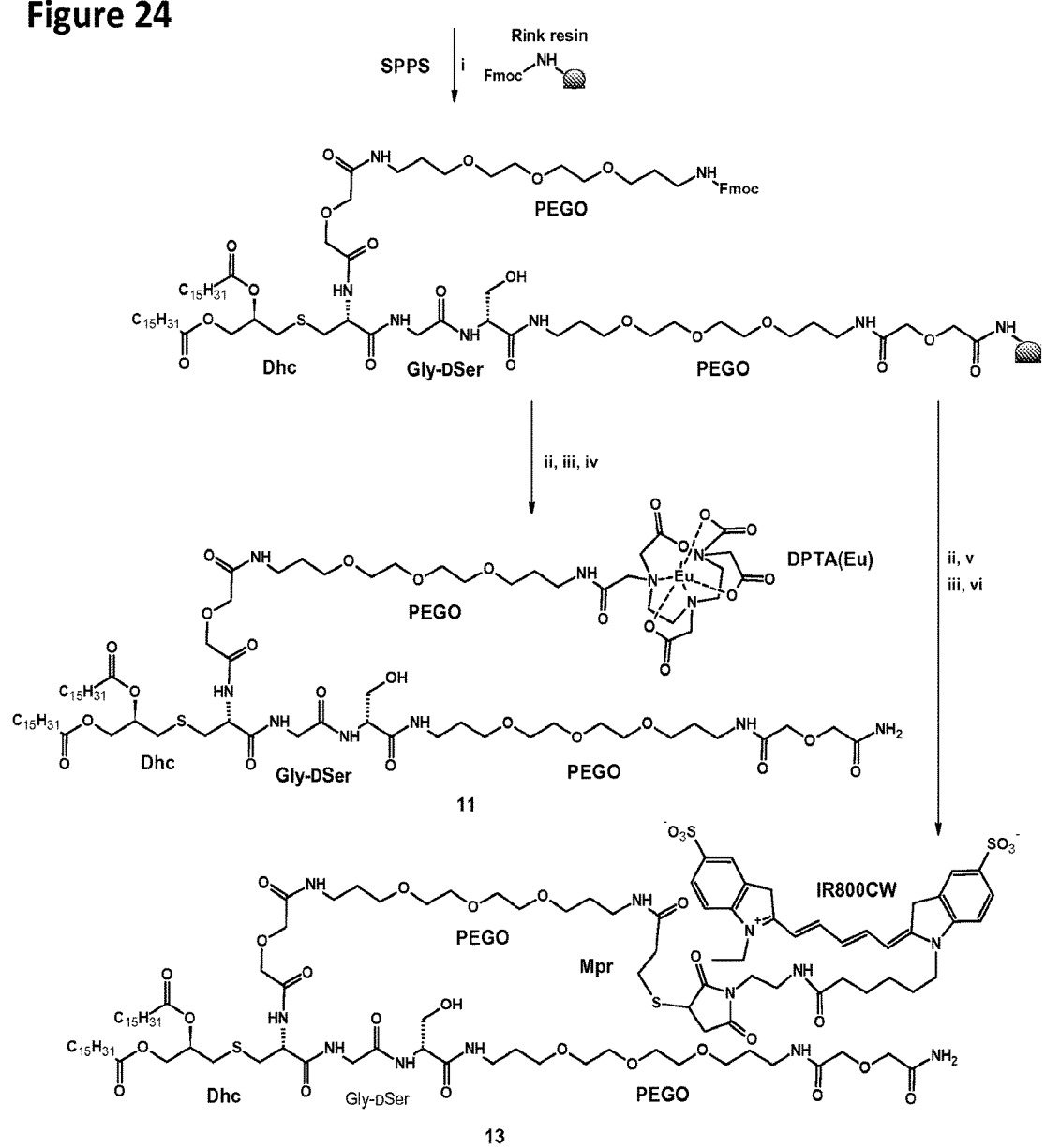
FIG. 24 shows Scheme 1, the synthetic route for Eu-DTPA Ligand 11 and IRDye800CW Ligand 13. i Fmoc/tBu synthesis continued as follows: a) Fmoc-aa-OH (3 eq), HOBt (3 eq), DIEA (6 eq), and HBTU (3 eq) in DMF for amino acid couplings; b) Piperidine/DMF (1:4) for Fmoc deprotection; ii The DTPA was attached as follows: a) DTPA anhydride (3 eq) and HOBt (3 eq) were dissolved in dry DMSO (0.5M), heated to 60° C. for 3 minutes then stirred at room temperature for 30 min, b) preformed DTPA-OBt diester mixture reacts with the resin overnight; iii TFA-scavengers cocktail (90% trifluoroacetic acid, 5% water, 5% triisopropylsilane) for 2 hrs; iv Eu(III)Cl3 (3.0 eq.) in 0.1 ammonium acetate buffer pH 8.0 overnight; vi. IRDye800CW maleimide (1 eq) in DMF.

Since compound 10 was determined to have the most potent TLR2 bioactivity, three final compounds were designed and synthesized to incorporate at the N-terminus, in lieu of the acetyl group, a europium diethylenetriaminepentaacetic acid (Eu-DTPA) chelate (compound 11), 3-mercaptopropionyl residue (Mpr) for attachment to thiol groups (compound 12), and the near-infrared dye IRDye800CW (LI-COR, Lincoln, Nebr., USA) functionalized with Mpr for attachment (compound 13) (Scheme 1 (FIG. 24), Table 6). Compound 11 was used to determine TLR2 binding affinity via in vitro time-resolved fluorescence (TRF) binding assays. Compound 13 was used for in vivo fluorescence imaging to determine TLR2 specificity and binding.

In Cyto Functional Bioassay.

We developed a functional bioactivity assay to specifically detect intracellular signaling induced by agonist stimulation of the human TLR2 receptor at the cell-surface. This assay underwent optimization prior to starting our peptide screenings. Optimal NF-κB induced expression of luciferase led to observed luminescence 48 h post transient transfection and 24 h post ligand stimulation. Luminescence intensity was significantly greater (50-fold, n=6, p<0.001) in Pam$_3$CSK$_4$ ligand stimulated HEK-293/hTLR2 cells relative to cells incubated with no ligand. The ligand-stimulated parental HEK-293 cells had no measurable luminescence. Hence, the measured luminescence is specifically induced by signaling of TLR2 agonists via the NF-κB pathway.

Figure 16A:
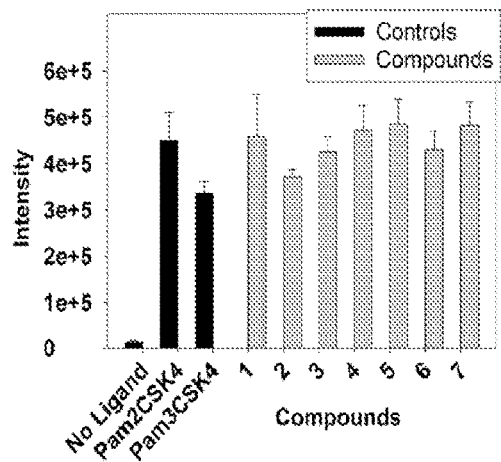
FIGS. 16A-16D show screening of A) X-Cys(S-[2,3-bis (palmitoyl)oxy-(R)-propyl])-MALP-2 derived peptide library (compounds 1-7) and B) compound analogs (8-10) with an acetylated-PEGOX-Cys(S-[2,3-bis(palmitoyl)oxy-(R)-propyl])-Y for TLR2 agonist activity determined using the functional bioassay. All compounds exhibit high luminescence intensities similar to the TLR2 agonist controls, Pam2CSK4 and Pam3CSK4, using the HEK-293/hTLR2 cells (n=3 assays with quadruplicate wells, p value<0.0003). Dose-response curves generated by measuring the TLR2 agonistic activity for C) compound 10 and D) compound 13. Performed by serially adding (0.001 ng/mL to 10 µg/mL) compound to HEK-293/hTLR2 expressing cells (n>3 assays with quadruplicate wells, R2>0.98).

We initially screened the first set of seven MALP-2 derived compounds (1-7) with N-terminal modifications (Table 6) to determine TLR2 agonist activity. All seven of the compounds exhibited comparable levels of NF-κB induced luminescence relative to the reference TLR2 agonist ligand controls (FIG. 16A). Based on these results, all seven compounds exhibit potent TLR2 agonist activity.

Figure 16B:
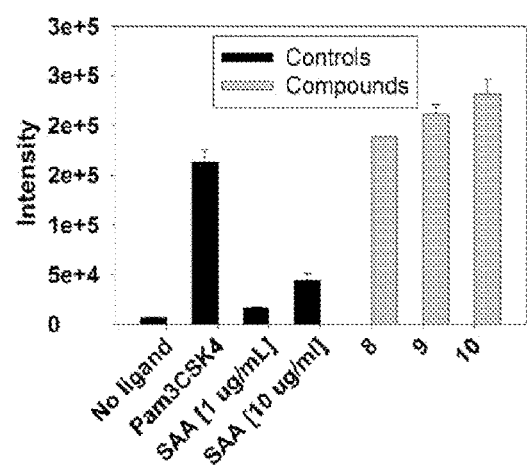

A second set of compound analogs (8-10) that retained the N-terminal modification of compound 3, acetylated PEGO, with different C-terminal variations were screened for TLR2 agonist activity (Table 6). All three of the compounds exhibited significant luminescence intensity relative to the no-ligand control, comparable to the Pam$_3$CSK$_4$ positive control and significantly more potent than SAA at both 1 µg/mL and 10 µg/mL (n=4, p<0.001) (FIG. 16B). The fold of enhancement for 8, 9, and 10 vs SAA at 1 µg/mL was 11, 13 and 14, respectively. The fold of enhancement for 8, 9, and 10 at 1 µg/mL vs SAA at 10 µg/mL was 4.2, 4.8 and 5.2, respectively.

Figure 16C:
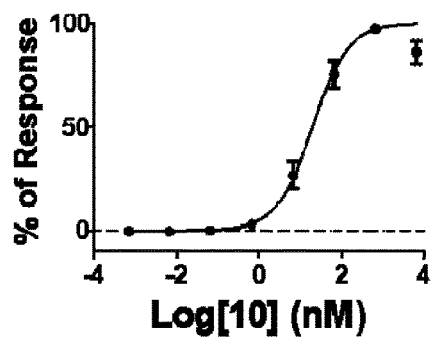
Figure 16D:
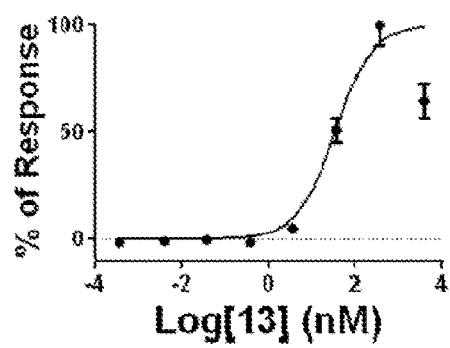
Figure 20A:
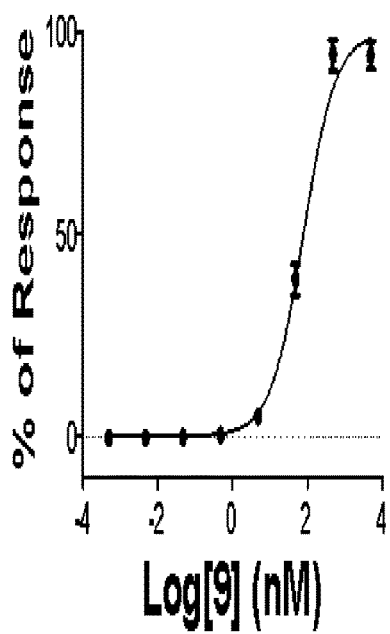
FIGS. 20A-20G show dose-response curves generated by measuring the TLR2 agonistic activity of the following compounds: A) 9, B) 8, C) 3, D) 11, E) 12 and TLR2 reference controls F) Pam$_2$CSK$_4$ and G) Pam$_3$CSK$_4$. The TLR2 functional bioassay was performed by serially adding (0.001 ng/mL to 10 μg/mL) compound to HEK-293/hTLR2 expressing cells (n≥3 assays with quadruplicate well s). The EC$_{50}$ values are reported in Table 7.
Figure 20B:
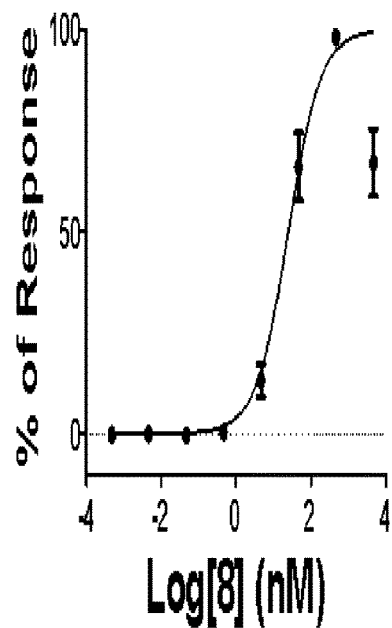
Figure 20C:
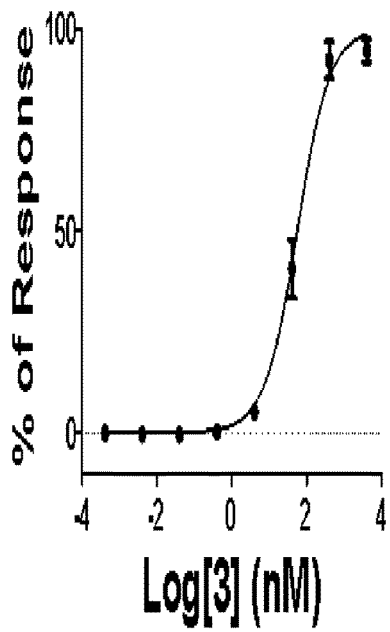
Figure 20D:
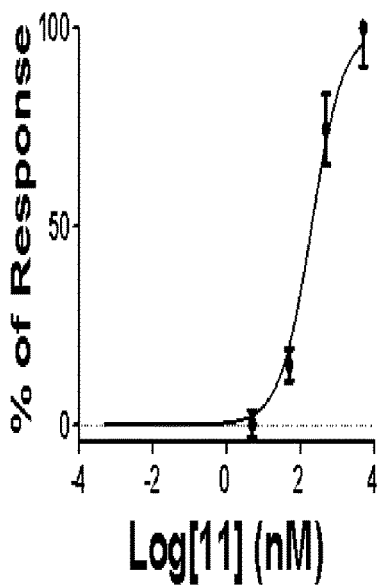
Figure 20E:
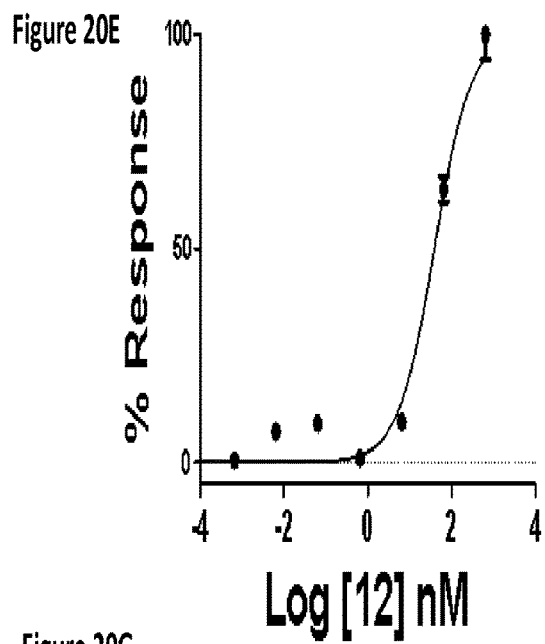
Figure 20F:
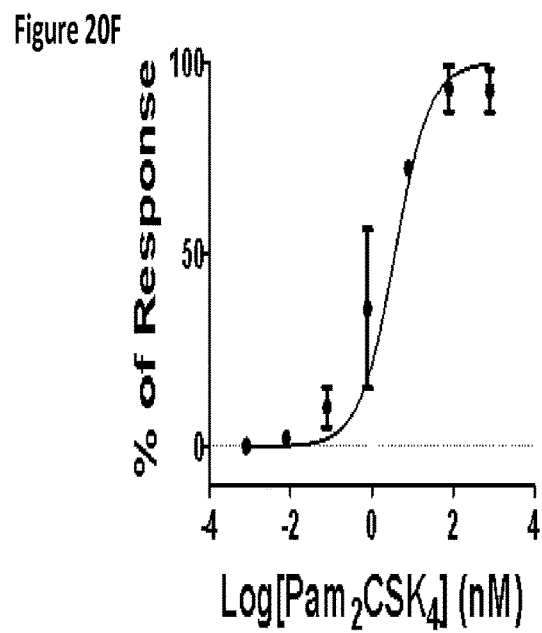
Figure 20G:
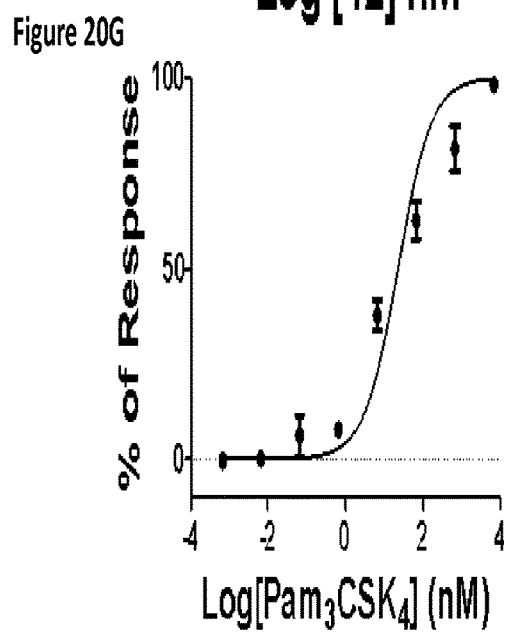

The agonist potency of compounds 3, 8-13, Pam$_2$CSK$_4$ and Pam$_3$CSK$_4$ were further characterized over a range of concentrations (0.001 ng/mL to 10 µg/mL) to determine EC$_{50}$ values. The resulting normalized dose-response curves generated by measuring the TLR2 agonistic activity for each compound and EC$_{50}$ values are reported in Table 7 (n=6 assays for test compounds and n=3 assays for control compounds, R$^2$ values>0.94). Test compounds (3, 8-10) were potent TLR2 agonists with low nanomolar EC$_{50}$ values ranging from 20 to 78 nM. Compound 10 had the lowest EC$_{50}$ value (20 nM) (FIG. 16C), which is comparable to the EC$_{50}$ values for Pam$_2$CSK$_4$ (3.7 nM) and Pam$_3$CSK$_4$ (23 nM) positive controls (FIGS. 20F and 20G). Compounds 11, 12, and 13 based on the structure of 10 with N-terminal attachments were determined to retain nanomolar TLR2 agonist activity 204, 39 and 34 nM respectively (Table 7, FIG. 16D, FIGS. 20D and 20E).

TABLE 7

TLR2 Agonist Activity (EC$_{50}$ Values)
Calculated From Dose-Response Curves.

| Compd | EC$_{50}$ (nM) | Std. Error | R$^2$ Value |
| --- | --- | --- | --- |
| 3 | 56 | 1.1 | 0.99 |
| 8 | 25 | 1.1 | 0.99 |
| 9 | 78 | 1.1 | 0.99 |
| 10 | 20 | 1.0 | 0.99 |
| 11 | 204 | 1.3 | 0.97 |
| 12 | 39 | 1.1 | 0.98 |
| 13 | 34 | 1.2 | 0.98 |
| Pam$_2$CSK$_4$ | 3.7 | 1.4 | 0.96 |
| Pam$_3$CSK$_4$ | 23 | 1.5 | 0.94 |

In Cyto Binding Assays.

Figure 17A:
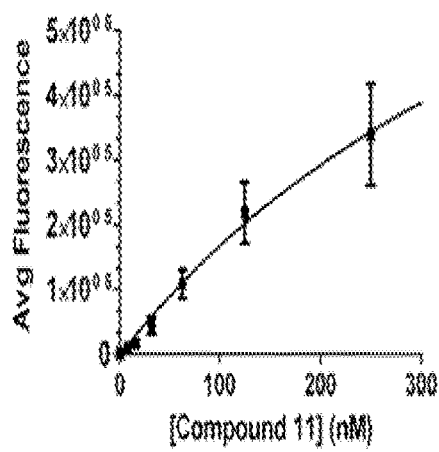
FIGS. 17A, 17B, and 17C show mean binding analysis curves generated by in cyto TRF binding assays. A) Saturation binding curve shows the specific binding (total—nonspecific) curve of Eu-DTPA labeled compound 11 to TLR2 using HEK-293/hTLR2 cells with a Kd of 34 nM and Bmax of 114,271 AFU (n=3 assays, R2 values>0.97). Competition binding analysis, in which increasing concentrations of test compound were added in the presence of 90 nM 11 using HEK-293/hTLR2 cells. B) Compound 10 had a Ki of 25 nM (n=5 assays, R2=0.90). C) Compound 13 had a Ki of 11 nM (n=4 assays, R2=0.87).
Figure 17B:
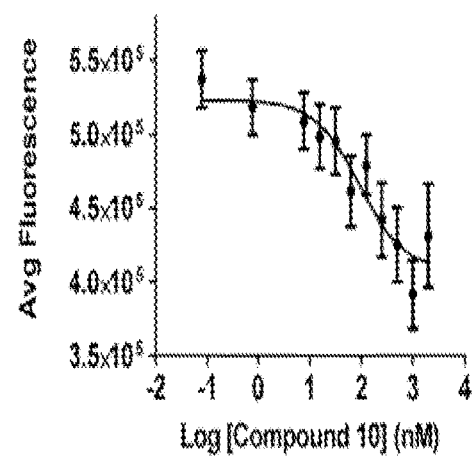
Figure 17C:
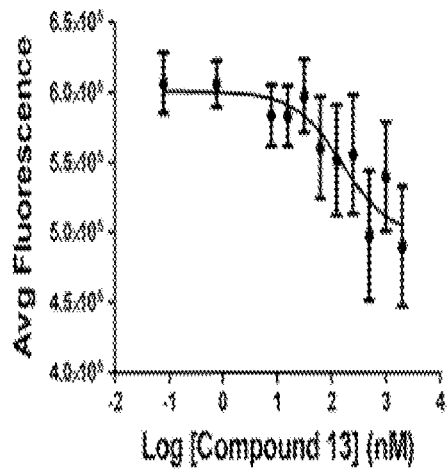
Figure 22A:
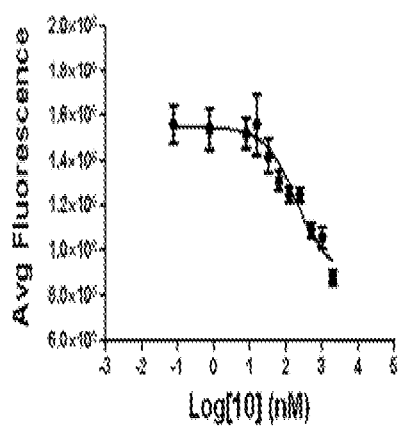
FIGS. 22A-22C show competition binding analysis, in which increasing concentrations of test compound were added in the presence of 90 nM compound 11 using SU.86.86 cells to determine TLR2 binding activity. A) Compound 10 had a K$_i$ of 91 nM (n=3 assays, R2=0.95). B) Compound 12 had a K$_i$ of 25 nM (n=4 assays, R$^2$=0.90). C) Compound 13 had a K$_i$ of 67 nM (n=4 assays, R$^2$=0.78).
Figure 22B:
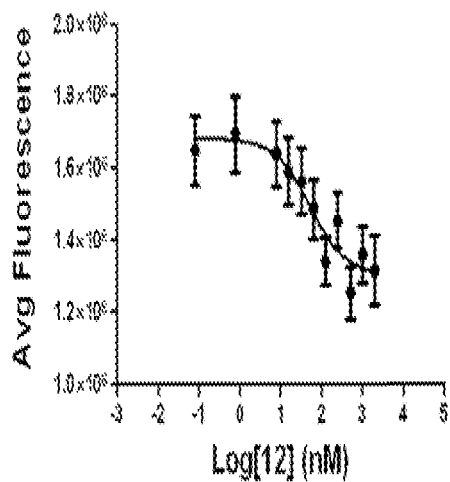
Figure 22C:
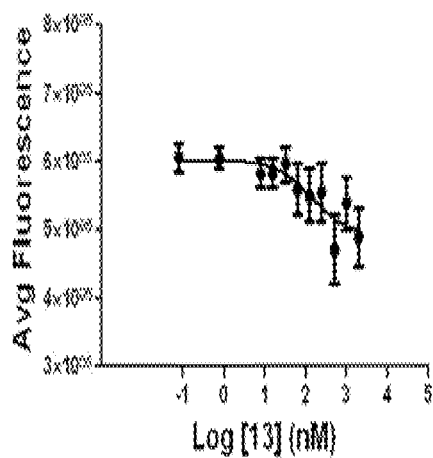

Lanthanide-based time-resolved fluorescence (TRF) saturation binding and competition binding assays were performed using TLR2 expressing cell lines. Saturation binding assays determined the Kd for the Eu-DTPA chelate labeled compound 11 was 34, 74 and 78 nM and Bmax was 114,271, 269,878 and 951,170 AFU for the HEK-293/hTLR2, SU.86.86, and Capan-I cells respectively (n>3 assays per cell line, R2 values>0.96) (Table 8, FIG. 17A and FIG. 21). Competitive binding assays using compound 11 as the competing ligand determined that the K$_i$ for compounds 10 and 13 is 25 and 11 nM in the HEK-293/hTLR2 cell line respectively; and 91 and 67 nM in the SU.86.86 cell line (n>4 assays, R2>0.78) (Table 9, FIGS. 17B and C and FIGS. 22A and C). Compound 12 exhibited the highest binding affinity in the SU.86.86 cell line with a Ki of 25 nM (n=4 assays, R2=0.90) (FIG. 22B).

TABLE 8

TLR2 Binding Affinity (K$_d$) for Compound 11
Determined by Saturation Binding Assays.

| TLR2 Expressing Cell line | K$_d$ (nM) | Std. Error | B$_{max}$ (AFU) | Std. Error | R$^2$ Value |
| --- | --- | --- | --- | --- | --- |
| HEK-293/hTLR2 | 34 | 13 | 114,271 | 17,001 | 0.97 |
| SU.86.86 | 74 | 16 | 269,878 | 28,809 | 0.99 |
| Capan-I | 78 | 22 | 951,170 | 112,968 | 0.96 |

TABLE 9

TLR2 Binding Affinity (K$_i$) Determined
by Competition Binding Assays.

| Compd | TLR2 Expressing Cell line | Ki (nM) | Std. Error | R$^2$ Value |
| --- | --- | --- | --- | --- |
| 10 | HEK-293/hTLR2 | 25 | 1.8 | 0.89 |
| 10 | SU.86.86 | 91 | 1.4 | 0.95 |
| 12 | SU.86.86 | 25 | 1.7 | 0.90 |
| 13 | HEK-293/hTLR2 | 11 | 1.8 | 0.87 |
| 13 | SU.86.86 | 67 | 2.3 | 0.78 |

In Vivo Immune Response.

Figure 18:
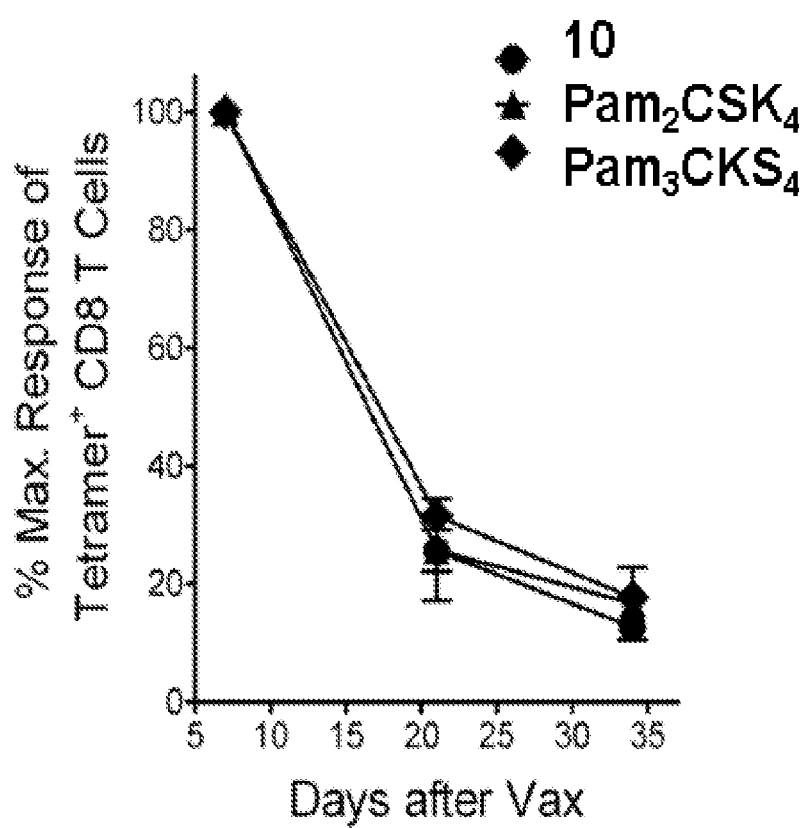
FIG. 18 shows mean maximum response of antigenspecific CD8 T cells in peripheral blood for up to 34 days post-immunization (n=3). Results represent the mean and SD (error bars) of three mice per experimental group. B6 mice were immunized i.v. with a mixture of Trp1455/9M peptide, anti-CD40 monoclonal antibody plus one of the following TLR2 agonists: 10, $Pam_2CSK_4$, or $Pam_3CSK_4$.
Figure 19:
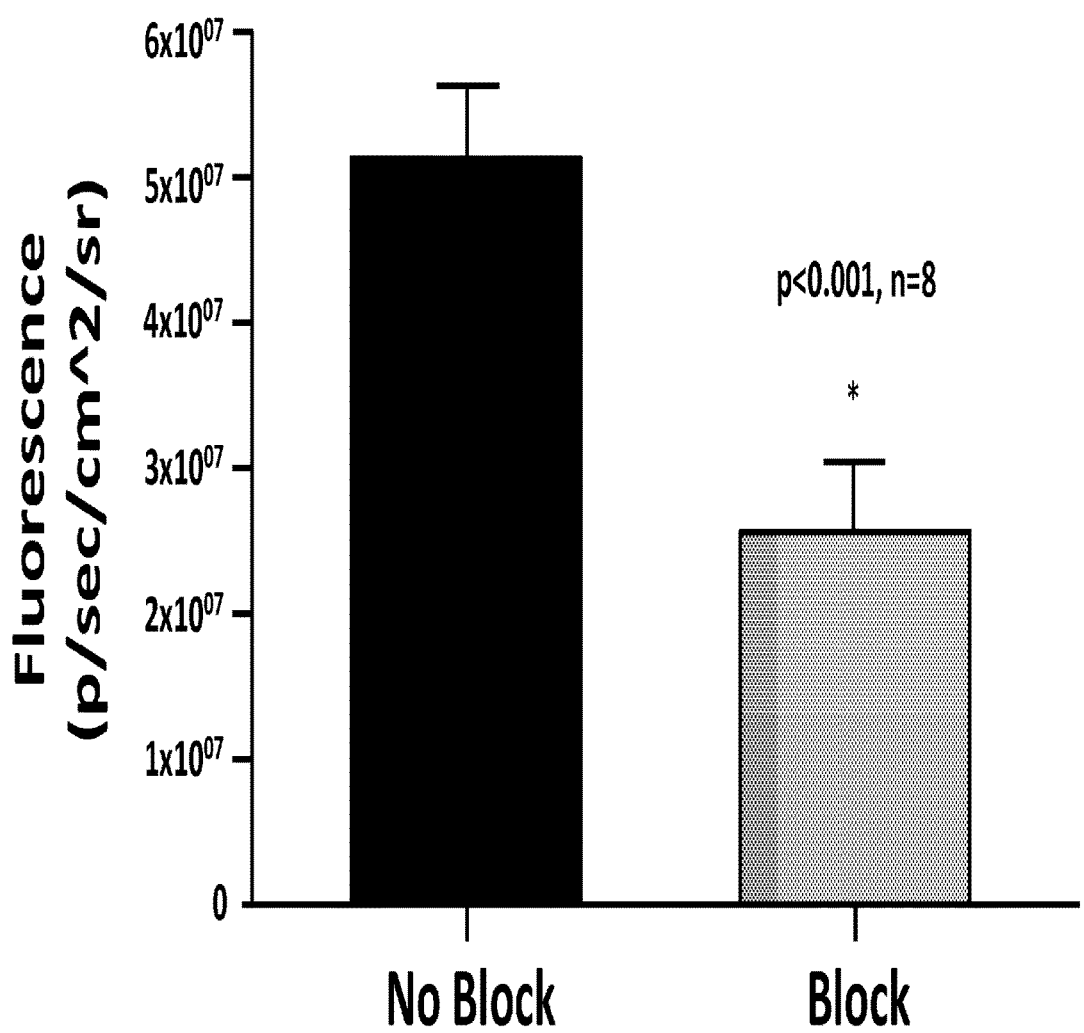
FIG. 19 shows comparison of representative fluorescence images of nude mice bearing TLR2 expressing tumor xenografts (SU.86.86 cells) acquired at 24 h, where the unblocked mice were administered 100 nmol/kg 13 and blocked mice were administered a co-injection of 100 nmol/kg 13 plus 2 μmol/kg Pam$_2$CSK$_4$ (20-fold excess). The graphed results show a significant reduction in the in vivo fluorescence signal was measured in the blocked tumors compared to the tumors that were not blocked (n=8, p<0.001), the mean increase in signal (unblocked tumor/blocked tumor) of 13 in the tumor was 1.94 fold.

Compound 10 was evaluated in vivo as an immune adjuvant and compared to the well-characterized commercially available synthetic TLR2 agonists, Pam$_2$CSK$_4$ and Pam$_3$CSK$_4$ in a peptide vaccine. The activity of each compound as an immune adjuvant was evaluated in vivo by measuring the Trp1455/9M-specific CD8 T cell responses in the blood on days 7, 21 and 34 post-immunization by flow cytometry analysis (n=3) (FIG. 18). The maximum amount of fluorescently stained tetramer positive CD8 T cells for 10, Pam$_2$CSK$_4$ and Pam$_3$CSK$_4$ observed on day 7 was 49.6%, 56.6% and 51.7% respectively. The 100% response rate of the tetramer positive CD8 T cells using 10 as immune adjuvant observed on day 7 decreased to an average of 25.7% on day 21 and 12.7% on day 34 which were comparable responses to using either Pam$_2$CSK$_4$ or Pam$_3$CSK$_4$ (FIG. 18). Therefore these results indicate that compound 10 exhibited activity similar to the other known TLR2 agonists, Pam$_2$CSK$_4$ and Pam$_3$CSK$_4$, for the generation and persistence of antigenspecific CD8 T cells. No signs or symptoms of stress or toxicity were observed in the mice over the course of the experiment.

In Vivo Tumor Selectivity.

Compound 13, conjugated to a near-infrared fluorescent dye, IRDye800CW, was used to determine in vivo TLR2 binding and selectivity for TLR2 expressing tumor xenografts (SU.86.86 cells). At 24 h post-injection, in vivo fluorescence imaging detected retention of fluorescence signal in the tumor. To determine the in vivo selectivity of 13 for TLR2, a blocking study was performed. A significant reduction in the tumor fluorescence was observed 24 h post-injection in the blocked group that received a 20-fold excess of $Pam_2CSK_4$ co-injected with 13 compared to the unblocked group receiving only 13 (p<0.001, n=8). The mean unblocked tumor fluorescence was 1.94-fold higher than the blocked. Ex vivo imaging confirmed that the fluorescence was associated with the tumors and that the blocked tumors had decreased fluorescence compared to the unblocked tumors. IHC staining confirmed TLR2 expression in the tumors.

Discussion and Conclusions

We first investigated the SAR of a set of novel, fully synthetic compounds (1-7) through manipulation at the N-terminal portion of MALP-2 derived LPs to enhance TLR2 specificity, potency and binding affinity. Our TLR2 functional bioassay determined that these seven compounds had human TLR2 agonist activities comparable to the reference compounds, $Pam_2CSK_4$ and $Pam_3CSK_4$. This result demonstrated that the addition of palmitoyl, fluorescein, Ac-PEGO, Ac-Aha, adapaleneyl, Ac-Aun and tretinoyl groups on MALP-2 derived LPs did not inhibit agonist activity.

The novel TLR2 agonist analogs (8-10) of compound 3 were designed to alter the chemical properties of the parent compound in order to identify SAR that contributes to increased specificity and binding affinity. This set of compounds was derived from different origins with the goal of altering the compound properties to be more acidic, hydrophilic and soluble. Attachment of a modified CD14 peptide (8) or the linker Gly-DSer-PEGO-NH2 (10) were both found to enhance the potency, with $EC_{50}$ values of 25 and 20 nM respectively, compared to 3 ($EC_{50}$=56 nM). The simplest and smallest compound (10), without inclusion of peptide, had the highest potency. Hence, the palmitoyl groups are the minimal binding/active component and the PEGO groups or peptides serve solely to increase solubility. The IRDye800CW fluorescent dye attachment (13) also exhibited a similar potency ($EC_{50}$=34 nM) to its unlabeled version (10) indicating that dye attachment did not significantly decrease TLR2 agonist activity. However the addition of Eu-DTPA chelate (11) resulted in a 10-fold decrease in potency ($EC_{50}$=204 nM). Compound 9 was synthesized by attachment of a *S. aureus* peptide to 3, decreasing the potency ($EC_{50}$=78 nM). The *S. aureus* peptide was predicted to be more acidic or at least neutral compared to SAA, with potential to improve potency. Indeed, 9 was observed to have 13-fold higher potency compared to SAA. The SAR of novel TLR agonist compounds is typically explored using various reporter gene or functional cell-based assays. [22] In order to discover high affinity binding ligands for development of TLR2 targeted agents, we developed a lanthanide-based TRF competition binding assay. We have previously been successful in the characterization of ligand binding affinities for other receptors using this method.[23] For this purpose, compound 11 was synthesized by attachment of Eu-DTPA chelate to the potent TLR2 agonist compound 10. Saturation binding confirmed the high TLR2 binding affinity of 11 (<100 nM Kd), which was then used as the competing ligand in competition binding assays that confirmed the high affinities of compounds 10, 12 and 13 (<100 nM Ki), which also correlated with high agonist potencies. Although 11 exhibited a 10-fold reduction in potency compared to 10, high binding affinity was achieved.

In performing the saturation binding assays with 11, we observed a difference in the $K_d$ values obtained in the HEK-293/hTLR2 cell line, which were genetically engineered to highly over express TLR2, compared to the 2 human pancreatic cells lines, SU.86.86 and Capan-1, that express lower endogenous levels of TLR2.[16] Similar results were also seen in the competition binding assays for both 10 and 13, in which a reduction in binding affinity for SU.86.86 cells was observed compared to the engineered cell line. Since these TRF binding assays are performed using living cells and the ligand incubation step is longer than the time needed for receptor mediated uptake, off rates may be reduced in a receptor dependent manner and differences observed in the $K_d$ and $K_i$ values obtained from the different cell lines is likely due to the varying levels of TLR2 expression.

Using TLR agonists as vaccine adjuvants is a promising application that has been explored to prevent and treat cancer. We have previously reported that the use of TLR agonists as immune adjuvants in peptide vaccination together with anti-CD40 monoclonal antibodies can increase the magnitude and duration of T-cell responses resulting from various types of immunizations including peptide vaccines.[10a, b] Results herein show that compound 10 induced an in vivo immune response comparable to the currently available TLR2 synthetic agonists ($Pam_2$- & $Pam_3CSK_4$) demonstrating that it can function as an immune adjuvant for use in cancer immunotherapy. Others have also reported that TLR2 agonistic LPs, based on the $Pam_2CS$ platform, have a potential role as vaccine adjuvants.[24] It is also worth noting that no signs or symptoms of stress or toxicity were observed in the mice over the course of the study. Kimbrell et al. reported that LPs are extremely potent TLR2 agonists in vivo with no apparent toxicity in animal models.[25]

The use of TLR2 agonist ligands in targeted pancreatic cancer imaging and treatment was explored. We demonstrated the tumor specific retention of the fluorescently labeled compound 13, in vivo, using mice bearing TLR2 expressing xenografts (SU.86.86 cells). Since we previously identified TLR2 as a pancreatic cancer cell surface marker expressed in over 70% of pancreatic tumors but not in normal pancreas tissue, the TLR2 ligand compounds, especially compound 13, can be used for intraoperative detection of pancreatic cancer leading to increased negative resection margins and increased pancreatic cancer survival.

Experimental Section

Compound Synthesis, Acquisition and Preparation.

Compounds were prepared as previously published by solid-phase synthesis on Rink Amide Tentagel resin (0.23 mmol/g) using Fmoc/tBu synthetic strategy and standard DIC-HOBt and HBTU or HCTU activations.[26] The synthesis was performed in fitted syringes using a Domino manual synthesizer obtained from Torviq (Niles, Mich.). For compound 3, 8-13, an Fmoc-protected version of PEGO (Novabiochem, San Diego, Calif.) was used and an Fmoc-protected derivative of Cys, Fmoc-Cys(S-[2,3-bisacyloxy-(R)-propyl])-OH (Fmoc-Dhc(Pam2)-OH) was synthesized as described in Example 19.[27] All compounds were fully deprotected and cleaved from the resin by treatment with 91% TFA (3% water, 3% EDT, and 3% TA) or 90% TFA (5% water, 5% TIS). After ether extraction of scavengers, compounds were purified by HLPC and/or size-exclusion chromatography (Sephadex G-25, 0.1 M acetic acid) to >95% purity. All compounds were analyzed for purity by analytical HPLC and MS by ESI or MALDI-TOF (synthetic details are in Example 19).

Materials.

Nα-Fmoc protected amino acids, HBTU, and HOBt were purchased from SynPep (Dublin, Calif.) or from Novabiochem (San Diego, Calif.) Rink amide Tentagel S resin was acquired from Rapp Polymere (Tubingen, Germany). HOCt, DIC and DIEA were purchased from IRIS Biotech (Marktredwitz, Germany). The following side chain protecting groups were used for the amino acids: Arg($N^g$-Pbf); Asn ($N^{am}$-Trt); Asp(OtBu); Glu(O-tBu); His($N^{im}$-Trt); Ser(tBu), DSer(tBu), Lys($N^\varepsilon$-Boc). An Fmoc-protected version of PEGO was purchased from Novabiochem. IRDye800CW maleimide was kindly provided by LI-COR (Lincoln, Nebr.). Adapalene was purchased from AK Scientist (aksci.com). Peptide synthesis solvents, dry solvents, and solvents for HPLC (reagent grade), and trans-Retinoic acid, were acquired from VWR (West Chester, Pa.) or Sigma-Aldrich (Milwaukee, Wis.), and were used without further purification unless otherwise noted. Compounds were manually assembled using 5 to 50 mL plastic syringe reactors equipped with a frit, and a Domino manual synthesizer obtained from Torviq (Niles, Mich.). The C-18 Sep-Pak™ Vac RC cartridges for solid phase extraction were purchased from Waters (Milford, Mass.).

Peptide Synthesis.

Ligands were synthesized on Tentagel Rink amide resin (initial loading: 0.2 mmol/g) using Nα-Fmoc protecting groups and a standard DIC/HOCt or HBTU/HOBt activation strategy. The resin was swollen in THF for an hour, washed with DMF, and the Fmoc protecting group removed with 20% piperidine in DMF (2 min+20 min). The resin was washed with DMF (3×), DCM (3×), 0.2 M HOBt in DMF (2×), and finally with DMF (2×) and the first amino acid coupled using pre-activated 0.3 M HOCt ester in DMF (3 eq. of Nα-Fmoc amino acid, 3 eq. of HOCt and 6 eq. of DIC). An on-resin test using Bromophenol Blue was used for qualitative and continuous monitoring of reaction progress. To avoid deletion sequences and slower coupling rate in longer sequences, the double coupling was performed at all steps with 3 eq. of amino acid, 3 eq. of HBTU and 6 eq. of DIEA in DMF. Wherever beads still tested Kaiser positive, a third coupling was performed using the symmetric anhydride method (2 eq. of amino acid and 1 eq. of DIC in dichloromethane). Any unreacted $NH_2$ groups on the resin thereafter were capped using an excess of 50% acetic anhydride in pyridine for 5 min. When the coupling reaction was finished, the resin was washed with DMF, and the same procedure was repeated for the next amino acid until all amino acids were coupled. Fmoc-PEGO, FmocAha, Fmoc-Aun, Tretinoic acid, Adapalene, and Fluorescein were attached to the resin as symmetrical anhydride (6 eq of acid and 3 eq of DIC in DCMDMF).

Cleavage of Ligand from the Resin.

A cleavage cocktail (10 mL per 1 g of resin) of TFA (91%), water (3%), triisopropylsilane (3%), and 1,2-ethylenedithiol (3%) was injected into the resin and stirred for 4 h at room temperature. Alternatively, a cleavage cocktail of 90% trifluoroacetic acid (5% water, and 5% triisopropylsilane) was used. The crude ligand was isolated from the resin by filtration, the filtrate was reduced to low volume by evaporation using a stream of nitrogen, and the ligand was precipitated in ice-cold diethyl ether, washed several times with ether, dried, dissolved in water and lyophilized to give off-white solid powders that were stored at −20° C. until purified. The crude compound was purified by size-exclusion chromatography.

Synthesis of Compound 11, Eu-DTPA Labeled Ligand.

Attachment of DTPA to the N-terminus of was performed using preformed HOBt activation (3 equiv. of DTPA anhydride and 6 equiv. of HOBt, Scheme 1). DTPA was attached to H-PEGODhc($Pam_2$)-Gly-DSer-PEGO-resin as follows. Briefly, DTPA anhydride (3 equiv.) and HOBt (3 equiv.) in DMSO were heated until dissolved (60° C.) then stirred for 30 minutes at room temperature. The preformed DTPA-OBt diester was injected into the free-amine H-PEGO-Dhc($Pam_2$)-Gly-DSer-PEGO-resin and stirred overnight. The resin was washed with DMSO, THF, 5% DIEA 5% water in THF (5 minutes), THF, and DCM. The compound was cleaved from the resin as described above and purified by HPLC. The purified peptide was dissolved in 0.1 M ammonium acetate buffer pH 8.0, 3.0 eq. Eu(III)$Cl_3$ was added and the reaction was stirred at room temperature overnight. The Eu-labeled peptide was separated using Solid-Phase Extraction (SPE) and lyophilized to yield an amorphous white powder. The final compound was characterized by HPLC (TEAA buffer pH 6.0), ESI-MS and/or FT-ICR.

Synthesis of Compounds 12 and 13.

Attachment of Trt-Mpr-OH(S-trityl-3-mercaptopropionic acid) to the N-terminus H-PEGO-Dhc(Pam2)-Gly-DSer-PEGO-resin was performed using preformed HBTU activation (3 equiv. of Trt-Mpr-OH, 3 equiv. of HBTU and 6 equiv. of DIEA in DMF) (Scheme 1). The resin was washed with DMF and DCM. The compound 12 was cleaved from the resin as described above and purified by HPLC.

The compound 12 H-Mpr-PEGO-Dhc($Pam_2$)-Gly-DSer-PEGO-$NH_2$ (1 µmol) was dissolved in 1 mL DMF and reacted with 1 equiv. of IRDye800CW maleimide under argon atmosphere. The reaction was monitored by HPLC and additional aliquots (0.1 equiv.) of dye were added until the reaction complete. The compound was purified by HPLC.

Purification and Analysis.

Purity of the peptides was ensured using analytical HPLC (Waters Alliance 2695 separation model with a dual wavelength detector Waters 2487) with a reverse-phase column (Waters Symmetry, 3.0·75 mm, 3.5 µm; flow rate=0.3 mL/min). (Conditions: HPLC pH 2, linear gradient from 10 to 90% B over 30 min, where A is 0.1% TFA and B is acetonitrile or THF, HPLC pH 6, linear gradient from 10 to 90% B over 30 min, where A is 0.1% TEAA and B is acetonitrile or THF). Size exclusion chromatography was performed on a borosilicate glass column (2.6×250 mm, Sigma, St. Louis, Mo.) filled with medium sized Sephadex G-25 or G-10. The compounds were eluted with an isocratic flow of 1.0 M aqueous acetic acid. Solid-Phase Extraction (SPE) was employed where simple isolation of final compound was needed from excess salts and buffers for e.g., lanthaligand synthesis. For this purpose, C-18 Sep-Pak™ cartridges (100 mg or 500 mg) were used and pre-conditioned initially with 5 column volumes (5 times the volume of packed column bed) each of acetonitrile, methanol, and water, in that order. After loading the compound, the column was washed several times with water, and then gradually with 5, 10, 20, 30, 50, and 70% of aqueous acetonitrile to elute the peptide. Structures were characterized by ESI (Finnigan, Thermoquest LCQ ion trap instrument), MALDI-TOF or FT-ICR mass spectrometry. An appropriate mixture of standard peptides was used for internal calibrations.

The test compounds (1-13) were dissolved in DMSO at a 1 mg/mL concentration as stock solutions stored at −20° C.

For biological experimental use, 10 µg/mL working solutions of the compounds were prepared from stock solutions in sterilized, deionized water and used immediately.

Commercially available synthetic TLR2 agonists were used as references: $Pam_2CSK_4$ and $Pam_3CSK_4$ were purchased from InvivoGen (San Diego, Calif.) and recombinant human apo-SAA1 was purchased from PeproTech (Rocky Hill, N.J.).

$Trp1_{455/9M}$ (TAPDNLGYM) is an H2 $D^b$-optimized peptide for MHC class I binding[10c] was obtained from A&A Labs (San Diego, Calif.). Rat anti-mouse CD40 monoclonal antibody was prepared from the FGK45.5 hybridoma culture supernatants.[10a] FITC-conjugated anti-MHC class II and PerCP Cy5.5-conjugated CD8a antibodies were both purchased from eBioscience (San Diego, Calif.). Phycoerythrin-conjugated $Trp1_{455/9M}/H-2D^b$) tetramers were provided by the NIH Tetramer Facility, Emory University (Atlanta, Ga.).

Cell Culture.

The parental HEK-293 cells (ATCC CRL-1573) and Capan-I cells (ATCC HTB-79) were cultured in DMEM/F12 media (Life Technologies Gibco) supplemented with 10% normal calf serum (NCS) (Atlanta Biologicals, Lawrenceville, Ga.) and 1% penicillin/streptomycin solution (Sigma). The HEK-293/hTLR2 cells (InvivoGen, San Diego, Calif.) were cultured in DMEM/F12 media supplemented with 10% NCS, 1% penicillin/streptomycin solution, 10 µg/mL blasticidin (InvivoGen). The SU.86.86 cells (ATCC CRL-1837) were grown in RPMI 1640 media (Life Technologies Gibco) supplemented with 10% NCS. All cells were grown at 37° C. and 5% $CO_2$.

The HEK-293/hTLR2 cells were genetically engineered to highly overexpress TLR2 by stable transfection of the parental HEK-293 cells with pUNO-hTLR2 plasmid expressing the human TLR2 gene.[28] The expression of human TLR2 in HEK-293/hTLR2 cells and absence in the parental HEK-293 cells was confirmed by RT-PCR and western blot analysis. RT-PCR and western blot expression of TLR2 on the cell surface of HEK-293/hTLR2 expressing cells with no expression in the parental HEK293 cells was tested. A band was observed at approximately 90 kDa. Optimal NF-κB induced expression of luciferase led to observed luminescence 48 h post transient transfection and 24 h post ligand stimulation. Luminescence intensity was significantly greater (50 fold, n=6, p<0.001) in TLR2 ligand ($Pam_3CSK_4$) stimulated HEK293/hTLR2 cells relative to cells incubated with no ligand. No activity was observed with the HEK293 TLR2 negative expressing cells (n=3 assays with quadruplicate wells). The 2 human pancreatic cells lines used in our studies, SU.86.86 and Capan-I, express lower endogenous levels of TLR2.[16]

In Vitro TLR2 Functional Bioassay.

The in vitro TLR2 functional bioassay was developed and optimized for use in high-throughput screening of soluble compound libraries to identify both TLR2 agonists and antagonists. The bioassay measures the induction of NF-κB signaling via TLR2 in HEK-293/hTLR2 cells and parental HEK-293 cells as a negative control. Cells were seeded at a density of 40,000 per well using a WellMate Microplate dispenser (Thermo Fisher Scientific/Matrix) in black 96-well plates with opaque white wells (PerkinElmer, Waltham, Mass.) and then incubated at 37° C. On day 2, the cells were transiently transfected with pNifty-Luc (InvivoGen, San Diego, Calif.), an NF-κB inducible reporter plasmid expressing the luciferase reporter gene[28] using an optimized 4:1 ratio by volume of FugeneHD Transfection Reagent (Promega, Madison, Wis.) to pNifty-Luc plasmid DNA (1 µg/mL). On day 3, the cells were stimulated with either test peptides or controls adjusted to a final concentration of 1 µg/mL using a NanoDrop Spectrophotometer, ND1000 (Thermo Fisher Scientific). Synthetic di- and tri-acylated LP ligands, $Pam_2CSK_4$ and $Pam_3CSK_4$ (InvivoGen), were used as positive controls, TNF-α (InvivoGen) was also used as a transfection control that induces NF-κB independently of TLR2. On day 4 after 24 h of peptide stimulation, luciferase induced activity by the induction of NF-κB was measured. Media was aspirated from the wells using an ELx405 Select CW plate washer (BioTek, Winooski, Vt.), 150 µg/mL D-luciferin (Gold Biotechnology, St. Louis, Mo.) was dispensed using the microplate dispenser; the plates were incubated at 37° C. for 5 min. The luminescence intensity was measured using the standard luminescence protocol on a Victor X4 Multilabel plate reader equipped with a plate stacker for readout of multiple plates at a time (PerkinElmer, Waltham, Mass.). For each in vitro TLR2 bioassay, at least three different experiments were performed in triplicate (n≥3). Data were analyzed with GraphPad Prism software and curves were generated with the appropriate nonlinear fit regression analysis.

In Cyto Europium Time-Resolved Fluorescence Binding Assays.

Europium TRF binding assays were performed as previously described with slight modifications using 3 cell lines that express TLR2: HEK-293/hTLR2, SU.86.86, and Capan-I.[23a, 23d, 29] The Capan-I and SU.86.86 cells were plated in 96-well black plates with white opaque wells (PerkinElmer); while the HEK-293/hTLR2 cells were plated on 96-well poly-D-lysine coated plates (Sigma-Aldrich) to aid in the attachment of these cells to the plate. Cells were grown in the 96-well plates for 2 days reaching approximately 80% confluency. Both types of plates were evaluated for nonspecific binding and background signal.

For saturation binding, increased concentrations of the labeled ligand, compound 11 (Table 8), were used to determine total binding to TLR2. Non-specific binding was determined in the presence of 1 µM $Pam_2CSK_4$. On the day of the experiment the medium was aspirated. 50 µL of binding buffer was added to the total binding wells and 50 µL of $Pam_2CSK_4$ was added to the non-specific wells and then allowed to incubate for 30 m at 37° C. Next, 50 µL of the serial dilutions of 10 were added and then allowed to incubate for 1 h at 37° C. Cells were washed three times to remove unbound ligand. Next, 100 µL of DELFIA Enhancement Solution (PerkinElmer) was added to each well. Cells were incubated for 30 min at 37° C. prior to reading. The plates were read on the VICTOR X4 Multilabel plate reader using the standard europium TRF protocol (340 nm excitation, 400 µs delay and 400 us emission collection at 615 nm). To determine the mean $K_d$, statistical analysis was performed using GraphPad Prism software.

Competition binding assays were performed to test the TLR2 binding specificity of the test ligands using 2 cell lines: HEK-293/hTLR2 and SU.86.86. Cells were grown in 96-well plates for 2 days reaching approximately 80% confluency. On the day of the experiment, the cell culture media was aspirated and 50 µL of non-labeled test ligand was added in a series of decreasing concentrations (1 µM to 0.01 nM) followed by 50 µL of the competing Eu-labeled ligand 10 at a fixed concentration of 90 nM. Cells were incubated with labeled and unlabeled ligands for 1 h at 37° C. Following incubation, cells were washed three times to remove unbound ligand. Next, 100 µL of DELFIA Enhancement Solution (PerkinElmer) was added to each well. Cells were incubated for 30 min at 37° C. prior to reading. The plates were read on PerkinElmer VICTOR X4 Multilabel reader using the standard europium TRF protocol. To determine the mean Ki, statistical analysis was performed using GraphPad Prism software.

Animal Studies.

All procedures were in compliance with the Guide for the Care and Use of Laboratory Animal Resources (1996), National Research Council, and approved by the Institutional Animal Care and Use Committee, University of South Florida. Mice are housed in a clean facility with special conditions that include HEPA filtered ventilated cage systems, autoclaved bedding, autoclaved housing, autoclaved water, irradiated food and special cage changing procedures. Mice are handled under aseptic conditions including the wearing of gloves, gowns and shoe coverings.

In Vivo Cellular Immune Response Assays.

C57BL/6 (B6) mice 6-8 weeks old were purchased from Charles River (Wilmington, Mass.). To assess the efficacy of 10 as an immune adjuvant, B6 mice were immunized i.v. with a mixture (in a volume of 200 µl) of 100 µg optimized Trp1455/9M peptide,[10c] 50 µg anti-CD40 monoclonal antibody (Clone; FGk-45.5), and 50 µg TLR2 agonist (10, Pam$_2$CSK$_4$, or Pam$_3$CSK$_4$). The Trp1$_{455/9M}$ peptide was tested using the TLR2 functional bioassay, it was determined that it is not a TLR2 agonist. The response of tetramer positive CD8 T cells in the blood was measured on day 7, 21 and 34 by tetramer staining. For tetramer staining, peripheral blood was taken from the submandibular vein and treated briefly with ammonium chloride buffer to lyse red blood cells. Blood cells were stained with FITC-conjugated anti-MHC class II, PerCP Cy5.5-conjugated CD8a, and phycoerythrin-conjugated Trp1$_{455/9M}$/H-2D$^b$ tetramers for 40 min in ice. Fluorescence was evaluated using a FACSCalibur flow cytometer (BD Biosciences) and analyzed using FlowJo software.

In Vivo TLR2 Selectivity Experiment.

Female athymic nude mice 6-8 weeks old (Harlan) bearing human pancreatic tumor xenografts consisting of SU.86.86 cells on the right flank were used for this study. Mouse weights and tumor volumes were determined using caliper measurements and the formula: volume (mm3)=(length×width)/2. Images were acquired when the tumors reached an average size of 500 mm$^3$. For the blocked group, a co-injection of 100 nmol/kg of the fluorescently labeled compound 13 plus 2 µmol/kg Pam$_2$CSK$_4$ (a 20-fold excess) was administered via tail vein injection; for the unblocked group, 100 nmol/kg 13 was administered. Fluorescence images were acquired at time 0 and 24 h using the Caliper Xenogen IVIS200 system (PerkinElmer) with the 710-760 nm excitation and 810-875 nm emission filter set. The fluorescence was quantified using Living Image software, in which the quantified signals were corrected for both instrument and mouse background subtractions. The quantified fluorescence was then plotted using GraphPad Prism software and underwent statistical analysis using Student's t-test.

For further confirmation of ligand 13 specificity for TLR2, ex vivo fluorescence imaging and histological analyses were performed on the tumors. For histological analyses the samples were fixed in 10% formalin solution, processed, embedded, sectioned and either H&E stained for the presence of tumor or underwent IHC staining using TLR2 antibody (Abcam #ab24192).

Statistical Analysis.

The results are represented as mean±s.d. and statistically evaluated by Student's t test to determine statistical significance.

ABBREVIATIONS

Abbreviations used for amino acids and designation of peptides follow the rules of the IUPAC-IUB Commission of Biochemical Nomenclature in *J. Biol. Chem.* 1972, 247, 977-983. The following additional abbreviations are used: Boc, tert-butyloxycarbonyl; BB, bromophenol blue; t-Bu, tert-butyl; CH$_3$CN, acetonitrile; DCM, dichloromethane; DI, de-ionized; DIPEA, diisopropylethylamine; Dhc, 2,3-dihydroxypropylcysteine or Cys(S-[2,3-hydroxy-(R)-propyl] residue; DMF, N,N-dimethylformamide; DIC, diisopropylcarbodiimide; DMEM, Dulbecco's Modified Eagle Medium; Eu-DTPA, europium diethylenetriaminepentaacetic acid; Fmoc, 9-fluorenylmethoxycarbonyl; FTICR, Fourier Transform-Ion Cyclotron Resonance; ESI-MS, Electrospray ionization mass spectrometry; EDT, 1,2-ethanedithiol; Et$_2$O, Diethyl ether; HBSS, Hank's Balanced Saline Solution buffered with 25 mM Hepes; HCTU, O-[1H-6-chloro-benzotriazol-1-yl)(dimethylamino) ethylene] uraniumhexafluorophosphateN-oxide; HEPES, 4-(2-hydroxyethyl)-1-piperazineethanesulfonic acid; HOBt, N-hydroxybenzotriazole; HOCt, 6-chloro-1-hydroxybenzotriazole; LP, lipopeptide; MALDI-TOF, Matrix Assisted Laser Desorption Ionization-Time of Flight; MALP-2, macrophage-activating lipopeptide 2; Mpr, 3-mercaptopropionic residue; PAMP, pathogen-associated molecular patterns; Pbf, 2,2,4,6,7-pentamethyl-dihydrobenzofuran-5-sulfonyl; PEGO, 19-amino-5-oxo-3,10,13,16-tetraoxo-6-azanonadecan-1-oic acid residue; PRR, pattern recognition receptor; SPPS, solid-phase peptide synthesis; RP-HPLC, reverse-phase high performance liquid chromatography; SAA, serum amyloid a; SAR, structure activity relationship; TA, thioanisole; THF, tetrahydrofuran; TIR, toll/interleukin receptor; TIS, triisopropylsilane; TFA, trifluoroacetic acid; TLR2, toll-like receptor 2; TNF-α, tumor necrosis factor α; TRF, time resolved fluorescence; Trt, trityl.

Example 19: Synthesis

Synthesis of N-Fluorenylmethoxycarbonyl-S-[2,3-bis(palmitoyloxy)-(2R)-propyl]-(R)-cysteine (3R) (Fmoc-Dhc(Pam₂)-OH)

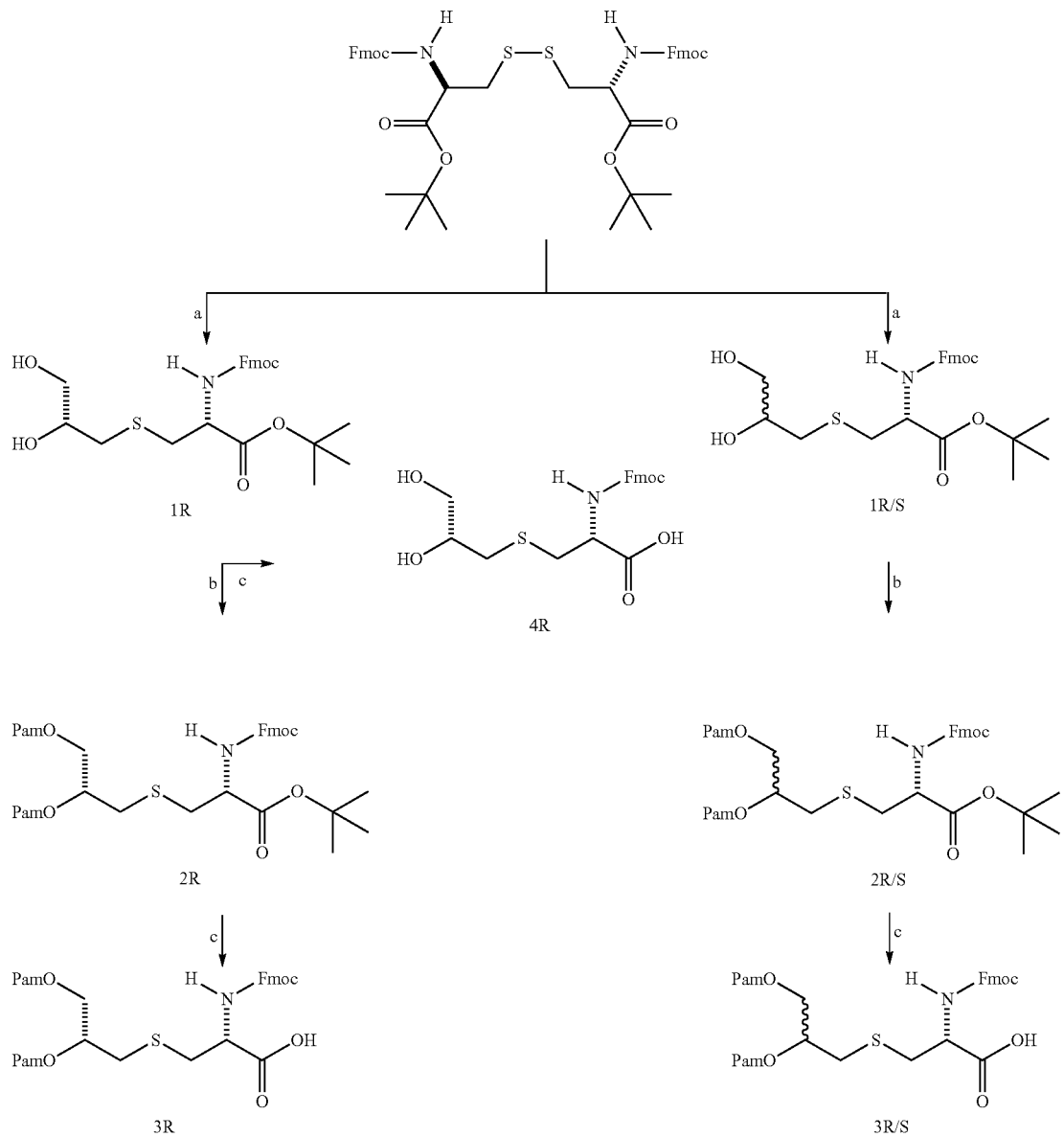

(a) i) Zn, CH$_2$Cl$_2$, MeOH:HCl:H$_2$SO$_4$ (100:7:1), r.t. 15 m im. ii) Glycidol, 40° C., 5 hr. (iii) KHSO$_4$, 0° C. to r.t. 16 hr. (b) Polmitoyl chloride, DMAP, TEA, CH$_2$Cl$_2$:DMF (100:1), 0° C. to r.t. 3 hr. (c) TFA, r.t. 1 hr.

General.

All reactions were conducted under Ar atmosphere using oven-dried glassware. All chemicals were obtained from commercial sources and used without further purification. $^1$H NMR spectra were recorded on Bruker-DRX-300 MHz instrument with chemical shifts reported relative to TMS (0.0 ppm) and residual DMSO (2.50 ppm). Proton-decoupled $^{13}$C NMR spectra were referenced to CDCl$_3$ (77.0 ppm) as well as DMSO (39.51 ppm). Low resolution mass spectra were obtained on AGILENT (HP) MDS 1100 using AP-ESI. High resolution mass spectra (HRMS) were recorded on a Bruker FT-ICR MS 9.4T instrument. Melting points were measured using a Thomas Hoover capillary melting point apparatus and are uncorrected.

Synthesis of N-Fluorenylmethoxycarbonyl-S-[2,3-dihydroxy-(2RS)-propyl]-(R)-cysteine tert-butyl ester (1R/S)

To a solution of (Fmoc-Cys-O$^t$Bu)$_2$ (1.91 g, 2.4 mmol) in dichloromethane (15 mL) was added Zn (1.10 g, 16.8 mmol). A freshly prepared mixture (8 mL) of MeOH:32% HCl:concentrated H$_2$SO$_4$ (100:7:1=v:v:v) was added under vigorous stirring at room temperature. After 15 minutes (±)-glycidol (1.78 g, 24 mmol) was added and the resulting mixture was stirred for 5 hours at 40° C. The mixture was concentrated to about half of the original volume and cooled to 0° C., then 5% KHSO$_4$ aqueous solution (2 mL) was added and stirred for 16 hours with warming-up to room temperature slowly. The mixture was extracted with dichloromethane and the organic layer was washed with water, dried over anhydrous MgSO$_4$, filtered and concentrated. The residue was purified by silica gel column chromatography using a mixture of dichloromethane and methanol (40:1=v:v) to give N-Fluorenylmethoxycarbonyl-S-[2,3-dihydroxy-(2RS)-propyl]-(R)-cysteine tert-butyl ester (1R/S, 2.26 g) as colorless oil in 99% isolated yield.

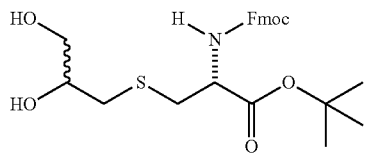

Colorless oil; $^1$H NMR (300 MHz, CDCl$_3$), two diastereoisomers δ 1.50 (s, 9H), 2.04-2.14 (m, 1H), 2.59-3.20 (m, 5H), 3.48-3.59 (m, 1H), 3.65-3.85 (m, 2H), 4.24 (t, J=6.98 Hz, 1H), 4.35-4.45 (m, 2H), 4.46-4.56 (m, 1H), 5.72-5.84 (m, 1H), 7.32 (t, J=7.40 Hz, 2H), 7.41 (t, J=7.41 Hz, 2H), 7.61 (d, J=7.29 Hz, 2H), 7.77 (d, J=7.37 Hz, 2H); $^{13}$C NMR (75 MHz, CDCl$_3$) two diastereoisomers δ 28.0, (35.7, 35.8), (36.6, 36.7), 47.0, 54.4, (65.0, 65.2), (67.16, 67.19), (70.3, 70.5), 83.2, 120.0, 125.1, 127.0, 127.7, 141.2, 143.66, 143.72, (156.0, 156.07), (169.62, 169.65); LRMS (ESI) m/z Calcd for C$_{25}$H$_{31}$NO$_6$SNa (M+Na)$^+$ 496.2, obsd 496.0.

Synthesis of N-Fluorenylmethoxycarbonyl-S-[2,3-dihydroxy-(2R)-propyl]-(R)-cysteine tert-butyl ester (1R)[1-2]

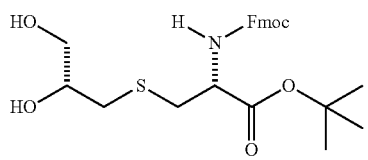

The title compound was synthesized according to the procedure described for compound (1R/S) starting from (Fmoc-Cys-O$^t$Bu)$_2$ (5.74 g, 7.2 mmol) and R-(+)-glycidol (5.33 g, 72 mmol). N-Fluorenylmethoxycarbonyl-S-[2,3-dihydroxy-(2R)-propyl]-(R)-cysteine tert-butyl ester (1R, 5.70 g) was obtained as a viscous oil in 84% isolated yield.

Colorless oil; $^1$H NMR (300 MHz, CDCl$_3$) δ 1.49 (s, 9H), 2.39 (t, J=5.94 Hz, 1H), 2.63 (dd, J=13.7, 8.40 Hz, 1H), 2.75-2.82 (m, 1H), 2.93 (dd, J=14.0, 6.10 Hz, 1H), 3.03 (dd, J=14.0, 4.60 Hz, 1H), 3.33 (d, J=3.63 Hz, 1H), 3.48-3.55 (m, 1H), 3.64-3.72 (m, 1H), 3.75-3.84 (m, 1H), 4.23 (t, J=7.07 Hz, 1H), 4.39 (d, J=7.07 Hz, 2H), 4.49-4.55 (m, 1H), 5.87 (d, J=7.97 Hz, 1H), 7.31 (t, J=7.40 Hz, 2H), 7.41 (t, J=7.36 Hz, 2H), 7.61 (d, J=7.29 Hz, 2H), 7.77 (d, J=7.44 Hz, 2H); $^{13}$C NMR (75 MHz, CDCl$_3$) δ 28.0, 35.8, 36.8, 47.0, 54.4, 65.2, 67.2, 70.5, 83.2, 120.0, 125.1, 127.1, 127.7, 141.3, 143.66, 143.75, 156.0, 169.7; LRMS (ESI) m/z Calcd for C$_{25}$H$_{31}$NO$_6$SNa (M+Na)$^+$ 496.2, obsd 496.0.

Synthesis of N-Fluorenylmethoxycarbonyl-S-[2,3-bis(palmitoyloxy)-(2RS)-propyl]-(R)-cysteine tert-butyl ester (2R/S)[1-2]

To a mixture of compound 1R/S (1.56 g, 3.28 mmol) and palmitoyl chloride (2.71 g, 9.85 mmol) in a mixture (35 mL) of CH$_2$Cl$_2$ and DMF (100:1=v:v) was added triethylamine (997 mg, 9.85 mmol), followed by DMAP (80.3 mg, 0.657 mmol) at 0° C. The resulting mixture was stirred at 0° C. for 30 minutes and at room temperature for 3 hours. The reaction was quenched by an addition of saturated NaCl aqueous solution and extracted with dichloromethane. The organic layer was washed with water, dried over anhydrous MgSO$_4$, filtered and concentrated. The residue was purified by silica gel column chromatography using a mixture of hexanes and ethyl acetate (9:1=v:v) to give N-Fluorenylmethoxycarbonyl-S-[2,3-bis(palmitoyloxy)-(2RS)-propyl]-(R)-cysteine tert-butyl ester (2R/S, 2.60 g) as white solid in 83% isolated yield.

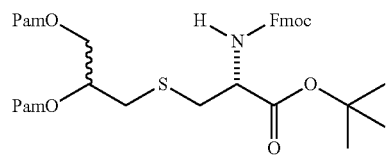

White solid, mp=52-54° C. (lit.$^2$ 38-42° C.); $^1$H NMR (300 MHz, CDCl$_3$), two diastereoisomers δ 0.879 (t, J=6.88 Hz, 6H), 1.25 (br, 48H), 1.49 (s, 9H), 1.55-1.64 (br, 4H), 2.26-2.33 (m, 4H), 2.77 (d, J=6.39 Hz, 2H), 3.00-3.13 (m, 2H), 4.12-4.18 (m, 1H), 4.22-4.40 (m, 4H), 4.48-4.55 (m, 1H), 5.10-5.20 (m, 1H), 5.69 (t, J=6.34 Hz, 1H), 7.29-7.34 (m, 2H), 7.40 (t, J=7.39 Hz, 2H), 7.62 (d, J=7.47 Hz, 2H), 7.77 (d, J=7.47 Hz, 2H); $^{13}$C NMR (75 MHz, CDCl$_3$) two diastereoisomers δ 14.1, 22.7, 24.85, 24.87, 28.0, 29.1, 29.3, 29.4, 29.5, 29.66, 29.70, 31.9, (33.17, 33.24), 34.1, 34.2, (35.33, 35.38), 47.1, (54.26, 54.29), (63.40, 63.43), 67.2, (70.19, 70.26), 83.0, 120.0, 125.2, 127.1, 127.7, 141.3, 143.8, (155.66, 155.69), 169.5, (173.0, 173.04), 173.3; LRMS (ESI) m/z Calcd for C$_{57}$H$_{91}$NO$_8$SNa (M+Na)$^+$ 972.6, obsd 972.5.

Synthesis of N-Fluorenylmethoxycarbonyl-S-[2,3-bis(palmitoyloxy)-(2R)-propyl]-(R)-cysteine tert-butyl ester (2R)[1-2]

The title compound was synthesized according to the same procedure described for compound (2R/S) starting from compound 1R (3.62 g, 7.64 mmol). N-Fluorenylmethoxycarbonyl-S-[2,3-bis(palmitoyloxy)-(2R)-propyl]-(R)-cysteine tert-butyl ester (2R, 5.12 g) was obtained as white solid in 71% isolated yield.

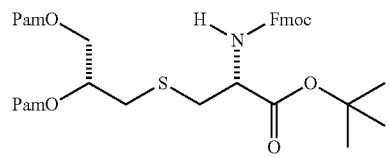

White solid, mp=56-57° C. (lit.$^2$ 45° C.); $^1$H NMR (300 MHz, CDCl$_3$) δ 0.878 (t, J=6.93 Hz, 6H), 1.25 (br, 48H), 1.49 (s, 9H), 1.55-1.63 (br, 4H), 2.26-2.33 (m, 4H), 2.77 (d, J=6.40 Hz, 2H), 3.02 (dd, J=13.8, 5.24 Hz, 1H), 3.09 (dd, J=13.8, 4.64 Hz, 1H), 4.15 (dd, J=11.9, 5.90 Hz, 1H), 4.21-4.40 (m, 4H), 4.49-4.54 (m, 1H), 5.14-5.18 (m, 1H), 5.71 (d J=7.60 Hz, 1H), 7.32 (t, J=7.39 Hz, 2H), 7.40 (t, J=7.31 Hz, 2H), 7.62 (d, J=7.44 Hz, 2H), 7.77 (d, J=7.44 Hz, 2H); $^{13}$C NMR (75 MHz, CDCl$_3$) δ 14.1, 22.7, 24.81, 24.83, 27.9, 29.1, 29.2, 29.3, 29.4, 29.62, 29.66, 31.9, 33.2, 34.0, 34.2, 35.3, 47.0, 54.3, 63.4, 67.1, 70.2, 82.9, 119.9, 125.08, 125.13, 127.0, 127.6, 141.2, 143.7, 155.7, 169.4, 173.0, 173.3; LRMS (ESI) m/z Calcd for $C_{57}H_{91}NO_8SNa$ (M+Na)$^+$ 972.6, obsd 972.8.

Synthesis of N-Fluorenylmethoxycarbonyl-S-[2,3-bis(palmitoyloxy)-(2RS)-propyl]-(R)-cysteine (3R/S)[1-2]

Compound 2R/S (1.0 g, 1.05 mmol) was dissolved in trifluoroacetic acid (20 mL) and the resulting mixture was stirred at room temperature for 1 hour. The reaction mixture was concentrated under reduced pressure and the resulting oily residue was coevaporated from toluene (30 mL) and dichloromethane (30 mL). The residue was lyophilized from tert-butyl alcohol to give N-Fluorenylmethoxycarbonyl-S-[2,3-bis(palmitoyloxy)-(2RS)-propyl]-(R)-cysteine (3R/S, 750 mg) as white solid in 84% isolated yield.

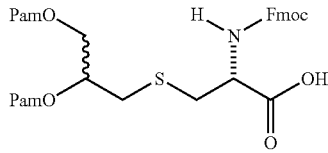

White solid, mp=82-84° C. (lit.[2] 64-65° C.); $^1$H NMR (300 MHz, CDCl$_3$), two diastereoisomers δ 0.878 (t, J=6.88 Hz, 6H), 1.25 (br, 48H), 1.55-1.65 (br, 4H), 2.27-2.38 (m, 4H), 2.70-2.80 (m, 2H), 3.06-3.21 (m, 2H), 4.10-4.41 (m, 5H), 4.61-4.72 (m, 1H), 5.11-5.22 (m, 1H), 5.78 (d, J=7.81H, 1H), 7.31 (td, J=7.44, 1.10 Hz, 2H), 7.40 (t, J=7.34 Hz, 2H), 7.61 (d, J=7.29 Hz, 2H), 7.76 (d, J=7.44 Hz, 2H); $^{13}$C NMR (75 MHz, CDCl$_3$) two diastereoisomers δ 14.1, 22.7, 24.84, 24.87, 29.0, 29.09, 29.11, 29.24, 29.29, 29.36, 29.44, 29.50, 29.66, 29.70, 31.9 (32.79, 32.92), 34.1, 34.3, (34.59, 34.74), 47.0, (53.48, 53.61), (63.51 63.56), 67.4, 70.2, 120.0, 125.1, 127.1, 127.7, 141.3, 143.64, 143.68, (155.89, 155.95), (173.41, 173.46), (173.55, 173.62), (174.20, 174.30) LRMS (ESI) m/z Calcd for $C_{53}H_{84}NO_8S$ (M+H)$^+$ 894.6, obsd 894.5.

Synthesis of N-Fluorenylmethoxycarbonyl-S-[2,3-bis(palmitoyloxy)-(2R)-propyl]-(R)-cysteine (3R)

The title compound was synthesized according to the same procedure described for compound (3R/S) starting from compound 2R (1.50 g, 1.58 mmol) and trifluoroacetic acid (30 mL). N-Fluorenylmethoxycarbonyl-S-[2,3-bis(palmitoyloxy)-(2R)-propyl]-(R)-cysteine (3R, 1.34 g) was obtained as white solid in 95% isolated yield.

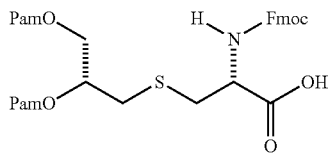

White solid, mp=84-85° C. (lit.[2] 61° C.); $^1$H NMR (300 MHz, CDCl$_3$) δ 0.877 (t, J=6.91 Hz, 6H), 1.25 (br, 48H), 1.55-1.65 (br, 4H), 2.27-2.34 (m, 4H), 2.77 (d, J=6.33 Hz, 2H), 3.06 (dd, J=13.7, 6.13 Hz, 1H), 3.17 (dd, J=14.0, 4.61 Hz, 1H), 4.13-4.19 (m, 1H), 4.21-4.41 (m, 4H), 4.64-4.70 (m, 1H), 5.16-5.19 (m, 1H), 5.79 (d, J=7.86H, 1H), 7.33 (td, J=7.45, 0.95 Hz, 2H), 7.40 (t, J=7.30 Hz, 2H), 7.61 (d, J=7.34 Hz, 2H), 7.76 (d, J=7.45 Hz, 2H), 10.0 (brs, 1H); $^{13}$C NMR (75 MHz, CDCl$_3$) δ 14.1, 22.7, 24.81, 24.85, 29.07, 29.09, 29.26, 29.34, 29.5, 29.64, 29.68, 31.9, 32.9, 34.0, 34.2, 34.6, 47.0, 53.6, 63.5, 67.4, 70.2, 120.0, 125.1, 127.0, 127.7, 141.2, 143.61, 143.65, 156.0, 173.45, 173.55, 174.6; HRMS (ESI) m/z Calcd for $C_{53}H_{84}NO_8S$ (M+H)$^+$ 894.5912, obsd 894.5900.

Synthesis of N-Fluorenylmethoxycarbonyl-S-[2,3-dihydroxy-(2R)-propyl]-(R)-cysteine (4R)

Compound 1R (3.15 g, 6.65 mmol) was dissolved in trifluoroacetic acid (70 mL) and the resulting mixture was stirred at room temperature for 1 hour. The reaction mixture was concentrated under reduced pressure and the resulting oily residue was coevaporated from toluene (50 mL) and dichloromethane (50 mL). The residue was purified by silica gel column chromatography using a mixture of dichloromethane and methanol (9:1=v:v) to give N-Fluorenylmethoxycarbonyl-S-[2,3-dihydroxy-(2R)-propyl]-(R)-cysteine (4R, 1.80 g) as white solid in 65% isolated yield.

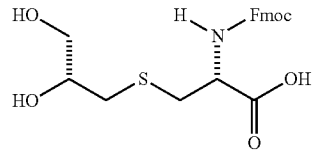

White solid, MP=54-56° C.; $^1$H NMR (300 MHz, DMSO-d$_6$) δ 2.49 (dd, J=13.2, 7.05 Hz, 1H), 2.69 (dd, J=13.5, 4.63 Hz, 1H), 2.78 (dd, J=13.5, 9.69 Hz, 1H), 2.98 (dd, J=13.6, 4.54 Hz, 1H), 3.29-3.39 (m, 2H), 3.54-3.61 (m, 1H), 4.10-4.17 (m, 1H), 4.21-4.30 (m, 3H), 4.50-5.20 (br, 2H), 7.33 (t, J=7.32 Hz, 2H), 7.42 (t, J=7.31 Hz, 2H), 7.73-7.78 (m, 3H), 7.89 (d, J=7.44 Hz, 2H); $^{13}$C NMR (75 MHz, CDCl$_3$) δ 34.9, 35.5, 46.9, 53.8, 64.9, 67.3, 71.1, 120.0, 125.1, 127.1, 127.7, 141.2, 143.47, 143.63, 156.5, 173.7; HRMS (ESI) m/z Calcd for $C_{21}H_{23}NO_6SNa$ (M+Na)$^+$ 440.1138, obsd 440.1133.

REFERENCES 1. (a) Kanzler et al., *Nat Med* 2007, 13(5), 552-9; (b) Zuany-Amorim et al., *Nat Rev Drug Discov* 2002, 1 (10), 797-807.
2. (a) Jarnicki et al., *Journal of immunology* 2008, 180 (6), 3797-806; (b) Marshall et al., *Cancer research* 2012, 72 (3), 581-91; (c) Adams, *Immunotherapy* 2009, 1 (6), 949-64.
3. (a) Akira and Takeda, *Nat Rev Immunol* 2004, 4(7), 499-511; (b) West et al., *Annu Rev Cell Dev Biol* 2006, 22, 409-37.
4. Jin and Lee, *Immunity* 2008, 29 (2), 182-91.
5. Ozinsky et al., *Proc Natl Acad Sci USA* 2000, 97 (25), 13766-71.
6. (a) Janeway and Medzhitov, *Annu Rev Immunol* 2002, 20, 197-216; (b) Akira et al., *Nat Immunol* 2001, 2 (8), 675-80; (c) Kawai and Akira, *Nat Immunol* 11 (5), 373-84.
7. Hennessy et al., *Nat Rev Drug Discov* 9 (4), 293-307.

8. (a) Simons et al., *Urol Oncol* 2008, 26 (4), 341-5; (b) Murata, *Cancer Sci* 2008, 99 (7), 1435-40.
9. (a) D'Agostini et al., *Int Immunopharmacol* 2005, 5 (7-8), 1205-12; (b) Garay et al., *Eur J Pharmacol* 2007, 563 (1-3), 1-17; (c) De Ridder et al., *Int J Radiat Oncol Biol Phys* 2006, 66 (5), 1473-80.
10. (a) Cho and Celis, *Cancer Res* 2009, 69 (23), 9012-9; (b) Celis, *Cancer Res* 2007, 67 (17), 7945-7; (c) Guevara-Patino et al., *J Clin Invest* 2006, 116 (5), 1382-90.
11. American Cancer Society. Cancer facts & figures-2012, p. v.
12. (a) Ferrone et al., *J Gastrointest Surg* 2008, 12 (4), 701-6; (b) Howard et al., *J Gastrointest Surg* 2006, 10 (10), 1338-45; discussion 1345-6.
13. (a) Angst and Kim-Fuchs, *J Gastrointest Surg* 2012, 16 (3), 673; (b) Esposito et al., *Ann Surg Oncol* 2008, 15 (6), 1651-60; (c) Campbell et al., *Histopathology* 2009, 55 (3), 277-83.
14. (a) van Dam et al., *Nature medicine* 2011, 17 (10), 1315-9; (b) Sevick-Muraca et al., *Radiology* 2008, 246 (3), 734-41; (c) Tagaya et al., *Am J Surg* 2008, 195 (6), 850-3; (d) Stummer et al., *Lancet Oncol* 2006, 7 (5), 392-401; (e) Hadjipanayis et al., *Semin Oncol* 2011, 38 (1), 109-18; (f) Keereweer et al., *Curr Pharm Biotechnol* 2012; (g) Ntziachristos et al., *J Biomed Opt* 15 (6), 066024.
15. (a) Nguyen et al., *Proc Natl Acad Sci USA* 2010, 107 (9), 4317-22; (b) Ntziachristos et al., *Journal of biomedical optics* 2010, 15 (6), 066024.
16. Morse et al., *Biochem Pharmacol* 80 (5), 748-54.
17. (a) Muhlradt et al., *The Journal of experimental medicine* 1997, 185 (11), 1951-8; (b) Muhlradt et al., *Infect Immun* 1998, 66 (10), 4804-10; (c) Takeuchi et al., *Int Immunol* 2001, 13 (7), 933-40.
18. (a) Alexopoulou et al., *Nature medicine* 2002, 8 (8), 878-84; (b) Morr et al., *European journal of immunology* 2002, 32 (12), 3337-47; (c) Takeuchi et al., *J Immunol* 2002, 169 (1), 10-4; (d) Jin et al, *Cell* 2007, 130 (6), 1071-82; (e) Manavalan et al., *Front Physiol* 2011, 2, 41; (f) Kang et al., *Immunity* 2009, 31 (6), 873-84; (g) Buwitt-Beckmann et al., *Gastroenterol Res Pract* 2010, 240365.
19. (a) Cheng et al., *J Immunol* 2008, 181 (1), 22-6; (b) Uhlar and Whitehead, *Eur J Biochem* 1999, 265 (2), 501-23.
20. Manukyan et al., *European journal of immunology* 2005, 35 (3), 911-21.
21. Fujimoto et al., *Chembiochem* 2009, 10 (14), 2311-5.
22. Czarniecki, *J Med Chem* 2008, 51 (21), 6621-6.
23. (a) Handl et al., *Anal Biochem* 2005, 343 (2), 299-307; (b) Xu et al., *Mol Cancer Ther* 2009, 8 (8), 2356-65; (c) Barkey et al., *Journal of medicinal chemistry* 2011, 54 (23), 8078-84; (d) Josan et al., *Org Lett* 2009, 11 (12), 2479-82.
24. (a) Agnihotri et al., *Journal of medicinal chemistry* 2011, 54 (23), 8148-60; (b) Salunke et al., *Journal of medicinal chemistry* 2012.
25. Kimbrell et al., *Immunol Lett* 2008, 118 (2), 132-41.
26. (a) Vagner et al., *Angew Chem Int Ed Engl* 2008, 47 (9), 1685-8; (b) Krchnak et al., *Int J Pept Protein Res* 1988, 32 (5), 415-6; (c) Krchnak and Vagner, *Pept Res* 1990, 3 (4), 182-93.
27. (a) Metzger et al., *Int J Pept Protein Res* 1991, 38 (6), 545-54; (b) Reichel et al., *J Am Chem Soc* 1999, 121 (35), 7989-7997.
28. Schindler and Baichwal, *Mol Cell Biol* 1994, 14 (9), 5820-31.
29. Handl et al., *Anal Biochem* 2004, 330 (2), 242-50.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. A composition comprising a targeting imaging probe that has the structure

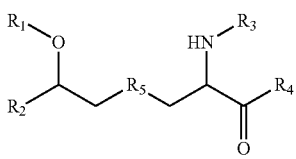

wherein $R_1$ is —CO—$R_6$, wherein $R_6$ is $C_{12}$ to $C_{18}$ alkyl; wherein $R_2$ is —CH$_2$—O—CO—$R_7$, wherein $R_7$ is $C_{12}$ to $C_{18}$ alkyl;
wherein $R_3$ is $R_8$-detectable label, wherein $R_8$ is acetyl-PEGO- (Ac-PEGO), palmitoyl-, acetyl-6-aminohexanoyl- (Ac-Aha), adapalenoyl-, acetyl-11-aminoundecanoyl- (Ac-Aun), or tretinoyl-;
wherein $R_4$ is -Gly-DSer-PEGO-NH$_2$, -Gly-DSer-NH$_2$, -Ser-(Lys)$_4$-NH$_2$, -Gly-Asn-Asn-Asp-Glu-Ser-Asn-Ile-Ser-Phe-Lys-Glu-Lys-NH$_2$, -Ser-Arg-Phe-Asp-Glu-Asp-Asp-Leu-Glu-NH$_2$, -Gly-Ser-Gln-Asn-Leu-Ala-Ser-Leu-Glu-Glu-NH$_2$, or -serine methyl ester; and
wherein $R_5$ is —S—.

2. The composition of claim 1, wherein the targeted imaging probe comprises dipalmitoyl-S-glyceryl-L-Cys-Ser-(Lys)$_4$ (Pam$_2$CSK$_4$).

3. The composition of claim 1, wherein the targeted imaging probe comprises tripalmitoyl-S-glyceryl-L-Cys-Ser-Lys-Lys-Lys-Lys (Pam$_3$CSK$_4$).

4. The composition of claim 1, wherein the targeted imaging probe comprises Ac-PEGO-Dhc(Pam)$_2$-Gly-Ser-PEGO-NH$_2$ (T-02).

5. The composition of claim 1, wherein the targeted imaging probe comprises Ac-PEGO-Dhc(Pam)$_2$-Ser-Arg-Phe-Asp-Glu-Asp-Asp-Leu-Glu-NH$_2$ (T-03; SEQ ID NO:5).

6. The composition of claim 1, wherein the targeted imaging probe comprises Ac-PEGO-Dhc(Pam)$_2$-Gly-Ser-Gln-Asn-Leu-Ala-Ser-Leu-Glu-Glu-NH$_2$ (T-05; SEQ ID NO:6).

7. The composition of claim 1, wherein the detectable label is a near-infrared fluorophore.

8. The composition of claim 7, wherein the near-infrared fluorophore is IRDye800CW or Europium diethylenetriaminepentaacetic acid (Eu-DTPA).

9. The composition of claim 1, wherein $R_4$ is -Gly-Asn-Asn-Asp-Glu-Ser-Asn-Ile-Ser-Phe-Lys-Glu-Lys-NH$_2$.

10. A kit comprising two or more targeted imaging probes in two or more containers, wherein at least one of the two or more targeted imaging probes comprises the composition according claim 1, wherein the detectable label is a near-infrared (NIR) fluorophore.

11. A non-invasive method for in vivo detection of cancer cells in a subject, the method comprising: administering to the subject a targeted imaging probe of claim 1; and
 imaging the subject with a molecular imaging device to detect the targeted imaging probe in the subject,
 wherein detection of the targeted imaging probe in an organ of a subject is an indication of cancer cells in the organ.

12. The method of claim 11, wherein the molecular imaging device comprises a gamma radiation detector.

13. The method of claim 11, wherein the targeted imaging probe comprises Ac-PEGO-Dhc(Pam)$_2$-Gly-Ser-Gln-Asn-Leu-Ala-Ser-Leu-Glu-Glu-NH$_2$ (T-05; SEQ ID NO:6).

14. The method of claim 11, wherein the targeted imaging probe comprises dipalmitoyl-S-glyceryl-L-Cys-Ser-(Lys)$_4$ (Pam$_2$CSK$_4$).

15. The method of claim 11, wherein the targeted imaging probe comprises tripalmitoyl-S-glyceryl-L-Cys-Ser-Lys-Lys-Lys-Lys (Pam$_3$CSK$_4$).

16. The method of claim 11, wherein the targeted imaging probe comprises Ac-PEGO-Dhc(Pam)$_2$-Gly-Ser-PEGO-NH$_2$ (T-02).

17. The method of claim 11, wherein the targeted imaging probe comprises Ac-PEGO-Dhc(Pam)$_2$-Ser-Arg-Phe-Asp-Glu-Asp-Asp-Leu-Glu-NH$_2$ (T-03; SEQ ID NO:5).

18. The method of claim 11, wherein the detectable label is a near-infrared (NIR) fluorophore.

19. The method of claim 11, wherein the cancer cells are metastasized cancer cells.

20. The method of claim 11, wherein the cancer cells are pancreatic cancer cells.

21. The method of claim 18, wherein the near-infrared fluorophore is IRDye800CW or Europium diethylenetriaminepentaacetic acid (Eu-DTPA).

22. The method of claim 11, wherein R$_4$ is -Gly-Asn-Asn-Asp-Glu-Ser-Asn-Ile-Ser-Phe-Lys-Glu-Lys-NH$_2$.

* * * * *

UNITED STATES PATENT AND TRADEMARK OFFICE
CERTIFICATE OF CORRECTION

Page 1 of 2

PATENT NO. : 10,406,248 B2
APPLICATION NO. : 14/240305
DATED : September 10, 2019
INVENTOR(S) : David L. Morse et al.

It is certified that error appears in the above-identified patent and that said Letters Patent is hereby corrected as shown below:

In the Specification

Column 1, Line 43, please replace the term "cancers" with --cancer--.
Column 1, Line 54, please replace the term "intraoperative" with --intraoperatively--.
Column 4, Line 33, please replace the phrase "three of more" with --three or more--.
Column 6, Line 25, please replace the term "A" with --15A--.
Column 6, Line 26, please replace the term "B" with --15B--.
Column 6, Line 28, please replace the term "C" with --15C--.
Column 6, Line 34, please replace the term "A" with --16A--.
Column 6, Line 36, please replace the term "B" with --16B--.
Column 6, Line 44, please replace the term "C" with --16C--, and the term "D" with --16D--.
Column 6, Line 49, please replace the term "A" with --17A--.
Column 6, Line 56, please replace the term "B" with --17B--.
Column 6, Line 57, please replace the term "C" with --17C--.
Column 7, Line 12, please replace the phrase "A) 9, B) 8, C) 3, D) 11, E)" with --20A) 9, 20B) 8, 20C) 3, 20D) 11, 20E)--.
Column 7, Line 13, please replace the phrase "F) Pam2CSK4 and G) Pam3CSK4" with --20F) Pam2CSK4 and 20G) Pam3CSK4--.
Column 7, Line 22, please replace the term "A" with --21A--.
Column 7, Line 24, please replace the term "B" with --21B--.
Column 7, Line 29, please replace the term "A" with --22A--.
Column 7, Line 30, please replace the term "B" with --22B--.
Column 7, Line 31, please replace the term "C" with --22C--.
Column 21, Line 11, please replace the phrase "By non-invasive is" with --By non-invasive it is--.
Column 21, Line 20, please replace the term "contimplated" with --contemplated--.
Column 23, Line 22, please replace the term "and lung" with --lung--.
Column 48, Line 29, please replace the term "FIG. 13" with --FIGs. 13A and 13B--.
Column 49, Line 1, please replace the phrase "FIG. 15" with --FIG. 15C--.
Column 52, Line 55, please replace the phrase "a europium" with --an europium--.
Column 54, Line 2, please replace the phrase "determined the Kd" with --determined that the Kd--.

Signed and Sealed this
Seventeenth Day of November, 2020

Andrei Iancu
*Director of the United States Patent and Trademark Office*

CERTIFICATE OF CORRECTION (continued)
U.S. Pat. No. 10,406,248 B2

Column 54, Line 11, please replace the phrase "17B and C" with --17B and 17C--.
Column 54, Line 12, please replace the phrase "22A and C" with --22A and 22C--.
Column 56, Line 17, please replace the phrase "cell lines is" with --cell lines are--.
Column 58, Line 5, please replace the phrase "N-terminus of" with --N-terminus of H-PEGO-Dhc(Pam2)-Gly-DSer-PEGO-resin--.
Column 58, Line 26, please replace the phrase "N-terminus H-PEGO-Dhc(Pam2)-Gly-DSer-" with --N-terminus of H-PEGO-Dhc(Pam2)-Gly-DSer- --.

In the Claims

Claim 1, Column 73, Line 44, please replace the term "targeting" with --targeted--.

SEQUENCE LISTING

```
<160> NUMBER OF SEQ ID NOS: 11

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
ctggcatcat gtatttaggg gc                                              22

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
gagttgcgcc tgtcagaaac                                                 20

<210> SEQ ID NO 3
<211> LENGTH: 24
```

```
<212> TYPE: DNA
<213> ORGANISM: Artificial Sequence
<220> FEATURE:
<223> OTHER INFORMATION: Synthetic primer

<400> SEQUENCE: 3
cttcttcaag agttcataga cgac                                          24

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
tgctcagagt tcatccgtt tg                                             22

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Ser Arg Phe Asp Glu Asp Asp Leu Glu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Gly Ser Gln Asn Leu Ala Ser Leu Glu Glu
1               5                   10

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
tctcccagtg tttggtgttg                                               20

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
tggtgttcat tatcttccgc ag                                            22

<210> SEQ ID NO 9
<211> LENGTH: 104
<212> TYPE: PRT
<213> ORGANISM: Artificial Sequence
<220> FEATURE:
<223> OTHER INFORMATION: Synthetic peptide
```

```
<400> SEQUENCE: 9

Met Arg Ser Phe Phe Ser Phe Leu Gly Glu Ala Phe Asp Gly Ala Arg
1               5                   10                  15

Asp Met Trp Arg Ala Tyr Ser Asp Met Arg Glu Ala Asn Tyr Ile Gly
                20                  25                  30

Ser Asp Lys Tyr Phe His Ala Arg Gly Asn Tyr Asp Ala Ala Lys Arg
            35                  40                  45

Gly Pro Gly Gly Val Trp Ala Ala Glu Ala Ile Ser Asp Arg Glu Asn
        50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide

<400> SEQUENCE: 10

Gly Asn Asn Asp Glu Ser Asn Ile Ser Phe Lys Glu Lys
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Cys Ser Lys Lys Lys Lys
1               5
```